(12) United States Patent
Michels et al.

(10) Patent No.: US 8,580,549 B2
(45) Date of Patent: Nov. 12, 2013

(54) ESTERASES FOR SEPARATING PLASTICS

(75) Inventors: Andreas Michels, Düsseldorf (DE);
André Pütz, Düsseldorf (DE);
Karl-Heinz Maurer, Erkrath (DE);
Thorsten Eggert, Essen (DE);
Karl-Erich Jäger, Mülheim (DE)

(73) Assignee: Henkel KGaA, Duesseldorf (DE)

( * ) Notice: Subject to any disclaimer, the term of this patent is extended or adjusted under 35 U.S.C. 154(b) by 907 days.

(21) Appl. No.: 11/989,927

(22) PCT Filed: Aug. 3, 2006

(86) PCT No.: PCT/EP2006/007693
§ 371 (c)(1),
(2), (4) Date: Jul. 23, 2008

(87) PCT Pub. No.: WO2007/017181
PCT Pub. Date: Feb. 15, 2007

(65) Prior Publication Data
US 2009/0258406 A1 Oct. 15, 2009

(30) Foreign Application Priority Data
Aug. 5, 2005 (DE) .......................... 10 2005 037 659

(51) Int. Cl.
C12N 9/18 (2006.01)
C12N 9/16 (2006.01)
C12Q 1/44 (2006.01)
C07K 14/00 (2006.01)
C12P 21/00 (2006.01)

(52) U.S. Cl.
USPC ............ 435/197; 435/196; 435/69.1; 435/19; 530/350

(58) Field of Classification Search
USPC .................................. 435/197, 196, 69.1, 19
See application file for complete search history.

(56) References Cited

U.S. PATENT DOCUMENTS

| 3,893,929 | A | | 7/1975 | Basadur |
| 5,468,632 | A | | 11/1995 | Cantwell et al. |
| 5,783,545 | A | | 7/1998 | Paatz et al. |
| 5,906,930 | A | | 5/1999 | Arnold et al. |
| 5,945,325 | A | * | 8/1999 | Arnold et al. ................. 435/197 |
| 7,494,798 | B2 | * | 2/2009 | Berka et al. ................... 435/209 |
| 7,824,885 | B2 | * | 11/2010 | Bryan .......................... 435/69.7 |
| 2003/0040457 | A1 | * | 2/2003 | Behler et al. .................. 510/421 |
| 2004/0005695 | A1 | | 1/2004 | Miksch et al. |

FOREIGN PATENT DOCUMENTS

| DE | 2253063 | | 5/1973 |
| EP | 0 549 264 A1 | | 6/1993 |
| EP | 0 736 084 B1 | | 10/1996 |
| JP | 09-224664 | | 9/1997 |
| JP | 11-169177 | | 6/1999 |
| JP | 2000-508903 A | | 7/2000 |
| JP | 2002-543271 A | | 12/2002 |
| WO | WO-91/02792 A1 | | 3/1991 |
| WO | WO-97/40144 A1 | | 10/1997 |
| WO | WO-00/66696 A1 | | 11/2000 |
| WO | WO-01/81597 A1 | | 11/2001 |
| WO | WO-2004/016669 A2 | | 2/2004 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Zock et al., GenBank accession No. PNBA_BACSU GI 585706, 2004.*
Zock et al., GenBank accession No. PNBA_BACSU, GI 68845777 Jul. 5, 2005.*
Veith et al., GenBank AAU39577, Sep. 20, 2004.*
Evans et al., GenBank accession No. AAG31026, Feb. 17, 2004.*
Lipman, D. J., et al., "Rapid and sensitive protein similarity searches", Science, 1985, vol. 227, pp. 1435-1441.
Arpigny, J. L., et al., "Bacterial lipolytic enzymes: classification and properties", Biochem. J., 1999, vol. 343, pp. 177-183.
Bryan, P. N., "Protein engineering of subtilisin", Biochimica et Biophysica Acta, 2000, vol. 1543, pp. 203-222.
Veith, B., et al., "The complete genome sequence of *Bacillus licheniformis* DSM13, an organism with great industrial potential", J. Mol. Microbiol. Biotechnol., 2004, vol. 7, pp. 204-211.
"PnbA (Para-nitrobenzyl esterase)", Database EMBL, XP002432701, Accession No. Q65MY7, Jan. 25, 2005.
"PNB esterase 56C8", Database PDB, XP002421545, Accession No. 1C7J, Feb. 21, 2000.
"PNB esterase", Database PDB, XP002421546, Accession No. 1QE3, Jul. 12, 1999.
Spiller, B., et al., "A structural view of evolutionary divergence", PNAS, 1999, vol. 96, No. 22, pp. 12305-12310.
Zock, J., et al., "The *Bacillus subtilis pnbA* gene encoding *p*-nitrobenzyl esterase: cloning, sequence and high-level expression in *Escherichia coli*", Gene, 1994, vol. 151, pp. 37-43.

* cited by examiner

*Primary Examiner* — Delia Ramirez
(74) *Attorney, Agent, or Firm* — Krista A. Kostiew

(57) ABSTRACT

The invention relates to agents containing esterases, and to the use thereof for dressing fibres, in particular, artificial fibres, washing and cleaning agents comprising esterases and corresponding washing and cleaning methods, in addition to additional technical areas of application. The invention also relates to the use of esterases for protecting against or reducing and/or preventing pilling, preferably in textiles, particularly plastic fibres, more preferably polyester fibres, in addition to the use of esterases for separating the plastics, in particular, polyester compounds. The invention further relates to novel esterases and to sufficiently related proteins and to derivatives thereof, agents containing them and to the use thereof.

10 Claims, 5 Drawing Sheets

Figure 1:
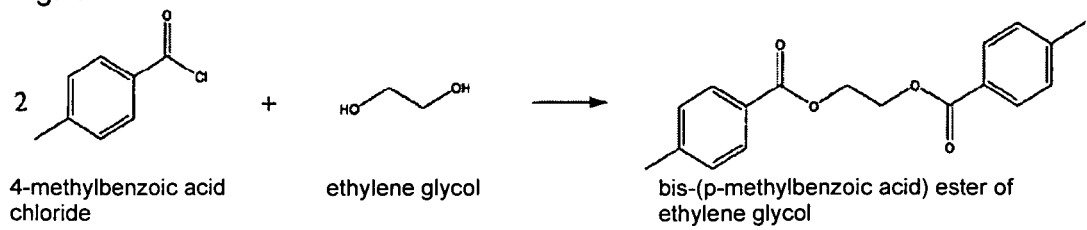

4-methylbenzoic acid chloride     ethylene glycol     bis-(p-methylbenzoic acid) ester of ethylene glycol bis-(p-methylbenzoic acid) ester of ethylene glycol     4-methylbenzoic acid     ethylene glycol y-axis: specific activity [micromol/min*mg]
x-axis: substrate concentration PET dimer [mM]

y axis: specific activity [micromol/min*mg]
x-axis: substrate concentration DMP[mM]

y axis: specific activity [micromol/min*mg]
x-axis: substrate concentration DMIP[mM]

y axis: specific activity [micromol/min*mg]
x-axis: substrate concentration DMT [mM]

y axis: specific activity [micromol/min*mg]
x-axis: substrate concentration DMP [mM]

y axis: specific activity [micromol/min*mg]
x-axis: substrate concentration DBP [mM]

y axis: specific activity [micromol/min*mg]
x-axis: substrate concentration DEP [mM]

y axis: specific activity [micromol/min*mg]
x-axis: substrate concentration DMT [mM]

y axis: specific activity [micromol/min*mg]
x-axis: substrate concentration DET [mM]

ESTERASES FOR SEPARATING PLASTICS

RELATED APPLICATIONS

This application is a national stage application under 35 U.S.C. 371 of PCT/EP2006/007693, filed Aug. 3, 2006, which is incorporated by reference in its entirety and claims benefit of German application 10 2005 037 659.2, filed Aug. 5, 2005, which is incorporated by reference in its entirety.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence Listing H06819 13744-53_ST25, date recorded: Jan. 30, 2008, size: 93 KB.

The present invention relates to agents containing esterases, especially para-nitrobenzyl esterases, as well as their use for finishing fibers, in particular, artificial fibres, to detergents and cleaning agents comprising esterases and corresponding washing and cleaning methods in addition to further industrial areas of application. The invention particularly relates to the use of esterases for protecting against or reducing and/or preventing pilling, preferably in textiles, particularly artificial fibers, more preferably polyester fibers, as well as the use of esterases for the cleaving of plastics, in particular, polyester compounds. The invention further relates to novel esterases and to sufficiently related proteins and to derivatives thereof, agents containing them and to the use thereof.

In general, esterases represent a group of hydrolytic enzymes with an inherently broad diversity in regard to the substrate and the reaction type. The substrate specificity and the activation of the enzymes differ from those of the lipases. It is known that lipases are activated through the lipid/water interface before they hydrolyze water-insoluble substrates containing long chain fatty acid esters. According to Arpigny (Arpigny, Jager, 1999 Biochem. J. 343, pp. 177-183), the esterases (EC 3.1.1) are subdivided into three different classes: the true lipases (EC 3.1.1.3), carboxyl esterases (EC 3.1.1.1) and various types of phospholipases. However, the physiological functions of many esterases, e.g. the para-nitrobenzyl esterases (PNB esterases), have still not been elucidated. Normally the esterolytic enzymes are characterized in that they possess preserved regions that comprise the catalytic triads as well as in their ability to catalyze a broad spectrum of reactions. In this respect each hydrolase possesses a specific stereo preference in regard to a given substrate under specific reaction conditions, which can be identified as its characteristic fingerprint. Esterases can be used for the enzymatic hydrolysis of racemic carboxylic acid esters into their corresponding carboxylic acids and alcohols. Moreover, they can be used for transesterification and for the synthesis of esters. The ability of esterases to be active both in aqueous as well as in non-aqueous systems makes them important tools for organic synthesis. In this respect esterases are of particular interest for the synthesis of enantiomerically pure products.

As a prerequisite for the commercial utilization of esterases it is desirable to obtain more information on the biocatalytic properties of the esterases that catalyze reactions of organic compounds.

Pilling is understood to mean fine fibers that are pulled out from fabrics or knitted fabrics by rubbing and which coil up to form pills or bobbles that are then only joined to the surface of the fabric or knitted fabric by a few single fibers. In artificial fibers the small bobbles of fiber adhere to the surface of the fabric. Accordingly, solutions are sought after which firstly reduce the formation of the bobbles (depilling) and secondly protect the fibers from pilling, such that the unesthetic bobble formation does not even occur.

The use of cellulases for anti-pilling finishing of cotton and other natural fibers or fabrics is known. However, the cellulases are not very suitable for treating the formation of bobbles or globules in artificial fibers such as for example polyesters or polyacrylic fibers.

Accordingly the object of the present invention was to discover new suitable ways to counteract pilling, especially of polyester or polyacrylic fibers and/or to get rid of or disintegrate the resulting bobble-like structures. A further object consisted in the provision of novel esterases, especially for use in detergents and/or cleaning agents.

These objects are achieved by the use of esterases for finishing fibers, especially artificial fibers, in particular for anti-pilling finishing, detergents and cleaning agents as well as finishing agents for fabrics, in particular fabric post treatment and pre-treatment agents that comprise esterases, corresponding finishing, washing and cleaning processes and the use of esterases in detergents and cleaning agents as well as additional industrial applications. The invention particularly relates to the use of esterases for protecting against or reducing or preventing pilling, preferably in textiles, particularly artificial fibers, more preferably polyester fibers, as well as the use of esterases for the cleaving of plastics, in particular, polyester compounds.

When pilling is prevented, or particularly with textiles, the bobbles on the fibers are reduced, then the garment has a higher wearing comfort, in particular due to the improved softness, and the garment retains a good or new appearance much longer.

A further subject of the invention relates to novel esterases and to sufficiently related proteins and to derivatives thereof, agents containing them and to the use thereof in particular for the finishing of fibers.

Additional subsidiary objects consisted in the provision of nucleic acids that code for these types of esterases, and the provision of vectors, host cells and manufacturing processes that can be utilized for the production of such esterases. In addition, it was the intention to provide suitable agents, especially detergents and cleaning agents, suitable washing and cleaning processes as well as suitable end-use applications for these types of esterases.

The object is achieved by the use of esterases (EC 3.1.1), especially carboxyl esterases (EC 3.1.1.1), preferably para-nitrobenzyl esterases, especially those that can be obtained from microorganisms, particularly bacteria, preferably from bacteria of the *Bacillus* species.

Those esterases, which according to the methods 2.4 cited in the examples exhibit a specific activity towards the substrate bis-(p-methylbenzoic acid) ester of ethylene glycol of 0.1 to 30, preferably 0.6 to 20, particularly 0.7 to 15, quite particularly preferably 0.9 to 10, even more strongly preferably 1 to 5, particularly 1.1 to 4, quite particularly preferably 1.5 to 3 (µmol liberated acid)/(min mg enzyme), are particularly suitable for use in the inventive agents as well as also for the inventive use, listed below, of such esterases. These esterases have proved to be particularly advantageous for use in the inventive agents or uses and processes.

Esterases are particularly suitable that contain amino acid sequences that are identical to the amino acid sequences listed in SEQ ID NO. 1, 2, 4, 6, 11-26 to at least 50%, preferably 60%, particularly 70%, preferably at least to 80%, particularly preferably at least to 90%, preferably at least to 95% and quite particularly preferably to 100%, or are homologous to at least 90%, preferably at least 95% and quite particularly preferably to 100%.

Further solutions to the object or to the subsidiary objects and therefore to each of the individual subjects of the invention consist in nucleic acids whose sequences are sufficiently similar to the nucleotide sequences given in SEQ ID NO. 3, 4, 7 or 8 or which code for inventive esterases, in corresponding vectors, cells, or host cells and manufacturing processes. In addition, suitable agents, especially detergents and cleaning agents, suitable washing and cleaning processes as well as suitable end-use applications for these types of esterases are provided. Finally, industrial applications for the discovered esterases are defined.

Esterases that are particularly preferred for use in the inventive agents and also for the inventive uses listed further below are those that are homologous to the protein sequence listed in Seq. ID Nr. 12 to at least 50%, at least 55%, particularly at least 60%, preferably at least 65%, particularly preferably at least 70%, advantageously at least 75%, quite particularly preferably at least 80%, particularly preferably at least 85%, at least 90%, at least 95%, at least 99%, particularly 100%.

In the context of the present application, a protein is understood to mean a polymer composed of natural amino acids, which is essentially linear in structure and which assumes in the main a three dimensional structure for carrying out its function. In the present application, the 19 naturally occurring L-amino acids that serve as building blocks of proteins, are designated with the customary international 1- and 3 letter codes. The combination of one of these designations with a number designates which amino acid group is in which position in the relevant protein. Analogous designations are established for point mutations. Positional data refer, when not otherwise stated, to each of the mature forms of the protein in question, i.e. without the signal peptide (see below).

In the context of the present application, an enzyme is understood to mean a protein that has a specific biochemical function.

Numerous proteins are so called preproteins, i.e. formed together with a signal peptide. Included among these is the N-terminal part of the protein, whose function is mainly to guarantee the expulsion of the formed protein from the production cells into the periplasma or the surrounding medium and/or its correct folding. Subsequently, the signal peptide is split off from the remaining protein under natural conditions by a signal peptidase, such that this exercises its original catalytic activity without the first present N-terminal amino acids.

Due to their enzymatic activity, the mature peptides, i.e. the enzymes processed after their production, are preferred over the preproteins for industrial applications.

In the context of the present application, nucleic acids are understood to mean the molecules that are naturally constructed from nucleotides, which serve as information carriers and code for the linear amino acid sequence in proteins or enzymes. They can be present as a single strand, as a complementary single strand to this single strand or as a double strand. Nucleic acid DNA is preferred as the naturally, long lasting information carrier for molecular biological work. On the other hand, an RNA is formed for the realization of the invention in natural surroundings, such as for example in an expression cell, which is why RNA molecules that are essential for the invention also represent embodiments of the present invention. (c-) DNA molecules can once again be derived from them, for example by reverse transcription.

The information unit of a nucleic acid corresponding to a protein is also designated as a gene in the context of the present application. In DNA the sequences of both complementary strands have to be taken into account in each of all three possible reading frames. In addition, it has to be taken into account that different codon triplets can code for the same amino acids, with the result that a specific amino acid sequence can be derived from a plurality of different and nucleotide sequences exhibiting possibly only slight identity (degeneracy of the genetic code). Moreover, various organisms exhibit differences in the use of these codons. On these grounds, both amino acid sequences as well as nucleotide sequences have to be included in considerations of the field of protection, and listed nucleotide sequences are only to be regarded as an example of coding for a specific amino acid sequence.

Using today's generally known methods, such as for example chemical synthesis or the polymerase chain reaction (PCR) in combination with molecular biological and/or protein chemical standard methods, it is possible for the person skilled in the art to manufacture, with the help of known DNA sequences and/or amino acid sequences, the complete genes. Such methods are known to the person skilled in the art. In particular, this is possible if one can revert to a strain deposited in a collection of strains. For example, with PCR primers, which can be synthesized by means of a known sequence, and/or through isolated mRNA molecules, the gene in question can be synthesized from such strains, cloned and optionally further treated, for example mutagenized.

Modifications of the nucleotide sequence, as can be brought about by known molecular biological methods, are called mutations. Known types depend on the nature of the modification, for example deletion mutations, insertion mutations or substitution mutations or those in which various genes or parts of genes are fused together (shuffling); they are gene mutations. The associated organisms are called mutants. The proteins derived from mutated nucleic acids are called variants. Thus, for example deletion-, insertion-, substitution mutations or fusions lead to deletion-, insertion-, substitution mutants or fusion genes and at the protein level to corresponding deletion-, insertion- or substitution variants or fusion proteins.

In the context of the present invention, vectors are understood to mean elements that consist of nucleic acids, which comprise a gene of interest as the characterizing nucleic acid region. They are able to establish the gene as an independent replicating, stable genetic element in a species or a cell line over several generations or cell divisions. Vectors, particularly when used in bacteria, especially plasmids, are therefore circular genetic elements. In gene technology, a differentiation is made, on the one hand, between those vectors that serve the storage and thereby to a certain extent also the technical genetic work, the so called cloning vectors, and on the other hand, those that fulfill the function of realizing the gene of interest in the host cells, i.e. to enable the expression of the protein in question. These vectors are called expression vectors.

Both bacteria cells and eukaryotic cells, which comprise the cited vectors, are generally called cells regardless of their differences. Such cells that comprise a vector, especially an expression vector and thus can be stimulated to express a transgene, are called host cells because they harbor the relevant genetic system.

Homologization is the comparison of a nucleic acid- or amino acid sequence with that of known genes or proteins. It is conducted, for example, over an alignment. The measure of homology is a percentage rate of the identity, as can be determined for example according to the methods given by by D. J. Lipman and W. R. Pearson in Science 227 (1985), pp. 1435-1441. This result can refer to the whole protein or to each of the attributable regions. A further broad homology term, the similarity, also factors into the evaluation conserved variations, i.e. amino acids with similar chemical activity, because these execute mostly similar chemical activities inside the protein. For nucleic acids, only the percentage rate of identity is known.

By means of homologization, the functions of individual sequence regions as well as the enzymatic activity of the whole enzyme under consideration can be deduced from the amino acid- or nucleotide sequence. Homologous regions of different proteins are those with comparable functions, which can be recognized by identity or conserved exchanges in the primary amino acid sequence. They include single amino acids, the smallest regions, so called boxes that are only a few amino acids long, up to long regions in the primary amino acid sequence. Functions of the homologous regions are thus understood to also mean the smallest partial functions of the function exercised by the whole protein, such as for example the formation of single hydrogen bonds for complexing a substrate or transition complex. Other regions of the protein, which are not involved in the actual enzymatic reaction, can qualitatively or quantitatively modify it. This can concern, for example, the enzyme stability, the activity, the reaction conditions or the substrate specificity.

The term esterase is understood to mean an enzyme with esterase activity or that of an esterase, moreover all functions are therefore understood going from the functions of the few amino acid groups of the catalytically active center, as they result from the action of the total remaining protein or a part or several parts of the remaining protein on the actual catalytically active regions. In the context of the invention, such modifying functions on their own or partial activities, in so far as they support an esterase reaction, are also regarded as esterolytic activity. Such auxiliary functions or partial activities include, for example, the binding of a substrate, of an intermediate or end product, the activation or the inhibition or intervention of a regulating influence on the hydrolytic activity. This can also concern, for example, the formation of a structural element that lies far removed from the active center. The second prerequisite for a protein to be considered according to the invention as having esterase activity, is however, that there results a hydrolysis of ester bonds by the chemical behavior of the actual active groups alone or additionally by the action of the modifying part. Moreover, it is also possible that the activities of other esterases can also be qualitatively or quantitatively modified through one or more parts of the inventive protein, for example. This influence from other factors is also regarded as esterase activity. Active enzymes are also those esterases, whose activity at a given point in time is blocked for example by an inhibitor. What is crucial is their ability in principle in regard to the corresponding esterase reaction.

Preferred enzymes, in particular para-nitrobenzyl esterases, in the context of the invention are particularly those enzymes that are capable of catalysing the hydrolysis of para-nitrophenyl acetate. In addition, all enzymes characterized in data banks as para-nitrobenzyl esterases are preferred and are understood to be among the inventive para-nitrobenzyl esterases.

Those esterases are particularly preferred, which according to the methods 2.4 cited in the examples exhibit a specific activity towards the substrate bis-(p-methylbenzoic acid) ester of ethylene glycol of 0.1 to 30, preferably 0.6 to 20, particularly 0.7 to 15, quite particularly preferably 0.9 to 10, even more strongly preferably 1 to 5, particularly 1.1 to 4, quite particularly preferably 1.5 to 3 (µmol liberated acid)/(min*mg enzyme). These esterases have proved to be particularly advantageous for use in the inventive agents or uses and processes.

Those esterases are particularly preferred which are homologous to the protein sequences listed under Seq. ID Nr. 12 to at least 50%, at least 55%, particularly at least 60%, preferably at least 65%, particularly preferably at least 70%, advantageously at least 75%, quite particularly preferably at least 80%, particularly preferably at least 85%, at least 90%, at least 95%, at least 99%. The esterase according to Seq ID Nr. 12 or fragments of this esterase, in particular those fragments that exhibit an esterase activity, are quite particularly preferred. These esterases particularly exhibit a surprisingly good stability towards higher temperatures and higher pH. It was determined that these esterases are stable for long periods or active at alkaline pH and also at a temperature of greater than or equal to 60° C.

Consequently, the inventive esterases are suitable for use particularly at alkaline pH at high temperatures, in particular in heavy-duty detergents that usually exhibit an alkaline pH, and particularly for hot washes (washing temperature at 95° C.).

Fragments are understood to mean all proteins or peptides, which are smaller than natural proteins or those that correspond to completely translated genes, and for example can also be obtained synthetically. Due to their amino acid sequences, they can be assigned to the relevant complete proteins. For example, they can assume the same structure or exercise proteolytic activities or partial activities. Fragments and deletion variants of starting proteins are in principle very similar; while fragments depict rather smaller debris, the deletion mutants rather lack only short regions, and therefore only a few partial functions.

In the context of the present application, chimeric or hybrid proteins are understood to mean those proteins that are composed of elements that originate naturally from different polypeptide chains from the same organism or from different organisms. This procedure is also called shuffling or fusion mutagenesis. The sense of such a fusion consists in, for example, providing or modifying an enzymatic function with the help of the fused-on inventive protein part.

"Proteins obtained by means of insertion mutation" are understood to mean those variants that have been obtained by known methods of inserting a nucleic acid fragment or protein fragment into the starting sequences. Due to their fundamental similarity, they are classified as chimeric proteins. They differ from those only in the proportion of the size of the unchanged part of the protein to the size of the whole protein. In these insertion mutated proteins, the share of foreign protein is less than in chimeric proteins.

Inversion mutagenesis, meaning a partial reversal of the sequence, can be regarded as a special form of both deletion as well as of insertion. The same is true for new groupings of different molecular parts that differ from the original amino acid sequence. It can be regarded both as a deletion variant, as an insertion variant as well as a shuffling variant of the original protein.

In the context of the present application, derivatives are understood to mean proteins, whose particular amino acid chain has been chemically modified. Such derivatizations can be effected biologically, for example, by the host organism in connection with the protein biosynthesis. Molecular biological methods for example can be employed for this, for example cotransformation with genes that provide the modification in question. However, derivatizations can also be effected chemically, for example by the chemical transformation of a side chain of an amino acid or by the covalent bonding of another compound onto the protein. This type of compound can also concern other proteins for example that are bonded to the inventive protein through a bifunctional chemical compound, for example. These types of modification influence, for example, the substrate specificity or the binding strength to the substrate or provide a temporary blocking of the enzymatic activity in the case where the attached substance is an inhibitor. This can be meaningful for the storage period, for example. Similarly, derivatization is also understood to mean the covalent bonding to a macromolecular support.

In the context of the present invention, all enzymes, proteins, fragments, fusion proteins and derivatives, in so far as they do not need to be explicitly treated as such, are assimilated under the generic term proteins.

"Activity of an enzyme" is understood as its efficiency in each technical field in question, preferably in the context of a suitably targeted agent. This is based on the actual enzymatic activity, but in addition is dependent on further relevant factors for the process in question. These include for example stability, substrate binding, interaction with the material supporting the substrate or interactions with other ingredients, especially synergists.

In the context of the present application, "washing performance" or "cleaning performance" of a detergent or cleaning agent is understood to mean the effect that the agent in question produces on the soiled article, for example fabrics or objects with hard surfaces. Individual components of such agents, for example individual enzymes are assessed in regard to their contribution to the washing performance or cleaning performance of the total detergent or cleaning agent. This is because the enzymatic properties of an enzyme do not allow a straightforward analysis of its contribution to the washing performance of an agent. Other factors play a role, such as stability, substrate binding, binding onto the goods being cleaned or interactions with other ingredients of the detergent or cleaning agent, especially synergies during removal of the soils.

The present invention is based on the finding that esterases, especially selected from Lipase P and p-nitrobenzyl esterases, preferably such enzymes that occur naturally in bacteria, quite particularly in bacteria of the genus *Bacillus*, particularly preferably from the *Bacillus licheniformis* and *subtilis* species, are suitable for reducing or for preventing pilling on textile fibers and textile fabrics.

Polyesters are polymers whose basic components are held together through ester bonds. The "homopolymers" can be classified into two groups according to their chemical structure, the hydroxycarboxylic types (AB-polyesters) and the dihydroxydicarboxylic acid types (AA-BB-polyesters). The former are manufactured from only a single monomer by e.g. polycondensation of an ω-hydroxycarboxylic acid or by ring opening polymerization of cyclic esters (lactones). The synthesis of the latter, on the other hand, is effected by polycondensation of two complementary monomers, e.g. a diol and a dicarboxylic acid. Branched and crosslinked polyesters are obtained by the polycondensation of tri- or polyhydric alcohols with polyfunctional carboxylic acids. The polycarbonates (polyesters of carbonic acid) are also generally counted among the polyesters. AB-Type-P. (I) are inter alia polyglycolic acids (polyglycolides, $R=CH_2$), polylactic acids (polylactides, $R=CH—CH_3$), poly(β-hydroxybutyric acid) [poly (3-hydroxybutyric acid), $R=CH(CH_3)—CH_2$], poly(ε-caprolactone)s [$R=(CH_2)_5$] and polyhydroxybenzoic acids ($R=C_6H_4$).

Pure aliphatic AA-BB-type polyesters (II) are polycondensates of aliphatic diols and dicarboxylic acids, which inter alia are used as products with terminal hydroxyl groups (as polydiols) for the manufacture of polyester polyurethanes [e.g. polytetramethylene adipate, $R^1=R^2=(CH_2)_4$] AA-BB-type polyesters with the greatest industrial volumes are those from aliphatic diols and aromatic dicarboxylic acids, particularly the polyalkylene terephthalates [$R^2=C_6H_4$, with polyethylene terephthalate (PET) $R^1=(CH_2)_2$, polybutylene terephthalate (PBT) $R^1=(CH_2)_4$ and poly(1,4-cyclohexane dimethylene terephthalate)s (PCDT) $R^1=CH_2—C_6H_{10}—CH_2$] as the most important representatives. The properties of these types of polyesters can be broadly varied and matched to various applications by the additional use of other aromatic dicarboxylic acids (e.g. isophthalic acid) or by adding diol mixtures during the polycondensation.

Purely aromatic polyesters are the polyacrylates, which include inter alia the poly(4-hydroxybenzoic acid) (Formula I, $R=C_6H_4$), polycondensates of Bisphenol A and phthalic acid (Formula II, $R^1=C_6H_4C(CH_3)_2C_6H_4$, $R^2=C_6H_4$) or also those of bis-phenols and phosgene.

In addition to the previously cited saturated polyesters, unsaturated polyesters can also be manufactured from unsaturated dicarboxylic acids. These polyester resins have acquired industrial significance, in particular as unsaturated polyester resins (UP-resins).

Polyesters are also found in nature, where they are formed from hydroxycarboxylic acids (e.g. depsides and depsipeptides). Poly(β-hydroxybutyric acid) serves as a storage substance for many bacteria. Sand bees or Miner bees produce polyester from 18-hydroxyoctadecanoic acid and 20-hydroxyeicosanoic acid to line their nests.

According to a preferred embodiment, in particular esterases selected from Lipase P and para-nitrobenzyl esterases are employed as the esterases. These PNB-esterases are characterized in that they provide a particularly good protection of textile fibers against pilling.

In the context of the invention, suitable para-nitrobenzyl esterases (p-nitrobenzyl esterases, pNB-esterases, EST-B) are especially those enzymes as described in the patent applications U.S. Pat. Nos. 5,468,632, 5,906,930, 5,945,325, EP 0 549 264, which are incorporated herein by reference in their entirety. The p-nitrobenzyl esterases disclosed therein are all inventively preferred.

Furthermore, those para-nitrobenzyl esterases are particularly preferred with an amino acid sequence which is identical to the amino acid sequences listed under Seq. ID Nr. 1, 2, 4 6 or 11-25 to at least 50%, preferably to at least 60%, particularly to at least 70%, to at least 80%, to at least 85%, to at least 86%, to at least 87%, to at least 88%, to at least 89%, to at least 90%, to at least 91%, to at least 92%, to at least 93%, to at least 94%, to at least 95%, to at least 96%, to at least 97%, to at least 98%, to at least 99%, or 100% and/or are homologous to at least 80%, to at least 85%, to at least 86%, to at least 87%, to at least 88% %, to at least 89%, to at least 90%, to at least 91%, to at least 92%, to at least 93%, to at least 94%, to at least 95%, to at least 96%, to at least 97%, to at least 98%, to at least 99% or 100%.

Those para-nitrobenzyl esterases are particularly preferred which are 95%, particularly preferably 98%, especially 100% identical with the listed amino acid sequences (1, 2, 4, 6, 11-25).

Those esterases are particularly preferred, which according to the methods 2.4 cited in the examples exhibit a specific activity towards the substrate bis-(p-methylbenzoic acid) ester of ethylene glycol of 0.1 to 30, preferably 0.6 to 20, particularly 0.7 to 15, quite particularly preferably 0.9 to 10, even more strongly preferably 1 to 5, particularly 1.1 to 4, quite particularly preferably 1.5 to 3 (μmol liberated acid)/ (min mg enzyme). These esterases have proved to be particularly advantageous for use in the inventive agents or uses and processes.

Those esterases are particularly preferred which are homologous to the protein sequences listed under Seq. ID Nr. 12 to at least 50%, at least 55%, particularly at least 60%, preferably at least 65%, particularly preferably at least 70%, advantageously at least 75%, quite particularly preferably at least 80%, particularly preferably at least 85%, at least 90%, at least 95%, at least 99%, especially 100%.

A further subject of the invention is the use of esterases, particularly esterases from Lipase P and p-nitrobenzyl esterases, for cleaving polyalkylene terephthalates, particularly polyethylene terephthalates (abb.: PET or PETE).

Likewise the esterases can be employed to cleave or degrade plastics, particularly polyesters and/or plasticizers in plastics. Phthalates are frequently used in plastics as plasticizers in order to improve the properties of the plastics during processing or use.

The invention relates to the partial or total degradation of molded objects, fabrics, coatings, adhesive bonds or foams made of enzymatically biologically degradable polymers. It particularly relates to the enzymatic degradation of polyesters. The polymer degradation process can be carried out in a variety of ways:

The polymer is added to the aqueous enzyme-containing solution. The biologically degradable polymer can be added as a film, sheet or pellet. Molded articles can be added whole or in small pieces. Coated or bonded materials or materials that were coated with biologically degradable polymers or produced with adhesives, such as for example paper or cardboard as well as coated paper or coated cardboard, can be added as is or in small pieces to the enzyme-containing solution.

In addition, the aqueous enzyme-containing solution can be coated or sprayed onto the coating or the molded article to be degraded.

The described process of enzymatic degradation of biological and enzymatically degradable polymers and blends produced thereof can be inventively employed for example to include chemicals, active substances, auxiliaries, enzymes, microorganisms, plant seeds in (e.g. capsules and microcapsules) and their targeted release by the addition of enzymes.

Thus, by the use of the inventive process, e.g. in garbage treatment installations, the environment can be more quickly rid of biologically and/or degradable polymers or their mixtures.

Those esterases are particularly preferred, which according to the methods 2.4 cited in the examples exhibit a specific activity towards the substrate bis-(p-methylbenzoic acid) ester of ethylene glycol of 0.1 to 30, preferably 0.6 to 20, particularly 0.7 to 15, quite particularly preferably 0.9 to 10, even more strongly preferably 1 to 5, particularly 1.1 to 4, quite particularly preferably 1.5 to 3 (μmol liberated acid)/ (min mg enzyme). These esterases have proved to be particularly advantageous for use in the inventive agents or uses and processes.

Those esterases are particularly preferred which are homologous to the protein sequences listed under Seq. ID Nr. 12 to at least 50%, at least 55%, particularly at least 60%, preferably at least 65%, particularly preferably at least 70%, advantageously at least 75%, quite particularly preferably at least 80%, particularly preferably at least 85%, at least 90%, at least 95%, at least 99%, especially 100%. Likewise, mutations of the enzyme listed under SEQ ID NO. 12 that exhibit a further improved inventive action are particularly preferred.

A further subject of the invention is inventively employable naturally formed esterases that are obtainable from supernatant cultures or after cell digestion.

The nucleotide sequence of the inventive novel esterases from *Bacillus subtilis* (17A1) is listed in the sequence protocol of the present application under SEQ ID NO. 3. It comprises 1470 bp. The derived amino acid sequence is listed in SEQ ID NO. 1. It includes 489 amino acids followed by a stop codon.

The nucleotide sequences of the inventive novel esterases from *Bacillus licheniformis* (19C5) are listed in the sequence protocol of the present application under SEQ ID NO. 4. They each comprise 1470 bp. The derived amino acid sequence is listed in SEQ ID NO. 2. It includes 489 amino acids followed by a stop codon.

Because of the recognizable agreements and the connections to the other cited esterases, the esterases are to be regarded as p-nitrobenzyl esterases.

Consequently, a subject of the present invention is any esterase with an amino acid sequence that is identical to at least 70% to the amino acid sequences listed in SEQ ID NO. 1, 2, 5 or 6.

Among those that are increasingly preferred are those whose amino acid sequence is at least 72%, 74%, 76%, 78%, 80%, 82%, 84%, 85%, 86%, 88%, 90%, 91%, 92%, 93%, 94%, 95%, 96%, 97%, 98%, 99% and 100% identical to the amino acid sequences listed in SEQ ID NO. 1, 2, 5 or 6, preferably 1 or 2. It is expected that their properties are increasingly similar to those found.

An embodiment of this inventive subject matter is each esterase that is derived from a nucleotide sequence that is at least 70% identical (assuming an identical codon usage) to one of the nucleotide sequences listed in SEQ ID NO. 3, 4, 7 or 8.

Among those that are increasingly preferred are those which derive from a nucleotide sequence that is at least 72%, 74%, 76%, 78%, 80%, 82%, 84%, 85%, 86%, 88%, 90%, 91%, 92%, 93%, 94%, 95%, 96%, 97%, 98%, 99% and 100% identical to the nucleotide sequence listed in SEQ ID NO. 3.

Among those that are also increasingly preferred are those which derive from a nucleotide sequence that is at least 72%, 74%, 76%, 78%, 80%, 82%, 84%, 85%, 86%, 88%, 90%, 91%, 92%, 93%, 94%, 95%, 96%, 97%, 98%, 99% and 100% identical to the nucleotide sequence listed in SEQ ID NO. 4.

It is therefore to be expected that these nucleic acids code for proteins whose properties are increasingly similar to those of the inventive esterases.

The most preferred embodiment of this inventive subject matter is each esterase whose amino acid sequence is altogether identical with the amino acid sequences listed in SEQ ID NO. 1, 2, 5 or 6 and/or whose amino acid sequence is altogether identical with one of the amino acid sequences derived from the nucleotide sequences listed in SEQ ID NO. 3, 4, 7 or 8.

The esterases that are newly discovered and provided by the present application from *Bacillus subtilis* or *licheniformis* are those of this type.

They are esterases that are not known in the prior art. They can be isolated, manufactured and applicable, as listed in the examples. They are further characterized in that when used in an appropriate agent, their activity approximates or even exceeds that of the enzymes established for this purpose.

For the development of industrial esterases that in particular are applicable in detergents, as a natural microbially formed enzyme it can serve as a starting point to be optimized for the desired application by means of mutagenetic methods that are known per se, for example point mutagenesis, fragmentation, deletion, insertion or fusion with other proteins or protein fragments or by other modifications. These types of optimizations can be for example adaptations to the effects of temperature, pH fluctuations, redox conditions and/or other influences that are relevant to the industrial field of use. An improved oxidation resistance, stability against denaturing agents or proteolytic degradation, against high temperatures, acidic or strongly alkaline conditions, a reduction in immunogenicity or allergenic activity for example are desired.

The mutagenesis processes involve one of the associated nucleotide sequences that are listed in SEQ ID NO. 3, 4, 7 or 8 or the sufficiently similar nucleotide sequences that are illustrated below as a separate inventive subject matter. Suitable molecular biological methods are described in the prior art, for example in pertinent handbooks such as that by Fritsch, Sambrook und Maniatis "Molecular cloning: a laboratory manual", Cold Spring Harbour Laboratory Press, New York, 1989.

Further embodiments of the present invention are all proteins or fragments derived from one of the above described, inventive esterases by fragmentation or deletion mutagenesis, with increasing preference for at least 25, 26, 28, 30, 32, 34, 36, 38, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 343 and 360 amino acids already located in the starting molecule connected at the beginning, internally or at the end of the starting amino acid sequence.

Here, it is increasingly preferred that each of those proteins or fragments derived by fragmentation or deletion mutagenesis are identical to the sequences listed in SEQ ID NO. 1, 2, 7 or 8 to at least 86%, 88%, 90%, 91%, 92%, 93%, 94%, 95%, 96%, 97%, 98%, 99% and to 100%.

"Inventive fragments" are understood to mean all proteins or peptides, which are smaller than those homologous proteins that correspond to those of SEQ ID NO. 1 or SEQ ID NO. 2, but which match them in the corresponding partial sequences. These fragments can be, for example single domains or fractions that do not match with the domains. Such fragments may be cheaper to manufacture, no longer possess certain possibly detrimental characteristics of the starting molecule, such as an activity-reducing regulation mechanism, or develop a more favorable activity profile. These types of protein fragments may also be manufactured by non-biosynthetic methods, for example chemically. The chemical synthesis is for example advantageous when chemical modifications have to be carried out subsequent to the synthesis.

The proteins that are also obtainable by deletion mutation are to be assigned to the fragments due to their fundamental similarity. Deletion mutagenesis is particularly helpful for removing inhibiting regions. Both a specialization as well as an enlargement of the application range of the protein can result from the deletions.

Proteins and signal peptides obtained from pre-proteins by cleavage of the N-terminal amino acids can also be considered as naturally formed fragments or deletion-mutated proteins. This type of cleavage mechanism can be used for example in order to provide specific cleavage points in recombinant proteins with the aid of certain sequence regions that are identified by signal peptidases. Thus activation and/or deactivation in vitro of inventive proteins can be effected. As an example may be cited the signal peptide according to Seq ID No 9 (MMRKKSFWLGMLTAFMLVFTMAFSDSASA).

Further embodiments of the present invention are all from an inventive esterase described above or from a corresponding fragment by insertion mutagenesis, by substitution mutagenesis and/or by fusion with at least one other protein or proteins derived from protein fragments.

Inventive chimeric proteins possess in the broadest sense an esterolytic activity. This can be performed or modified by a part of a molecule that derives from an inventive protein. The chimeric proteins can lie across their whole length as well as outside the above claimed region. The sense of such a fusion consists in, for example, providing or modifying a certain function or partial function with the help of the fused-on inventive protein part. It is irrelevant in the context of the present invention whether such a chimeric protein consists of a single polypeptide chain or a plurality of sub-units. The latter alternative can be effected for example posttranslationally or first after a purification step by means of a targeted proteolytic cleavage by breaking down a single chimeric polypeptide chain into several.

Therefore it is possible, for example to equip an inventive protein or fragment thereof through peptidic linkers or directly as the fusion protein with binding domains from other proteins, for example the cellulose binding domains, and thereby to more effectively design the hydrolysis of the substrate. Such a binding domain could also derive from an esterase, for example to strengthen the binding of the inventive protein to an esterase substrate. This increases the local esterase concentration and can be advantageous in specific applications, for example in the treatment of raw materials. Similarly, inventive proteins can also be linked for example with amylases or cellulases so as to execute a dual function.

The inventive proteins that can be obtained by insertion mutation are assigned to the inventive chimeric proteins due to their fundamental similarity. Substitution variations also belong here, i.e. those in which single regions of the molecule have been substituted with elements from other proteins.

The significance of insertion and substitution mutagenesis is as in hybrid formation, to combine individual properties, functions or partial functions of inventive proteins with those of other proteins. This also includes a shuffling or novel combination of partial sequences from various esterases over to obtained variants. In this way proteins can be obtained that beforehand had not yet been described. Such techniques enable drastic effects down to very subtle modulations in activity.

Preferably such mutations are carried out according to a statistical process, known to the person skilled in the art, classified as regional directed evolution, such as for example according to the StEP method, the random priming recombination, the DNA shuffling or recursive sequence recombination or the RACHITT method. Such processes are necessarily coupled with a selection or screening process subsequent to the mutagenesis and expression, so as to recognize variants having the desired properties. As these techniques apply to the DNA level, the starting point for the biotechnological production is made available with each of the associated newly produced genes.

Inversion mutagenesis, meaning a partial reversal of the sequence, can be regarded as a special form of both deletion as well as of insertion. Such variants can likewise be targeted or randomly produced.

Active molecules are preferred over inactives, as for example in particular the exercised esterolysis is important in the application fields listed below.

The above listed fragments also possess, in the broadest sense, an esterolytic activity, for example for complexing a substrate or for forming a structural element required for hydrolysis. They are preferred when they can be already considered for use for the hydrolysis of an ester bond, without the need for the presence of further esterase components. This relates to the activity that an esterase per se can execute; the possible simultaneously required presence of buffer substances etc. remains unaffected.

An interaction of different molecular parts for the hydrolysis naturally exists in deletion mutants rather than in fragments and ensues in particular in fusion proteins, quite particularly those that emanate from a shuffling of related proteins. Thus, in so far as an esterolytic function in the broadest sense is sustained, modified, specified or also first achieved, then the deletion variants and the fusion proteins are inventive proteins. Preferred representatives of this inventive subject are among those that are capable of hydrolyzing a substrate without the need for the presence of further esterase components.

A preferred embodiment is illustrated by all those proteins, protein fragments or fusion proteins that have been listed, which are characterized in that they are further derivatised.

Derivatives are understood to mean those proteins that are derived from the listed proteins by an additional modification. These types of modifications can influence for example the stability, substrate specificity or the binding strength to the substrate or the enzymatic activity. They can also serve to reduce the allergenicity and/or immunogenicity of the protein and thereby increase its skin compatibility, for example.

Such derivatizations can be effected biologically, for example by the produced host organism in connection with the protein biosynthesis. Here, couplings of low molecular weight compounds such as lipids or oligosaccharides are particularly emphasized.

However, derivatizations can also be effected chemically, for example by the chemical transformation of a side chain or by the covalent bonding of another, for example macromolecular compound onto the protein. For example, the coupling of amines on carboxylic groups of an enzyme is possible in order to change the isoelectric point. Macromolecules, such as proteins, for example can be bonded through e.g. bifunctional chemical compounds to inventive proteins. Thus it is possible for example to provide an inventive protein over a linker with a specific binding domain. These types of derivatives are particularly suitable for use in detergents or cleaning agents. In analogy with WO 00/01831, esterase inhibitors can also be bonded through linkers, especially amino acid linkers, to the inventive proteins. Couplings with other macromolecular compounds, such as polyethylene glycol, improve the molecule in regard to further properties, such as stability or skin compatibility.

In the broadest sense, derivatives of inventive proteins can also be understood to mean preparations of these enzymes. Depending on extraction, work up or preparation a protein can be blended with various other materials, for example from the cultures produced by microorganisms. Certain other materials can also be purposely added to a protein, for example to increase its storage stability. Therefore, all preparations of an inventive protein are also in accordance with the invention. This is also independent of whether this enzymatic activity is actually displayed by a specific preparation. It may be desired that it possesses no or only limited activity during storage, and first develops its esterolytic function at the time of use. This can be controlled for example by suitable accompanying substances.

A preferred embodiment is illustrated by all those proteins, protein fragments or fusion proteins that have been listed so far and which are characterized in that they are additionally stabilized.

In this way their stability during storage and/or during their use, for example during the washing process, is increased such that their activity lasts longer and is consequently boosted. Coupling to polymers, for example, can increase the stability of inventive esterases. This requires that prior to use in suitable agents, the proteins be bonded with such polymers by means of a coupling step.

Stabilizations that are possible by point mutagenesis of the molecule itself are preferred. No further process steps would then be required after having extracted the protein. Some point mutations that are suitable for this are known from the prior art.

Other possibilities are for example:
the exchange of proline for certain amino acid groups;
the introduction of polar or charged groups on the surface of the molecule;

Another possibility for stabilizing against increased temperature and the effect of surfactants can reside in stabilization by the exchange of amino acids in close proximity to the N-terminus with those that come into contact with the remainder of the molecule through non-covalent interactions and consequently contribute to maintaining the globular structure.

Preferred embodiments are those in which the molecule is stabilized by a plurality of methods. It can be assumed that several stabilizing mutations act additively.

A preferred embodiment is represented by all proteins, protein fragments, fusion proteins or derivatives, which are characterized in that they have at least one antigenic determinant in common with one of the above described inventive proteins, protein fragments, fusion proteins or derivatives.

The secondary structural elements of a protein and its three dimensional folding are decisive for the enzymatic activities. Thus, domains that significantly differ from each other in their primary structure can form spatially largely conformable structures and therefore make possible the same enzymatic behavior. Such commonalities in the secondary structure are usually identified as autologous antigenic determinants of antiserums or of pure or monoclonal antibodies. Similar proteins or derivatives can be detected and classified in this way by means of immunochemical cross reactions. Consequently such proteins that may possibly not be classified by their degree of homology in the primary structure but arguably by their immunochemical affinity to the above defined inventive proteins, protein fragments, fusion proteins or derivatives are also precisely included in the scope of protection of the present invention.

A preferred embodiment is illustrated by all those proteins, protein fragments, fusion proteins or derivatives that have been listed up to now, which are characterized in that they are obtained from a natural source, in particular from a microorganism.

For example they can be single cell fungi or bacteria. Mostly they can be more easily extracted and handled than the multicellular organisms or the cell cultures derived from metazoa; although these can represent reasonable options for specific embodiments and are thus not fundamentally excluded from the subject of the invention.

It is possible that naturally occurring products can indeed manufacture an inventive enzyme; however under the investigated conditions this only expresses to a limited extent and/or releases into the surrounding medium. However, this does not rule out suitable environmental conditions or other factors from being experimentally determined and that their application could stimulate a commercially reasonable production of the inventive protein. Such a regulation mechanism can be purposely employed for biotechnological production. If this is also not possible then they can still be used for isolating the associated gene.

Among these, those from gram-positive bacteria are particularly preferred. This is because they do not possess an external membrane and thus immediately release secreted proteins into the surrounding medium.

Those from gram-positive bacteria of the genus *Bacillus* are quite particularly preferred.

A priori, *bacillus* esterases possess favorable characteristics for various fields of application. They include a certain stability towards increased temperature, oxidizing or denaturing agents. In addition, most experience has been obtained with microbial enzymes in regard to their biotechnological production, for example concerning the construction of cost-effective cloning vectors, the selection of host cells and growth conditions or the estimation of risk, such as for example the allergenicity. Furthermore, bacilli are established as production organisms having a particularly high production performance in industrial processes. The wealth of experience acquired for the manufacture and use of these enzymes is of great benefit to the inventive further development of these enzymes. This concerns for example their compatibility with other chemical compounds, such as, for example, the ingredients of detergents or cleaning agents.

Among those of the *Bacillus* species, once again those from the species *Bacillus subtilis* or *licheniformis* are preferred.

The embodiments of the inventive enzymes were originally obtained from these. The associated sequences are given in the sequence transcript. The above described variants can be manufactured from them or related strains by the use of standard microbiological methods, such as, for example PCR and/or the known point mutagenesis methods.

The nucleic acids that serve to accomplish the invention represent a further solution to the problem of the invention and thereby a separate subject matter of the invention.

Nucleic acids form the starting point for virtually all molecular biological investigations and developments as well as the production of proteins. This includes in particular the gene sequencing and the deduction of the associated sequence of amino acids, each type of mutagenesis (see above) and the protein expression.

Mutagenesis for the development of proteins having defined characteristics is also called "protein engineering". Examples of characteristics that are optimized have already been described above. Such a mutagenesis can be targeted or carried out with random methods, for example with a screening and selection method directed to the final activity of the cloned genes, for example by hybridization with nucleic acid sensors, or on the gene products, the proteins, for example regarding their activity. Further development of the inventive esterases can be organized according to the considerations presented in the publication "Protein engineering" by P. N. Bryan (2000) in Biochim. Biophys. Acta, Volume 1543, pp. 203-222.

Consequently, a subject of the present invention is any nucleic acid coding for an esterase, whose nucleotide sequence is identical to at least 70% to the nucleotide sequences listed in SEQ ID NO. 3, 4, 7 or 8 (for comparable codon usage).

Among those that are increasingly preferred are those whose nucleotide sequence is at least 72%, 74%, 76%, 78%, 80%, 82%, 84%, 85%, 86%, 88%, 90%, 91%, 92%, 93%, 94%, 95%, 96%, 97%, 98%, 99% and 100% identical to the nucleotide sequences listed in SEQ ID NO. 3, 4, 7 or 8.

It is therefore to be expected that these nucleic acids code for proteins whose properties are increasingly similar to those of the esterases from *Bacillus*.

Additional representatives of this subject matter of the invention are all nucleic acids that code for one of the above described, inventive proteins, protein fragments, fusion products or derivatives.

The nucleic acids that code for the above described, preferred forms are correspondingly preferred, in particular also the nucleic acids obtained by mutagenesis.

The nucleic acids that code for protein fragments are especially explicitly included in the scope of protection of the present invention. For such oligonucleotides, all three reading frames have to be taken into account in both the sense as well as in the anti-sense direction. They can be used, particularly in the polymerase chain reaction (PCR), as the starting point for the synthesis of related nucleic acids, for example for the amplification of related genes from natural organisms. They can also serve for the production of chimerics by a PCR-based shuffling process. Other shuffling processes, such as for example the recombining ligation reaction (RLR) also involve oligonucleotides that correspond to randomly or targeted selected protein fragments. Anti-sense oligonucleotides can also be employed for expression regulation, for example.

In accordance with the abovementioned statements, the following are increasingly preferred among the above described inventive nucleic acids:

those that are obtained from a natural source, in particular from a microorganism;

among the above, those wherein the microorganism concerns a gram-positive bacterium;

among the above, those wherein the gram-positive bacterium concerns one of the genus *Bacillus*; and;

among the above, those wherein the genus *Bacillus* concerns a *Bacillus subtilis* or *licheniformis*.

A separate subject matter of the invention is formed by vectors that comprise one of the previously identified, inventive nucleic acid regions, especially one that codes for one of the previously identified proteins, protein fragments, fusion proteins or derivatives.

In order to deal with the relevant inventive nucleic acids, and therefore in particular to prepare the production of inventive proteins, said acids are suitably ligated in vectors. Such vectors and the associated working methods are extensively described in the prior art. A great number and a broad variation of vectors are commercially available, both for cloning as well as for expression. These include for example vectors that are derived from bacterial plasmids, bacteriophages or viruses, or predominantly synthetic vectors. Furthermore, they are differentiated according to the nature of the cell types, in which they are capable of establishing themselves, for example according to vectors for gram-negative, for gram-positive bacteria, for yeasts or for higher eukaryotes. The form suitable starting points for molecular biological and biochemical investigations, for example, as well as for the expression of the gene in question or associated proteins.

In one embodiment the inventive vectors concern cloning vectors.

In addition to the storage, the biological amplification or the selection of the gene of interest the cloning vectors are suitable for its molecular biological characterization. At the same time they represent transportable and storable forms of the claimed nucleic acids and are also starting points for molecular biological techniques that are not linked with cells, such as for example PCR or in vitro mutagenesis processes.

Preferably, the inventive vectors are expression vectors.

Such expression vectors are the basis for the realization of the corresponding nucleic acids in biological production systems and hence for the production of the associated proteins. Preferred embodiments of this subject matter of the invention are expression vectors that carry genetic elements required for expression, for example the natural localizing promoter originating before the gene or a promoter from another organism. These elements can be arranged in the form of a so called expression cassette, for example. Alternatively, individual or all regulation elements can also be prepared from the relevant host cell. The expression vectors are particularly preferably matched in regard to further characteristics, such as, for example the optimum copy number, the chosen expression system, especially the host cells (see below).

In addition, it is advantageous for a high expression rate if the expression vector comprises preferably only the gene in question as the insert and no larger 5'- or 3'-non coding regions. Such inserts are obtained for example if the fragment obtained after statistical treatment of the chromosomal DNA of the starting strain with a restriction enzyme after the sequencing has been purposely cut once more before the integration into the expression vector.

A separate subject matter of the invention is formed by cells that comprise one of the previously identified, inventive nucleic acid regions, especially one that codes for one of the previously identified inventive proteins, protein fragments, fusion proteins or derivatives, preferably on one of the previously identified, inventive vectors.

These cells comprise the genetic information for the synthesis of an inventive protein. They enable for example the amplification of the corresponding gene, but also its mutagenesis or transcription and translation and finally the biotechnological production of the protein in question. This genetic information can be integrated either extrachromosomally as the single genetic element, i.e. for bacteria present in the plasmidic localization or be integrated into a chromosome. The choice of a suitable system depends on the issues, such as for example the nature and period of storage of the gene, or of the organism or the nature of the mutagenesis or selection. Thus, in the prior art for example are described mutagenetic and selection methods based on bacteriophages—and their specific host cells—for the development of detergent enzymes.

Preferably this concerns host cells that express one of the previously described, inventive protein, protein fragments, fusion proteins or derivatives or can be stimulated to their expression, in particular by employing one of the previously identified, inventive nucleic acid regions, quite particularly by employing one of the previously identified expression vectors.

The host cells that form the proteins enable their biotechnological production. For this they must have received the gene in question, suitably with one of the previously described vectors and whose transcription must be capable of translation and preferably the possible additional modification steps.

In principle, all organisms, i.e. prokaryotes, eukaryotes or cyanophytae are suitable host cells for protein expression. Those host cells are preferred, which can be genetically handled with ease, for example in relation to the transformation with the expression factor and its stable establishment and the regulation of the expression, for example single cell fungi or bacteria. In addition, preferred host cells are those with a good microbiological and biotechnological handleability. For example this relates to ease of cultivation, high growth rates, low demands on fermentation media and good production rates and secretion rates for foreign proteins. Laboratory strains that are geared to expression are preferably selected. They are commercially available or can be obtained from generally accessible collections of strains. Theoretically, each inventive protein can be obtained in this way from a plurality of host organisms. The optimum expression system for the individual case must be experimentally determined from the abundance of different systems available from the prior art.

Host cells that are themselves esterase-negative are particularly advantageous.

Preferred embodiments are illustrated by such host cells that, due to suitable genetic elements, can be regulated in their activity, for example by the controlled addition of chemical compounds, by changing the conditions of cultivation or as a function of the respective cell density. This controllable expression enables a very cost effective production of the proteins of interest. Suitably the gene, expression vector and host cell are matched to one another, for example in regard to the genetic elements required for expression (ribosome binding points, promoters, terminators) or the codon usage. The codon usage for example can be optimized in that in the gene of those codons that are only poorly translated from the host in question, each of the same meaning are replaced by those that are more useful for the respective host.

Preferred among these are host cells that are characterized in that they are bacteria, in particular those that secrete the formed protein into the surrounding medium.

Bacteria are characterized by short generation times and low demands on the cultivation conditions. In this manner, cost effective processes can be established. Moreover, there exists an extensive wealth of experience with bacteria in fermentation technology. For a specific production in particular cases requiring factors such as nutrient sources, rates of product formation, time requirements etc., to be experimentally determined, the most varied gram-negative or gram positive bacteria can be suitable.

With gram-negative bacteria, such as *E. coli*, a plurality of proteins is secreted into the periplasmic space. This can be advantageous for specific applications. In contrast, gram-positive bacteria, such as for example Bacilli, immediately release secreted proteins into the nutrient medium surrounding the cells, from which medium, according to another preferred embodiment, the expressed inventive proteins can be directly purified.

A process is disclosed in the application WO 01/81597, wherein it is claimed that gram-negative bacteria also discharge the expressed proteins. Such a system is also suitable for manufacturing inventive proteins. Consequently, those of the species *Escherichia coli* or *Klebsiella* are preferred as host cells, particularly those of the strains *E. coli* JM 109, *E. coli* DH 100B, *E. coli* DH 12S or *Klebsiella planticola* (Rf). In order for the produced proteins to be released, suitable microbiological modifications and/or suitable vectors described in this application are required.

As host cells, preferred bacteria are those that are characterized in that they are gram-positive bacteria, in particular that they belong to the genus *Bacillus*, quite particularly to the species *Bacillus lentus, Bacillus licheniformis, Bacillus amyloliquefaciens, Bacillus subtilis* or *Bacillus alcalophilus*.

An embodiment of the present invention utilizes *B. licheniformis* or *B. subtilis* itself to (homologously) express inventive proteins. In contrast, however, the heterologous expression is preferred. For this, bacteria of the genus *Bacillus* are preferred because on production grounds they are the best characterized among the gram-positive bacteria. These particularly include those of the species *B. licheniformis, B. amyloliquefaciens, B. subtilis* or other species or strains of *B. alcalophilus*. With these species there exists pertinent experience concerning the enzyme manufacture. These related species additionally dispose of a similar codon usage, such that their protein synthesis apparatus is by nature suitably attuned.

A further advantage is that with this process a mixture of inventive proteins can be obtained with the enzymes that are endogenously formed from the host strains. This type of coexpression also emanates from the application WO 91/02792. When this is not required, the esterase genes that are naturally present in the host cell have to be permanently or temporarily inactivated (see above).

Further preferred are host cells that are characterized in that they are eukaryotic cells, in particular those that post-translationally modify the formed protein.

Examples of suitable eukaryots are fungi like actinomycetes or yeasts like *saccharomyces* or *kluyveromyces*, as well as thermophilic fungal expression systems. These are particularly suitable for the expression of temperature stable variants. Modifications that eukaryotic systems carry out, particularly in connection with the protein synthesis, include for example the binding of low molecular weight compounds such as membrane anchors or oligosaccharides. These types of oligosaccharide modifications can be desirable for lowering the allergenicity. A coexpression with the enzymes that are naturally formed from these types of cells, such as for example cellulases, can also be advantageous.

Processes for manufacturing an inventive protein represent an independent subject matter of the invention.

Accordingly, each process is claimed for manufacturing one of the above described, inventive protein, protein fragment, fusion protein or derivative by employing one of the above described, inventive nucleic acids and/or by employing one of the above described, inventive vectors and/or by employing one of the above described, inventive cells.

They include, for example, chemical synthesis processes that are particularly economically expedient for shorter fragments.

In contrast, however, all molecular biological, microbiological or biotechnological manufacturing processes that are established in the prior art and already discussed in detail above are preferred. Therefore for example, with the previously identified DNA- and amino acid sequences, such as, for example those that can be derived from the sequence transcript, preferably with those from SEQ ID NO. 1, 2, 5 and 6 themselves, corresponding oligonucleotides and oligopeptides up to the complete genes and proteins can be synthesized using known molecular biological methods.

Starting from the known esterase producing microorganisms, for example based on the example in the present application, one can identify and isolate additional natural producers of esterases, determine their esterase-gene- and/or amino acid sequences and correspondingly further develop the specifications made here. Such bacterial species can also be cultivated and employed for appropriate manufacturing processes. Analogously, new expression vectors can be developed. Embodiments of the present invention based on the associated nucleic acid sequences can also be cell-free expression systems, in which the protein biosynthesis is reconstructed in vitro. All of the elements listed above can also be combined in new processes to manufacture the inventively employable proteins. A plurality of possible combinations of process steps is conceivable for each inventive protein, such that optimum processes have to be experimentally determined for each practical single case.

A separate subject matter of the invention is represented by agents comprising one of the previously described, inventive proteins, protein fragments, fusion proteins or derivatives.

All types of agents, in particular mixtures, formulations, solutions etc., whose suitability is improved by the addition of one of the inventive proteins described above, are hereby included in the scope of protection of the present invention. Depending on the field of application, this can concern for example solid mixtures, for example powders with freeze dried or encapsulated proteins, or agents in gel or liquid form. Preferred compositions comprise for example buffer substances, stabilizers and/or reaction partners of the esterases and/or other ingredients that are synergistic with the esterases. Among these in particular are agents for the application areas listed further below. Additional application areas emerge from the prior art and are illustrated for example in the handbook "Industrial enyzmes and their applications" by H. Uhlig, Wiley-Verlag, New York, 1998.

Detergents or cleaning agents comprising one of the previously described, inventive proteins, protein fragments, fusion proteins or derivatives make up the preferred embodiment of the subject matter of this invention.

As is shown in the embodiments of the present application, it was surprisingly determined that the particularly preferred esterases from *Bacillus*, i.e. already the wild type enzyme stands out, in that when used in a suitable detergent or cleaning agent, it at least approximates or partially even surpasses the contributions to washing or cleaning performance of enzymes established for this purpose.

This embodiment of the invention also includes all the possible types of cleaning compositions—both concentrates and compositions to be used without dilution—for use on a commercial scale, in washing machines or in hand washing or cleaning. These include, for example, detergents for fabrics, carpets or natural fibers, for which the term "detergent" is used in the present invention. These also include, for example, dishwashing detergents for dishwashing machines or manual dishwashing detergents or cleaners for hard surfaces, such as metal, glass, china, ceramic, tiles, stone, painted surfaces, plastics, wood or leather, for which the term "cleaning agent" is used in the present invention. Any type of detergent or cleaning agent represents an embodiment of the present invention, providing it is enriched by an inventive protein, protein fragment, fusion protein or derivative.

Embodiments of the present invention include all types established by the prior art and/or all required usage forms of the inventive detergents or cleaning agents. These include for example solid, powdered, liquid, gel or pasty agents, optionally from a plurality of phases, compressed or non-compressed; further included are for example: extrudates, granulates, tablets or pouches, both in bulk and also packed in portions.

In a preferred embodiment, the inventive detergent or cleaning agents comprise the above described, inventive or inventively useable proteins, protein fragments, fusion proteins or derivatives in an amount of 0.0001 µg to 480 mg, preferably 0.005 µg to 420 mg, particularly preferably 0.02 µg to 360 mg, quite particularly preferably 0.05 µg to 240 mg per gram of the agent.

In addition to an inventive protein, protein fragment, fusion protein or derivative, an inventive detergent or cleaning agent optionally comprises further ingredients such as enzyme stabilizers, surfactants, e.g. non-ionic, anionic and/or amphoteric surfactants, and/or bleaching agents, and/or builders, as well as optional further usual ingredients, which are described below.

Preferred non-ionic surfactants are alkoxylated, advantageously ethoxylated, particularly primary alcohols preferably containing 8 to 18 carbon atoms and, on average, 1 to 12 moles of ethylene oxide (EO) per mole of alcohol, in which the alcohol group may be linear or, preferably, methyl-branched in the 2-position or may contain linear and methyl-branched groups in the form of the mixtures typically present in oxoalcohol groups. In particular, however, alcohol ethoxylates with linear alcohol groups of natural origin with 12 to 18 carbon atoms, e.g. from coco-, palm-, tallow- or oleyl alcohol, and an average of 2 to 8 EO per mole alcohol are preferred. Exemplary preferred ethoxylated alcohols include $C_{12-14}$ alcohols with 3 EO or 4EO, $C_{9-11}$ alcohols with 7 EO, $C_{13-15}$ alcohols with 3 EO, 5 EO, 7 EO or 8 EO, $C_{12-18}$ alcohols with 3 EO, 5 EO or 7 EO and mixtures thereof, as well as mixtures of $C_{12-14}$ alcohol with 3 EO and $C_{12-18}$ alcohol with 5 EO. The cited degrees of ethoxylation constitute statistically average values that can be a whole or a fractional number for a specific product. Preferred alcohol ethoxylates have a narrowed homolog distribution (narrow range ethoxylates, NRE). In addition to these non-ionic surfactants, fatty alcohols with more than 12 EO can also be used. Examples of these are tallow fatty alcohol with 14 EO, 25 EO, 30 EO or 40 EO.

Another class of preferred non-ionic surfactants which may be used, either as the sole non-ionic surfactant or in combination with other non-ionic surfactants are alkoxylated, preferably ethoxylated or ethoxylated and propoxylated fatty acid alkyl esters preferably containing 1 to 4 carbon atoms in the alkyl chain, in particular fatty acid methyl esters.

A further class of non-ionic surfactants, which can be advantageously used, are the alkyl polyglycosides (APG). Suitable alkyl polyglycosides satisfy the general Formula RO(G)z where R is a linear or branched, particularly 2-methyl-branched, saturated or unsaturated aliphatic group containing 8 to 22, preferably 12 to 18 carbon atoms and G is a symbol that stands for a glycose unit containing 5 or 6 carbon atoms, preferably for glucose. Here, the degree of glycosidation z is between 1.0 and 4.0, preferably between 1.0 and 2.0 and particularly between 1.1 and 1.4. Linear alkyl polyglucosides are preferably employed, that is alkyl polyglycosides, in which the polyglycosyl group is a glucose group and the alkyl group is an n-alkyl group.

Non-ionic surfactants of the amine oxide type, for example N-cocoalkyl-N,N-dimethylamine oxide and N-tallow alkyl-N,N-dihydroxyethylamine oxide, and the fatty acid alkanolamides may also be suitable. The quantity of these non-ionic surfactants is preferably no more than the quantity in which the ethoxylated fatty alcohols are used and, particularly no more than half that quantity.

Other suitable surfactants are polyhydroxyfatty acid amides corresponding to the Formula (II),

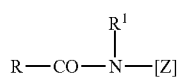

(II)

in which RCO stands for an aliphatic acyl group with 6 to 22 carbon atoms, $R^1$ for hydrogen, an alkyl or hydroxyalkyl group with 1 to 4 carbon atoms and [Z] for a linear or branched polyhydroxyalkyl group with 3 to 10 carbon atoms and 3 to 10 hydroxyl groups. The polyhydroxyfatty acid amides are known substances, which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to the Formula (III),

(III)

in which R is a linear or branched alkyl or alkenyl group containing 7 to 12 carbon atoms, $R^1$ is a linear, branched or cyclic alkyl group or an aryl group containing 2 to 8 carbon atoms and $R^2$ is a linear, branched or cyclic alkyl group or an aryl group or an oxyalkyl group containing 1 to 8 carbon atoms, $C_{1-4}$ alkyl or phenyl groups being preferred, and [Z] is a linear polyhydroxyalkyl group, of which the alkyl chain is substituted by at least two hydroxyl groups, or alkoxylated, preferably ethoxylated or propoxylated derivatives of that group.

[Z] is preferably obtained by reductive amination of a sugar, for example glucose, fructose, maltose, lactose, galactose, mannose or xylose. The N-alkoxy- or N-aryloxy-substituted compounds may then be converted into the required polyhydroxyfatty acid amides by reaction with fatty acid methyl esters in the presence of an alkoxide as catalyst.

Exemplary suitable anionic surfactants are those of the sulfonate and sulfate type. Suitable surfactants of the sulfonate type are, advantageously $C_{9-13}$ alkylbenzene sulfonates, olefin sulfonates, i.e. mixtures of alkene- and hydroxyalkane sulfonates, and disulfonates, as are obtained, for example, from $C_{12-18}$ monoolefins having a terminal or internal double bond, by sulfonation with gaseous sulfur trioxide and subsequent alkaline or acidic hydrolysis of the sulfonation products. Those alkane sulfonates, obtained from $C_{12-18}$ alkanes by sulfochlorination or sulfoxidation, for example, with subsequent hydrolysis or neutralization, are also suitable. The esters of α-sulfofatty acids (ester sulfonates), e.g. the α-sulfonated methyl esters of hydrogenated coco-, palm nut- or tallow acids are likewise suitable.

Further suitable anionic surfactants are sulfated fatty acid esters of glycerine. They include the mono-, di- and triesters and also mixtures of them, such as those obtained by the esterification of a monoglycerine with 1 to 3 moles fatty acid or the transesterification of triglycerides with 0.3 to 2 moles glycerine. Preferred sulfated fatty acid esters of glycerol in this case are the sulfated products of saturated fatty acids with 6 to 22 carbon atoms, for example caproic acid, caprylic acid, capric acid, myristic acid, lauric acid, palmitic acid, stearic acid or behenic acid.

Preferred alk(en)yl sulfates are the alkali metal and especially sodium salts of the sulfuric acid half-esters derived from the $C_{12}$-$C_{18}$ fatty alcohols, for example from coconut butter alcohol, tallow alcohol, lauryl, myristyl, cetyl or stearyl alcohol or from $C_{10}$-$C_{20}$ oxo alcohols and those half-esters of secondary alcohols of these chain lengths. Additionally preferred are alk(en)yl sulfates of the said chain lengths, which contain a synthetic, straight-chained alkyl group produced on a petrochemical basis and which show similar degradation behavior to the suitable compounds based on fat chemical raw materials. The $C_{12}$-$C_{16}$ alkyl sulfates and $C_{12}$-$C_{15}$ alkyl sulfates and $C_{14}$-$C_{15}$ alkyl sulfates are preferred on the grounds of laundry performance. 2,3-Alkyl sulfates are also suitable anionic surfactants.

Sulfuric acid mono-esters derived from straight-chain or branched $C_{7-21}$ alcohols ethoxylated with 1 to 6 moles ethylene oxide are also suitable, for example 2-methyl-branched $C_{9-11}$ alcohols with an average of 3.5 mole ethylene oxide (EO) or $C_{12-18}$ fatty alcohols with 1 to 4 EO. Due to their high foaming performance, they are only used in fairly small quantities in cleaning compositions, for example in amounts of up to 5% by weight, usually from 1 to 5% by weight.

Other suitable anionic surfactants are also the salts of alkyl-sulfosuccinic acid, which are also referred to as sulfosuccinates or esters of sulfosuccinic acid and the monoesters and/or di-esters of sulfosuccinic acid with alcohols, preferably fatty alcohols and especially ethoxylated fatty alcohols. Preferred sulfosuccinates comprise $C_{8-18}$ fatty alcohol groups or mixtures of them. Especially preferred sulfosuccinates comprise a fatty alcohol group derived from ethoxylated fatty alcohols and may be considered as non-ionic surfactants (see description above). Once again the especially preferred sulfosuccinates are those, whose fatty alcohol groups are derived from ethoxylated fatty alcohols with narrow range distribution. It is also possible to use alk(en)ylsuccinic acids with preferably 8 to 18 carbon atoms in the alk(en)yl chain, or salts thereof.

Soaps in particular can be considered as further anionic surfactants. Saturated fatty acid soaps are suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid.

Anionic surfactants, including soaps may be in the form of their sodium, potassium or ammonium salts or as soluble salts of organic bases, such as mono-, di- or triethanolamine. Preferably, the anionic surfactants are in the form of their sodium or potassium salts, especially in the form of the sodium salts.

The surfactants can be comprised in the inventive cleaning compositions or detergents in an amount of preferably 5 to 50 wt. %, particularly 8 to 30 wt. %, based on the finished composition.

The inventive detergents or cleaning agents can comprise bleaching agent. Among the compounds, which serve as bleaches and liberate $H_2O_2$ in water, sodium percarbonate, sodium perborate tetrahydrate and sodium perborate monohydrate are of particular importance. Examples of further bleaching agents, which may be used, are peroxypyrophosphates, citrate perhydrates and $H_2O_2$-liberating peracidic salts or peracids, such as persulfates or persulfuric acid. The urea peroxyhydrate percarbamide that can be described by the formula $H_2N$—$CO$—$NH_2 \cdot H_2O_2$ is also suitable. Particularly when agents are used to clean hard surfaces, for example in automatic dishwashers, they can, if desired, also comprise bleaching agents from the group of the organic bleaching agents, although in principal they can also be used for washing textiles. Typical organic bleaching agents are the diacyl peroxides, such as e.g. dibenzoyl peroxide. Further typical organic bleaching agents are the peroxy acids, wherein the alkylperoxy acids and the arylperoxy acids may be named as examples. Preferred representatives that can be added are peroxybenzoic acid and ring-substituted derivatives thereof, such as alkyl peroxybenzoic acids, but also peroxy-α-naphthoic acid and magnesium monoperphthalate, the aliphatic or substituted aliphatic peroxy acids, such as peroxylauric acid, peroxystearic acid, ε-phthalimidoperoxycaproic acid [phthaloiminoperoxyhexanoic acid, PAP)], o-carboxybenzamidoperoxycaproic acid, N-nonenylamido peradipic acid and N-nonenylamido persuccinates and aliphatic and araliphatic peroxydicarboxylic acids, such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyl-di(6-aminopercaproic acid).

The bleaching agent content of the detergent or cleaning agent is preferably 1 to 40 wt. % and particularly 10 to 20 wt. %, perborate monohydrate or percarbonate being advantageously used.

The preparations can also comprise bleach activators in order to achieve an improved bleaching action for washing temperatures of 60° C. and below and particularly during the pre-treatment wash. Bleach activators, which can be used are compounds which, under perhydrolysis conditions, yield aliphatic peroxycarboxylic acids having preferably 1 to 10 carbon atoms, in particular 2 to 4 carbon atoms, and/or optionally substituted perbenzoic acid. Substances, which carry O-acyl and/or N-acyl groups of said number of carbon atoms and/or optionally substituted benzoyl groups, are suitable. Preference is given to polyacylated alkylenediamines, in particular tetraacetyl ethylene diamine (TAED), acylated triazine derivatives, in particular 1,5-diacetyl-2,4-dioxohexahydro-1, 3,5-triazine (DADHT), acylated glycolurils, in particular tetraacetyl glycoluril (TAGU), N-acylimides, in particular N-nonanoyl succinimide (NOSI), acylated phenol sulfonates, in particular n-nonanoyl- or isononanoyloxybenzene sulfonate (n- or iso-NOBS), carboxylic acid anhydrides, in particular phthalic anhydride, acylated polyhydric alcohols, in particular triacetin, ethylene glycol diacetate and 2,5-diacetoxy-2,5-dihydrofuran and the enol esters known from the German Patent applications DE 196 16 693 and DE 196 16 767 and acetylated sorbitol and mannitol or their mixtures (SORMAN) described in the European Patent application EP-A-767 0 525, acylated sugar derivatives, in particular pentaacetylglucose (PAG), pentaacetylfructose, tetraacetylxylose and octaacetyllactose as well as acetylated, optionally N-alkylated glucamine and gluconolactone, triazole or triazole derivatives and/or particulate caprolactams and/or caprolactam derivatives, preferably N-acylated lactams, for example N-benzoylcaprolactam and N-acetylcaprolactam. Hydrophilically substituted acyl acetals and acyl lactams are also preferably used. Combinations of conventional bleach activators may also be used. Nitrile derivatives such as cyanopyridines, nitrilequats, for example N-alkyl ammonium acetonitrile, and/or cyanamide derivatives can also be used. Preferred bleach activators are sodium 4-(octanoyloxy)benzene sulfonate, n-nonanoyl- or isononanoyloxybenzene sulfonate (n- or iso-NOBS), undecenoyloxybenzene sulfonate (UDOBS), sodium dodecanoyloxybenzene sulfonate (DOBS), decanoyloxybenzoic acid (DOBA, OBC 10) and/or dodecanoyloxybenzene sulfonate (OBS 12), and N-methylmorpholinum acetonitrile (MMA). These types of bleach activators are comprised in the usual quantity range of 0.01 to 20 wt. %, preferably in amounts of 0.1 wt. % to 15 wt. %, particularly 1 wt. % to 10 wt. %, based on the total composition.

In addition to, or instead of the conventional bleach activators mentioned above, so-called bleach catalysts may also be incorporated. These substances are bleach-boosting transition metal salts or transition metal complexes such as, for example, manganese-, iron-, cobalt-, ruthenium- or molybdenum-salen or -carbonyl complexes. Manganese, iron, cobalt, ruthenium, molybdenum, titanium, vanadium and copper complexes with nitrogen-containing tripod ligands, as well as cobalt-, iron-, copper- and ruthenium-ammine complexes may also be employed as the bleach catalysts, wherein those compounds that are described in DE 197 09 284 A1 are preferably employed.

Generally, inventive detergents or cleaning agents comprise one or more builders, in particular zeolites, silicates, carbonates, organic cobuilders and—where there are no ecological grounds against their use—also phosphates. The last are particularly preferred builders employed in cleaning compositions for automatic dishwashers.

Suitable silicate builders are the crystalline, layered sodium silicates corresponding to the general formula NaMSi$_x$O$_{2x+1}$yH$_2$O, wherein M is sodium or hydrogen, x is a number from 1.6 to 4, preferably 1.9 to 4.0 and y is a number from 0 to 20, preferred values for x being 2, 3 or 4. These types of crystalline layered silicates are described, for example, in the patent literature. Preferred crystalline layered silicates of the given formula are those in which M stands for sodium and x assumes the values 2 or 3. Both β- and also δ-sodium disilicates Na$_2$Si$_2$O$_5$yH$_2$O are particularly preferred. These types of compounds are commercially available, for example, under the designation SKS® (Clariant). SKS-6® is mainly a δ-sodium disilicate with the formula Na$_2$Si$_2$O$_5$yH$_2$O and SKS-7® is mainly the β-sodium disilicate. On reaction with acids (e.g. citric acid or carbonic acid), δ-sodium silicate affords Kanemit NaHSi$_2$O$_5$yH$_2$O, commercially available under the trade names SKS-9® and SKS-10® (Clariant). It can also be advantageous to chemically modify these layered silicates. The alkalinity, for example, of the layered silicates can be suitably modified. In comparison with the 5-sodium disilicate, layered silicates, doped with phosphate or carbonate, exhibit a different crystal morphology, dissolve more rapidly and show an increased calcium binding ability. Thus, layered silicates of the general formula x Na$_2$O y SiO$_2$ z P$_2$O$_5$ in which the ratio x to y corresponds to a number 0.35 to 0.6, the ratio x to z a number from 1.75 to 1200 and the ratio y to z a number from 4 to 2800, are described in the patent application DE 196 01 063. The solubility of the layered silicates can also be increased by employing particularly finely dispersed layered silicates. Compounds of the crystalline layered silicates with other ingredients can also be used. Compounds with cellulose derivatives, which possess advantages in the disintegration action, and which are particularly used in detergent tablets, as well as compounds with polycarboxylates, for example citric acid or polymeric polycarboxylates, for example copolymers of acrylic acid can be particularly cited in this context.

Other useful builders are amorphous sodium silicates with a modulus (Na$_2$O:SiO$_2$ ratio) of 1:2 to 1:3.3, preferably 1:2 to 1:2.8 and more preferably 1:2 to 1:2.6, which dissolve with a delay and exhibit multiple wash cycle properties. The delay in dissolution compared with conventional amorphous sodium silicates can have been obtained in various ways, for example by surface treatment, compounding, compressing/compacting or by over-drying. In the context of this invention, the term "amorphous" also means "X-ray amorphous". In other words, the silicates do not produce any of the sharp X-ray reflections typical of crystalline substances, but at best one or more maxima of the scattered X-radiation, which have a width of several degrees of the diffraction angle. However, particularly good builder properties may even be achieved where the silicate particles produce indistinct or even sharp diffraction maxima in electron diffraction experiments. This is interpreted to mean that the products have microcrystalline regions between 10 and a few hundred nm in size, values of up to at most 50 nm and especially up to at most 20 nm being preferred. Compacted/densified amorphous silicates, compounded amorphous silicates and over dried X-ray-amorphous silicates are particularly preferred.

An optionally suitable fine crystalline, synthetic zeolite containing bound water, is preferably zeolite A and/or P. Zeolite MAP® (commercial product of the Crosfield company), is particularly preferred as the zeolite P. However, zeolite X and mixtures of A, X and/or P are also suitable. Commercially available and preferably used in the context of the present invention is, for example, also a co-crystallizate of zeolite X and zeolite A (ca. 80 wt. % zeolite X), which is marketed by CONDEA Augusta S.p.A. under the trade name VEGOBOND AX® and which can be described by the Formula

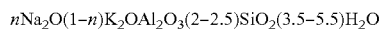

$n$Na$_2$O(1−$n$)K$_2$OAl$_2$O$_3$(2−2.5)SiO$_2$(3.5−5.5)H$_2$O

Suitable zeolites have an average particle size of less than 10 μm (test method: volumetric distribution Coulter counter) and preferably comprise 18 to 22 wt. %, particularly 20 to 22 wt. % of bound water.

Naturally, the generally known phosphates can also be added as builders, in so far that their use should not be avoided on ecological grounds. In the detergent and cleaning agent industry, among the many commercially available phosphates, the alkali metal phosphates are the most important and pentasodium or pentapotassium triphosphates (sodium or potassium tripolyphosphate) are particularly preferred.

"Alkali metal phosphates" is the collective term for the alkali metal (more particularly sodium and potassium) salts of the various phosphoric acids, in which metaphosphoric acids (HPO3)n and orthophosphoric acid (H3PO4) and representatives of higher molecular weight can be differentiated. The phosphates combine several inherent advantages: they act as alkalinity sources, prevent lime deposits on machine parts and lime incrustations in fabrics and, in addition, contribute towards the cleaning effect.

Sodium dihydrogen phosphate NaH$_2$PO$_4$ exists as the dihydrate (density 1.91 gcm-3, melting point 60° C.) and as the monohydrate (density 2.04 gcm-3). Both salts are white, readily water-soluble powders that on heating, lose the water of crystallization and at 200° C. are converted into the weakly acidic diphosphate (disodium hydrogen diphosphate, Na$_2$H$_2$P$_2$O$_7$) and, at higher temperatures into sodium trimetaphosphate (Na$_3$P$_3$O$_9$) and Maddrell's salt (see below). NaH$_2$PO$_4$ shows an acidic reaction. It is formed by adjusting phosphoric acid with sodium hydroxide to a pH value of 4.5 and spraying the resulting "mash". Potassium dihydrogen phosphate (primary or monobasic potassium phosphate, potassium biphosphate, KDP), KH$_2$PO$_4$, is a white salt with a density of 2.33 gcm-3, has a melting point of 253° C. [decomposition with formation of potassium polyphosphate (KPO$_3$)$_x$] and is readily soluble in water.

Disodium hydrogen phosphate (secondary sodium phosphate), Na$_2$HPO$_4$, is a colorless, very readily water-soluble crystalline salt. It exists in anhydrous form and with 2 mol (density 2.066 gcm-3, water loss at 95° C.), 7 mol (density 1.68 gcm-3, melting point 48° C. with loss of 5H$_2$O) and 12 mol of water (density 1.52 gcm-3, melting point 35° C. with loss of 5H$_2$O), becomes anhydrous at 100° C. and, on fairly intensive heating, is converted into the diphosphate Na$_4$P$_2$O$_7$. Disodium hydrogen phosphate is prepared by neutralization of phosphoric acid with soda solution using phenolphthalein as the indicator. Dipotassium hydrogen phosphate (secondary or dibasic potassium phosphate), K$_2$HPO$_4$, is an amorphous white salt, which is readily soluble in water.

Trisodium phosphate, tertiary sodium phosphate, Na$_3$PO$_4$, consists of colorless crystals that as the dodecahydrate have a density of 1.62 gcm-3 and a melting point of 73-76° C.

(decomposition), as the decahydrate (corresponding to 19-20% $P_2O_5$) a melting point of 100° C. and in anhydrous form (corresponding to 39-40% $P_2O_5$) a density of 2.536 gcm-3. Trisodium phosphate is readily soluble in water with an alkaline reaction and is manufactured by evaporating a solution of exactly 1 mole disodium phosphate and 1 mole NaOH. Tripotassium phosphate (tertiary or tribasic potassium phosphate), $K_3PO_4$, is a white deliquescent granular powder with a density of 2.56 gcm-3, has a melting point of 1340° C. and is readily soluble in water through an alkaline reaction. It is produced by e.g. heating Thomas slag with carbon and potassium sulfate. Despite their higher price, the more readily soluble and therefore highly effective potassium phosphates are often preferred to corresponding sodium compounds in the detergent industry.

Tetrasodium diphosphate (sodium pyrophosphate), $Na_4P_2O_7$, exists in anhydrous form (density 2.534 gcm-3, melting point 988° C., a figure of 880° C. has also been mentioned) and as the decahydrate (density 1.815-1.836 gcm-3, melting point 94° C. with loss of water). Both substances are colorless crystals that dissolve in water with an alkaline reaction. $Na_4P_2O_7$ is formed when disodium phosphate is heated to more than 200° C. or by reacting phosphoric acid with soda in a stoichiometric ratio and spray drying the solution. The decahydrate complexes heavy metal salts and hardness salts and, hence, reduces the hardness of water. Potassium diphosphate (potassium pyrophosphate), $K_4P_2O_7$, exists in the form of the trihydrate and is a colorless hygroscopic powder with a density of 2.33 gcm-3, which is soluble in water, the pH of a 1% solution at 25° C. being 10.4.

Relatively high molecular weight sodium and potassium phosphates are formed by condensation of $NaH_2PO_4$ or $KH_2PO_4$. They may be divided into cyclic types, namely the sodium and potassium metaphosphates, and chain types, the sodium and potassium polyphosphates. The chain types in particular are known by various different names: fused or calcined phosphates, Graham's salt, Kurrol's salt and Maddrell's salt. All higher sodium and potassium phosphates are known collectively as condensed phosphates.

The industrially important pentasodium triphosphate, $Na_5P_3O_{10}$ (sodium tripolyphosphate), is anhydrous or crystallizes with $6H_2O$ to a non-hygroscopic, white, water-soluble salt which has the general formula NaO—[P(O)(ONa)—O]n-Na where n=3. Around 17 g of the salt free from water of crystallization dissolve in 100 g of water at room temperature, around 20 g at 60° C. and around 32 g at 100° C. After heating the solution for 2 hours to 100° C., around 8% orthophosphate and 15% diphosphate are formed by hydrolysis. In the preparation of pentasodium triphosphate, phosphoric acid is reacted with soda solution or sodium hydroxide in a stoichiometric ratio and the solution is spray-dried. Similarly to Graham's salt and sodium diphosphate, pentasodium triphosphate solubilizes many insoluble metal compounds (including lime soaps, etc.). $K_5P_3O_{10}$ (potassium tripolyphosphate), is marketed for example in the form of a 50% by weight solution (>23% $P_2O_5$, 25% $K_2O$). The potassium polyphosphates are widely used in the detergent industry. Sodium potassium tripolyphosphates also exist and are also usable in the scope of the present invention. They are formed for example when sodium trimetaphosphate is hydrolyzed with KOH:

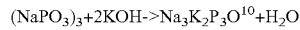

$(NaPO_3)_3 + 2KOH \rightarrow Na_3K_2P_3O^{10} + H_2O$

According to the invention, they may be used in exactly the same way as sodium tripolyphosphate, potassium tripolyphosphate or mixtures thereof. Mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate may also be used in accordance with the invention.

Organic co builders, which may be used in the detergents and cleaning agents according to the invention, include, in particular, polycarboxylates or polycarboxylic acids, polymeric polycarboxylates, polyaspartic acid, polyacetals, optionally oxidized dextrins, other organic co builders (see below) and phosphonates. These classes of substances are described below.

Useful organic builders are, for example, the polycarboxylic acids usable in the form of their sodium salts, polycarboxylic acids in this context being understood to be carboxylic acids that carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA), providing its use is not ecologically unsafe, and mixtures thereof. Preferred salts are the salts of polycarboxylic acids such as citric acid, adipic acid, succinic acid, glutaric acid, tartaric acid, sugar acids and mixtures thereof.

Acids per se can also be used. Besides their building effect, the acids also typically have the property of an acidifying component and, hence, also serve to establish a relatively low and mild pH in washing or cleaning agents, when the pH, which results from the mixture of other components, is not wanted. Acids that are system-compatible and environmentally compatible such as citric acid, acetic acid, tartaric acid, malic acid, glycolic acid, succinic acid, glutaric acid, adipic acid, gluconic acid and mixtures thereof are particularly mentioned in this regard. However, mineral acids, particularly sulfuric acid or bases, particularly ammonium or alkali metal hydroxides can also serve as pH regulators. These types of regulators are preferably comprised in the inventive agents in amounts of not more than 20 wt. %, particularly from 1.2 wt. % to 17 wt. %.

Other suitable builders are polymeric polycarboxylates, i.e. for example the alkali metal salts of polyacrylic or polymethacrylic acid, for example those with a relative molecular weight of 500 to 70 000 g/mol.

The molecular weights mentioned in this specification for polymeric polycarboxylates are weight-average molecular weights Mw of the particular acid form which, fundamentally, were determined by gel permeation chromatography (GPC), equipped with a UV detector. The measurement was carried out against an external polyacrylic acid standard, which provides realistic molecular weight values by virtue of its structural similarity to the polymers investigated. These values differ significantly from the molecular weights measured against polystyrene sulfonic acids as the standard. The molecular weights measured against polystyrene sulfonic acids are generally significantly higher than the molecular weights mentioned in this specification.

Particularly suitable polymers are polyacrylates, which preferably have a molecular weight of 2000 to 20 000 g/mol. By virtue of their superior solubility, preferred representatives of this group are the short-chain polyacrylates, which have molecular weights of 2000 to 10 000 g/mol and, more particularly, 3000 to 5000 g/mol.

Further suitable copolymeric polycarboxylates are particularly those of acrylic acid with methacrylic acid and of acrylic acid or methacrylic acid with maleic acid. Copolymers of acrylic acid with maleic acid, which comprise 50 to 90 wt. % acrylic acid and 50 to 10 wt. % maleic acid, have proven to be particularly suitable. Their relative molecular weight, based on free acids, generally ranges from 2 000 to 70 000 g/mol, preferably 20 000 to 50 000 g/mol and especially 30 000 to 40 000 g/mol. The (co)polymeric polycarboxylates can be used either as powders or as aqueous solutions. The (co)polymeric polycarboxylate content of the compositions is preferably from 0.5 to 20% by weight, in particular from 1 to 10% by weight.

In order to improve the water solubility, the polymers can also comprise allylsulfonic acids, such as for example, allyloxybenzene sulfonic acid and methallyl sulfonic acid as monomers.

Other particularly preferred polymers are biodegradable polymers of more than two different monomer units, for example those which contain salts of acrylic acid and maleic acid and vinyl alcohol or vinyl alcohol derivatives as monomers or those which contain salts of acrylic acid and 2-alkylallyl sulfonic acid and sugar derivatives as monomers.

Other preferred copolymers are those, which preferably contain acrolein and acrylic acid/acrylic acid salts or acrolein and vinyl acetate as monomers.

Similarly, other preferred builders are polymeric amino dicarboxylic acids, salts or precursors thereof. Polyaspartic acids or their salts and derivatives are particularly preferred.

Further preferred builders are polyacetals that can be obtained by treating dialdehydes with polyol carboxylic acids that possess 5 to 7 carbon atoms and at least 3 hydroxyl groups. Preferred polyacetals are obtained from dialdehydes like glyoxal, glutaraldehyde, terephthalaldehyde as well as their mixtures and from polycarboxylic acids like gluconic acid and/or glucoheptonic acid.

Further suitable organic builders are dextrins, for example oligomers or polymers of carbohydrates that can be obtained by the partial hydrolysis of starches. The hydrolysis can be carried out using typical processes, for example acidic or enzymatic catalyzed processes. The hydrolysis products preferably have average molecular weights in the range 400 to 500 000 g/mol. A polysaccharide with a dextrose equivalent (DE) of 0.5 to 40 and, more particularly, 2 to 30 is preferred, the DE being an accepted measure of the reducing effect of a polysaccharide by comparison with dextrose, which has a DE of 100. Both maltodextrins with a DE between 3 and 20 and dry glucose syrups with a DE between 20 and 37 and also so-called yellow dextrins and white dextrins with relatively high molecular weights of 2000 to 30 000 g/mol may be used.

The oxidized derivatives of such dextrins concern their reaction products with oxidizing agents that are capable of oxidizing at least one alcohol function of the saccharide ring to the carboxylic acid function. Particularly preferred organic builders for inventive agents are oxidized starches or their derivatives.

Oxydisuccinates and other derivatives of disuccinates, preferably ethylenediamine disuccinate are also further suitable cobuilders. Ethylenediamine-N,N'-disuccinate (EDDS) is preferably used here in the form of its sodium or magnesium salts. In this context, glycerine disuccinates and glycerine trisuccinates are also preferred. Suitable addition quantities in zeolite-containing and/or silicate-containing formulations range between 3 and 15% by weight.

Other useful organic co-builders are, for example, acetylated hydroxycarboxylic acids and salts thereof which may optionally be present in lactone form and which contain at least 4 carbon atoms, at least one hydroxy group and at most two acid groups.

The phosphonates represent a further class of substances with cobuilder properties. In particular, they are hydroxyalkane phosphonates or aminoalkane phosphonates. Among the hydroxyalkane phosphonates, 1-hydroxyethane-1,1-diphosphonate (HEDP) is of particular importance as the cobuilder. It is normally added as the sodium salt, the disodium salt reacting neutral and the tetrasodium salt reacting alkaline (pH 9). Ethylenediamine tetramethylene phosphonate (EDTMP), diethylenetriamine pentamethylene phosphonate (DTPMP) and their higher homologs are preferably chosen as the aminoalkane phosphonates. They are preferably added in the form of the neutral-reacting sodium salts, e.g. as the hexasodium salt of EDTMP or as the hepta and octasodium salt of DTPMP. Of the class of phosphonates, HEDP is preferably used as the builder. The aminoalkane phosphonates additionally possess a pronounced ability to complex heavy metals. Accordingly, it can be preferred, particularly where the agents also contain bleach, to use aminoalkane phosphonates, particularly DTPMP, or mixtures of the mentioned phosphonates.

In addition, any compounds capable of forming complexes with alkaline earth metal ions may be used as co-builders.

Builders can be comprised in the inventive detergents or cleaning agents optionally in quantities of up to 90% by weight. They are preferably comprised in quantities of up to 75% by weight. Inventive detergents possess builder contents of particularly 5 wt. % to 50 wt. %. In inventive compositions for cleaning hard surfaces, in particular for automatic dishwashing of tableware, the content of builders is particularly 5 wt. % to 88 wt. %, wherein in this type of composition, no water-insoluble builders are employed. In a preferred embodiment, the inventive agent, particularly for automatic dishwashing of tableware, comprises 20 wt. % to 40 wt. % of water-soluble organic builders, particularly alkali citrate, 5 wt. % to 15 wt. % alkali carbonate and 20 wt. % to 40 wt. % alkali disilicate.

Solvents that can be added to the liquid to gel-like compositions of detergents and cleaning agents originate, for example, from the group of mono- or polyhydric alcohols, alkanolamines or glycol ethers, in so far that they are miscible with water in the defined concentrations. Preferably, the solvents are selected from ethanol, n- or i-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl-, -ethyl- or -propyl ether, dipropylene glycol methyl-, or -ethyl ether, methoxy-, ethoxy- or butoxy triglycol, 1-butoxyethoxy-2-propanol, 3-methyl-3-methoxybutanol, propylene glycol t-butyl ether as well as mixtures of these solvents.

Solvents can be employed in the inventive liquid to gel-like detergents and cleaning compositions in amounts between 0.1 and 20 wt. %, preferably, however below 15 wt. % and particularly below 10 wt. %.

One or more thickeners or thickener systems can be added to the inventive compositions to adjust the viscosity. These high molecular weight substances, which are also called swelling agents, soak up mostly liquids, thereby swelling up and subsequently transform into viscous, real or colloidal solutions.

Suitable thickeners are inorganic or polymeric organic compounds. The inorganic thickeners include, for example, polysilicic acids, mineral clays like montmorillonite, zeolites, silicic acids and bentonites. The organic thickeners come from the groups of natural polymers, derivatives of natural polymers and synthetic polymers. Exemplary, naturally occurring polymers that can be used as thickeners are agar agar, carrageen, tragacanth, gum Arabic, alginates, pectins, polyoses, guar meal, locust tree bean flour, starches, dextrins, gelatines and casein. Modified natural products that are used as thickeners are mainly derived from the group of the modified starches and celluloses. Examples can be cited as carboxymethyl cellulose and other cellulose ethers, hydroxyethyl- and hydroxypropyl cellulose as well as flour ether. Totally synthetic thickeners are polymers such as polyacrylics and polymethacrylics, vinyl polymers, polycarboxylic acids, polyethers, polyimines, polyamides and polyurethanes.

The thickeners can be comprised in amounts up to 5 wt. %, preferably from 0.05 to 2 wt. %, and particularly preferably from 0.1 to 1.5 wt. %, based on the finished preparation.

The detergents or cleaning agents according to the invention can optionally comprise further typical ingredients—sequestering agents, electrolytes and further auxiliaries, such as optical brighteners, redeposition inhibitors, silver corrosion inhibitors, color transfer inhibitors, foam inhibitors, abrasives, dyes and/or fragrances, as well as antimicrobial agents UV absorbers and/or enzyme stabilizers.

The detergents for textiles may contain derivatives of diaminostilbene disulfonic acid or alkali metal salts thereof as optical brighteners. Suitable optical brighteners are, for example, salts of 4,4'-bis-(2-anilino-4-morpholino-1,3,5-triazinyl-6-amino)stilbene-2,2'-disulfonic acid or compounds of similar structure which contain a diethanolamino group, a methylamino group and anilino group or a 2-methoxyethylamino group instead of the morpholino group. Optical brighteners of the substituted diphenylstyryl type may also be present, for example the alkali metal salts of 4,4'-bis(2-sulfostyryl)diphenyl, 4,4'-bis(4-chloro-3-sulfostyryl)di phenyl or 4-(4-chlorostyryl)-4'-(2-sulfostyryl)diphenyl. Mixtures of the mentioned optical brighteners may also be used.

Graying inhibitors have the task of ensuring that the dirt removed from the textile fibers is held suspended in the wash liquid. Water-soluble colloids of mostly organic nature are suitable for this, for example starch, glue, gelatines, salts of ether carboxylic acids or ether sulfonic acids of starches or celluloses, or salts of acidic sulfuric acid esters of celluloses or starches. Water-soluble, acid group-containing polyamides are also suitable for this purpose. Moreover, aldehyde starches, for example, can be used instead of the abovementioned starch derivatives. Preference, however, is given to the use of cellulose ethers such as carboxymethyl cellulose (Na salt), methyl cellulose, hydroxyalkyl cellulose, and mixed ethers such as methyl hydroxyethyl cellulose, methyl hydroxypropyl cellulose, methyl carboxymethyl cellulose and mixtures thereof, which can be added, for example in amounts of 0.1 to 5 wt. %, based on the agent.

In order to realize a silver corrosion protection, silver protectors for tableware can be added to the inventive cleaning agents. Benzotriazoles, ferric chloride or CoSO4, for example are known from the prior art. As is known from the European Patent EP 0 736 084 B1, for example, particularly suitable silver corrosion inhibitors for general use with enzymes are salts and/or complexes of manganese, titanium, zirconium, hafnium, vanadium, cobalt or cerium, in which the cited metals exist in the valence states II, III, IV, V or VI. Examples of these types of compounds are $MnSO_4$, $V_2O_5$, $V_2O_4$, VO2, $TiOSO_4$, $K_2TiF_6$, $K_2ZrF_6$, $Co(NO_3)_2$, $Co(NO_3)_3$ and mixtures thereof.

Soil repellents are mostly polymers that when used in a detergent, lend the fibers soil repelling properties and/or support the soil repellent capabilities of the conventional ingredients. A comparable effect can also be observed when they are added in cleaning compositions for hard surfaces.

Particularly effective and well-known soil release agents are copolyesters with dicarboxylic acid, alkylene glycol and polyalkylene glycol units. Examples of these are copolymers or mixed polymers of polyethylene terephthalates and polyoxyethylene glycol (DT 16 17 141 and DT 22 00 911). German Offenlegungsschrift DT 22 53 063 cites acidic compositions, which inter alia comprise a copolymer of a dibasic acid and an alkylene or cycloalkylene polyglycol. Polymers of ethylene terephthalate and polyethylene oxide-terephthalate and their use in detergents are described in the prior art, likewise agents that comprise a copolyester of ethylene glycol, polyethylene glycol, aromatic dicarboxylic acids and sulfonated aromatic dicarboxylic acids in defined molar ratios. Methyl or ethyl group end blocked polyesters with ethylene and or propylene terephthalate and polyethylene oxide terephthalate units, and detergents that comprise this type of soil release polymer are known, as is polyester that in addition to oxyethylene groups and terephthalic acid units also comprises substituted ethylene units as well as glycerine units, and polyesters that in addition to oxyethylene groups and terephthalic acid units comprise 2-propylene-, 1,2-butylene- and/or 3-methoxy-1,2-propylene groups as well as glycerine units, and whose end groups are blocked with $C_1$ to $C_4$ alkyl groups. At least partially $C_{1-4}$ alkyl- or acyl end blocked polyesters containing polypropylene terephthalate and polyoxyethylene terephthalate units, sulfoethyl end blocked terephthalate-containing soil release polyester, sulfonated unsaturated end group soil release polyesters containing terephthalate, alkylene glycol and poly $C_2$-$C_4$ glycol units and acidic aromatic soil release polyesters are known. In addition, non-polymeric soil repellents for materials made of cotton are known with a plurality of functional units: a first unit, which can be cationic, for example, is able to be adsorbed onto the cotton surface by electrostatic attraction, and a second unit, which is designed to be hydrophobic, is responsible for the retention of the active agent at the water/cotton interface.

Color transfer inhibitors that can be used in inventive detergents for textiles particularly include polyvinyl pyrrolidones, polyvinyl imidazoles, polymeric N-oxides, such as polyvinyl pyridine-N-oxide, and copolymers of vinyl pyrrolidone with vinyl imidazole.

On using the agents in automatic cleaning processes, it can be advantageous to add foam inhibitors. Suitable foam inhibitors include for example, soaps of natural or synthetic origin, which have a high content of $C_{18}$-$C_{24}$ fatty acids. Suitable non-surface-active types of foam inhibitors are, for example, organopolysiloxanes and mixtures thereof with microfine, optionally silanized silica and also paraffins, waxes, microcrystalline waxes and mixtures thereof with silanized silica or bis-stearyl ethylene diamide. Mixtures of various foam inhibitors, for example mixtures of silicones, paraffins or waxes, are also used with advantage. Preferably, the foam inhibitors, especially silicone-containing and/or paraffin-containing foam inhibitors, are loaded onto a granular, water-soluble or dispersible carrier material. Especially in this case, mixtures of paraffins and bis stearylethylene diamides are preferred.

In processes for cleaning textiles or hard surfaces, the esterases are employed in a quantity of 0.04 μg to 96 g, preferably from 0.05 μg to 72 g, particularly preferably from 1 μg to 48 g and quite particularly preferably from 2 μg to 24 g per application.

An inventive cleaning composition for hard surfaces can moreover comprise abrasive ingredients, especially from the group comprising quartz meal, wood flour, plastic powder, chalk and microspheres as well as their mixtures. Abrasives are preferably comprised in the inventive cleaning compositions in amounts of not more than 20 wt. %, particularly from 5 wt. % to 15 wt. %.

Colorants and fragrances may be added to the detergents and cleaning agents in order to improve the esthetic impression created by the products and to provide the consumer not only with the required performance but also with a visually and sensorially "typical and unmistakable" product. Suitable perfume oils or fragrances include individual perfume compounds, for example synthetic products of the ester, ether, aldehyde, ketone, alcohol and hydrocarbon type. Perfume compounds of the ester type are, for example, benzyl acetate, phenoxyethyl isobutyrate, p-tert.-butylcyclohexyl acetate, linalyl acetate, dimethylbenzyl carbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals containing 8 to 18 carbon atoms, citral, citronellal, citronellyloxyacetaldehyde, cyclamen aldehyde, hydroxycitronellal, lilial and bourgeonal; the ketones include, for example, the ionones, α-isomethyl ionone and methyl cedryl ketone; the alcohols include anethol, citronellol, eugenol, geraniol, linalool, phenylethyl alcohol and terpineol and the hydrocarbons include, above all, the terpenes, such as limonene and pinene. However, mixtures of various odoriferous substances, which together produce an attractive fragrant note, are preferably used. Perfume oils such as these may also contain natural odoriferous mixtures obtainable from vegetal sources, for example pine, citrus, jasmine, patchouli, rose or ylang-ylang oil. Also suitable are muscatel oil, oil of sage, chamomile oil, clove oil, melissa oil, mint oil, cinnamon leaf oil, lime blossom oil, juniper berry oil, vetivert oil, olibanum oil, galbanum oil and laudanum oil and orange blossom oil, neroli oil, orange peel oil and sandalwood oil. Normally the content of dyes lies below 0.01 wt. %, while fragrances can make up to 2 wt. % of the total formulation of the detergents and cleaning composition.

The fragrances may be directly incorporated in the detergent or cleaning agent, although it can also be of advantage to apply the fragrances on carriers, which reinforce the adsorption of the perfume on the washing and thereby ensuring a long-lasting fragrance on the textiles by decreasing the release of the fragrance, especially for treated textiles. Suitable carrier materials are, for example, cyclodextrins, the cyclodextrin/perfume complexes optionally being coated with other auxiliaries. A further preferred carrier for fragrances is the described zeolite X, which instead of or in mixtures with surfactants can also take up fragrances. Accordingly, preferred detergents and cleaning agents comprise the described zeolite X and fragrances that are preferably at least partially absorbed on the zeolite.

Preferred colorants, which are not difficult for the expert to choose, have high storage stability, are not affected by the other ingredients of the detergents or by light and do not have any pronounced substantivity for the textile fibers being treated, so as not to color them.

To control microorganisms, the washing or cleaning agents may contain antimicrobial agents. Depending on the antimicrobial spectrum and the action mechanism, antimicrobial agents are classified as bacteriostatic agents and bactericides, fungistatic agents and fungicides, etc. Important substances from these groups are for example benzalkonium chlorides, alkylaryl sulfonates, halophenols and phenol mercury acetate. In the context of the inventive teaching, the expressions "antimicrobial activity" and "antimicrobial agent" have the usual technical meanings as defined, for example, by K. H. Wallhäußer in "Praxis der Sterilisation, Desinfektion-Konservierung Keimidentifizierung-Betriebshygiene" (5th Edition, Stuttgart/New York: Thieme, 1995), any of the substances with antimicrobial activity described therein being usable. Suitable antimicrobials are preferably selected from the group of the alcohols, amines, aldehydes, antimicrobial acids or their salts, esters of carboxylic acid, acid amides, phenols, phenol derivatives, diphenyls, diphenylalkanes, urea derivatives, oxygen, nitrogen acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propyl butyl carbamate, iodine, iodine-polymer complexes, iodophores, peroxy compounds, halogen compounds and mixtures of any of the above.

Consequently, the antimicrobial active substances can be chosen among ethanol, n-propanol, i-propanol, 1,3-butanediol, phenoxyethanol, 1,2-propylenelycol, glycerin, undecylenic acid, benzoic acid, salicylic acid, dihydracetic acid, o-phenylphenol, N-methylmorpholine-acetonitrile (MMA), 2-benzyl-4-chlorophenol, 2,2'-methylene-bis-(6-bromo-4-chlorophenol), 4,4'-dichloro-2'-hydroxydiphenyl ether (dichlosan), 2,4,4'-trichloro-2'-hydroxydiphenyl ether (trichlosan), chlorhexidine, N-(4-chlorophenyl)-N-(3,4-dichlorophenyl)-urea, N,N'-(1,10-decanediyldi-1-pyridinyl-4-ylidene)-bis-(1-octamine) dihydrochloride, N,N'-bis-(4-chlorophenyl)-3,12-diimino-2,4,11,13-tetraazatetradecanediimideamide, glucoprotamines, surface-active antimicrobial quaternary compounds, guanidines, including the bi- and polyguanidines, such as for example 1,6-bis(2-ethylhexylbiguanidohexane) dihydrochloride, 1,6-di-($N_1$, $N_1$'-phenyldiguanido-$N_5$,$N_5$')hexane tetrahydrochloride, 1,6-di-($N_1$,$N_1$'-phenyl-$N_1$,$N_1$'-methyldiguanido-$N_5$,$N_5$')hexane dihydrochloride, 1,6-di-($N_1$,$N_1$'-β-chlorophenyldiguanido-$N_5$, $N_5$')hexane dihydrochloride, 1,6-di-($N_1$,$N_1$'-2,6-dichlorophenyldiguanido-$N_5$,$N_5$')hexane dihydrochloride, 1,6-di-[$N_1$, $N_1$'-β-(p-methoxyphenyl)diguanido-$N_5$,$N_5$')hexane dihydrochloride, 1,6-di-($N_1$,$N_1$'-α-methyl-β-phenyl-diguanido-$N_5$,$N_5$')hexane dihydrochloride, 1,6-di-($N_1$,$N_1$'-p-nitrophenyldiguanido-$N_5$,$N_5$')hexane dihydrochloride, ω:ω-di-($N_1$,$N_1$'-phenyldiguanido-$N_5$,$N_5$')di-n-propyl ether dihydrochloride, ω:ω-di-($N_1$,$N_1$'-p-chlorophenyldiguanido-$N_5$,$N_5$')di-n-propyl ether tetrahydrochloride, 1,6-di-($N_1$,$N_1$'-2,4-dichlorophenyldiguanido-$N_5$,$N_5$')hexane tetrahydrochloride, 1,6-di-($N_1$,$N_1$'-p-methylphenyldiguanido-$N_5$,$N_5$') hexane dihydrochloride, 1,6-di-($N_1$,$N_1$'-2,4,5-trichlorophenyldiguanido-$N_5$,$N_5$')hexane tetrahydrochloride, 1,6-di-[$N_1$, $N_1$'-α-(p-chlorophenyl)ethyl-diguanido-$N_5$,$N_5$']hexane dihydrochloride, ω:ω-di-($N_1$,$N_1$'-p-chlorophenyldiguanido-$N_5$,$N_5$')m-xylene dihydrochloride, 1,12-di-($N_1$,$N_1$'-p-chlorophenyldiguanido-$N_5$,$N_5$')dodecane dihydrochloride, 1,10-di-($N_1$,$N_1$'-phenyldiguanido-$N_5$,$N_5$') decane tetrahydrochloride, 1,12-di-($N_1$,$N_1$'-phenyl-diguanido-$N_5$,$N_5$')dodecane tetrahydrochloride, 1,6-di-($N_1$, $N_1$'-o-chlorophenyldiguanido-$N_5$,$N_5$')hexane dihydrochloride, 1,6-di-($N_1$,$N_1$'-o-chlorophenyldiguanido-$N_5$,$N_5$')hexane tetrahydrochloride, ethylene-bis-(1-tolylphenyl biguanide), ethylene-bis-(p-tolylphenylbiguanide), ethylene-bis-(3,5-dimethylphenylbiguanide), ethylene-bis-(p-tert-amylphenylbiguanide), ethylene-bis-(nonylphenylbiguanide), ethylene-bis-(phenylbiguanide), ethylene-bis-(N-butylphenylbiguanide), ethylene-bis-(2,5-diethoxyphenylbiguanide), ethylene-bis-(2,4-dimethylphenylbiguanide), ethylene-bis-(o-diphenylbiguanide), ethylene-bis-(mixed amylnaphthylbiguanide), N-butylethylene-bis-(phenylbiguanide), trimethylene bis(o-tolylbiguanide), N-butyltrimethylene-bis-(phenylbiguanide) and the corresponding salts like acetates, gluconates, hydrochlorides, hydrobromides, citrates, bisulfites, fluorides, polymaleates, N-coco alkyl sarcinosates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates as well as any mixtures thereof. Furthermore, halogenated xylene- and cresol derivatives are suitable, such as p-chloro-meta-cresol, p-chloro-meta-xylene, as well as natural antimicrobial active agents of plant origin (e.g. from spices or aromatics), animal as well as microbial origin. Preferred antimicrobial agents are antimicrobial surface-active quaternary compounds, a natural antimicrobial agent of vegetal origin and/or a natural antimicrobial agent of animal origin and, most preferably, at least one natural antimicrobial agent of vegetal origin from the group comprising caffeine, theobromine and theophylline and essential oils, such as eugenol, thymol and geraniol, and/or at least one natural antimicrobial agent of animal origin from the group comprising enzymes, such as protein from milk, lysozyme and lactoperoxidase and/or at least one antimicrobial surface-active quaternary compound containing an ammonium, sulfonium, phosphonium, iodonium or arsonium group, peroxy compounds and chlorine compounds. Substances of microbial origin, so-called bacteriozines, may also be used.

The quaternary ammonium compounds (QUATS) suitable as antimicrobial agents have the general formula $(R^1)(R^2)(R^3)(R^4)N+X-$, in which $R^1$ to $R^4$ may be the same or different and represent $C_{1-22}$ alkyl groups, $C_{7-28}$ aralkyl groups or heterocyclic groups, two or—in the case of an aromatic compound, such as pyridine—even three groups together with the nitrogen atom forming the heterocycle, for example a pyridinium or imidazolinium compound, and X- represents halide ions, sulfate ions, hydroxide ions or similar anions. In the interests of optimal antimicrobial activity, at least one of the substituents preferably has a chain length of 8 to 18 and, more preferably, 12 to 16 carbon atoms.

QUATS can be obtained by reacting tertiary amines with alkylating agents such as, for example, methyl chloride, benzyl chloride, dimethyl sulfate, dodecyl bromide and also ethylene oxide. The alkylation of tertiary amines having one long alkyl chain and two methyl groups is particularly easy. The quaternization of tertiary amines containing two long chains and one methyl group can also be carried out under mild conditions using methyl chloride. Amines containing three long alkyl chains or hydroxy-substituted alkyl chains lack reactivity and are preferably quaternized with dimethyl sulfate.

Suitable QUATS are, for example, Benzalkonium chloride (N-alkyl-N,N-dimethylbenzyl ammonium chloride, CAS No. 8001-54-5), Benzalkon B (m,p-dichlorobenzyl dimethyl-C1-2-alkyl ammonium chloride, CAS No. 58390-78-6), Benzoxonium chloride (benzyldodecyl-bis-(2-hydroxyethyl) ammonium chloride), Cetrimonium bromide (N-hexadecyl-N,N-trimethyl ammonium bromide, CAS No. 57-09-0), Benzetonium chloride (N,N-di-methyl-N-[2-[2-[p-(1,1,3,3-tetramethylbutyl)-phenoxy]-ethoxy]-ethyl]-benzyl ammonium chloride, (CAS No. 121-54-0), dialkyl dimethyl ammonium chlorides, such as di-n-decyldimethyl ammonium chloride (CAS No. 7173-51-5-5), didecyldimethyl ammonium bromide (CAS No. 2390-68-3), dioctyl dimethyl ammonium chloride, 1-cetylpyridinium chloride (CAS No. 123-03-5) and thiazoline iodide (CAS No. 15764-48-1) and mixtures thereof. Particularly preferred QUATS are the benzalkonium chlorides containing $C_{8-18}$ alkyl groups, more particularly $C_{12}$-$C_{14}$ alkyl benzyl dimethyl ammonium chloride.

Benzalkonium halides and/or substituted benzalkonium halides are commercially available, for example, as Barquat® from Lonza, Marquato® from Mason, Variquat® from Witco/Sherex and Hyamine® from Lonza and as Bardac® from Lonza. Other commercially obtainable antimicrobial agents are N-(3-chloroallyl)-hexaminium chloride, such as Dowicide® and Dowicil® from Dow, benzethonium chloride, such as Hyamine® 1622 from Rohm & Haas, methyl benzethonium chloride, such as Hyamine® 10× from Rohm & Haas, cetyl pyridinium chloride, such as cepacolchloride from Merrell Labs.

The antimicrobial agents are used in quantities of 0.0001% by weight to 1% by weight, preferably 0.001% by weight to 0.8% by weight, particularly preferably 0.005% by weight to 0.3% by weight and most preferably 0.01 to 0.2% by weight.

The inventive detergents or cleaning agents may comprise UV absorbers that attach to the treated textiles and improve the light stability of the fibers and/or the light stability of the various ingredients of the formulation. UV-absorbers are understood to mean organic compounds, which are able to absorb UV radiation and emit the resulting energy in the form of longer wavelength radiation, for example as heat.

Compounds, which possess these desired properties, are for example, the efficient radiationless deactivating compounds and derivatives of benzophenone having substituents in position(s) 2- and/or 4. Also suitable are substituted benzotriazoles, acrylates, which are phenyl-substituted in position 3 (cinnamic acid derivatives optionally with cyano groups in position 2), salicylates, organic Ni complexes, as well as natural substances such as umbelliferone and the endogenous urocanic acid. The biphenyl and above all the stilbene derivatives such as for example those described in EP 0 728 749 A and commercially available as Tinosorb® FD or Tinosorb® FR from Ciba, are of particular importance. As UV-B absorbers can be cited: 3-benzylidenecamphor or 3-benzylidenenorcamphor and its derivatives, for example 3-(4-methylbenzylidene) camphor, as described in the EP 0693471 B1; 4-aminobenzoic acid derivatives, preferably 4-(dimethylamino)benzoic acid, 2-ethylhexyl ester, 4-(dimethylamino)benzoic acid, 2-octyl ester and 4-(dimethylamino)benzoic acid, amyl ester; esters of cinnamic acid, preferably 4-methoxycinnamic acid, 2-ethylhexyl ester, 4-methoxycinnamic acid, propyl ester, 4-methoxycinnamic acid, isoamyl ester, 2-cyano-3,3-phenylcinnamic acid, 2-ethylhexyl ester (octocrylene); esters of salicylic acid, preferably salicylic acid, 2-ethylhexyl ester, salicylic acid, 4-isopropylbenzyl ester, salicylic acid, homomethyl ester; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably 4-methoxybenzmalonic acid, di-2-ethylhexylester; triazine derivatives, such as, for example 2,4,6-trianilino-(p-carbo-2'-ethyl-1'-hexyloxy)-1,3,5-triazine and octyl triazone, as described in EP 0818450 A1 or dioctyl butamidotriazone (Uvasorb® HEB); propane-1,3-dione, such as for example 1-(4-tert.-butylphenyl)-3-(4'-methoxyphenyl)propane-1,3-dione; ketotricyclo(5.2.1.0) decane derivatives, as described in EP 0694521 B1. Further suitable are 2-phenylbenzimidazole-5-sulfonic acid and its alkali-, alkaline earth-, ammonium-, alkylammonium-, alkanolammonium- and glucammonium salts; sulfonic acid derivatives of benzophenones, preferably 2-hydroxy-4-methoxybenzophenone-5-sulfonic acid and its salts; sulfonic acid derivatives of 3-benzylidenecamphor, as for example 4-(2-oxo-3-bornylidenemethyl)benzene sulfonic acid and 2-methyl-5-(2-oxo-3-bornylidene) sulfonic acid and its salts.

Typical UV-A filters particularly include derivatives of benzoylmethane, such as, for example 1-(4'-tert.-butylphenyl)-3-(4'-methoxyphenyl)propane-1,3-dione, 4-tert.-butyl-4'-methoxydibenzoylmethane (Parsol 1789), 1-phenyl-3-(4'- isopropylphenyl)-propane-1,3-dione as well as enamine compounds, as described in the DE 1 971 2033 A1 (BASF). Naturally, the UV-A and UV-B filters can also be added as mixtures. Beside the cited soluble materials, insoluble, light protective pigments, namely finely dispersed, preferably, nano metal oxides or salts can also be considered for this task. Exemplary suitable metal oxides are particularly zinc oxide and titanium oxide and also oxides of iron, zirconium, silicon, manganese, aluminum and cerium as well as their mixtures. Silicates (talc), barium sulfate or zinc stearate can be added as salts. The oxides and salts are already used in the form of pigments for skin care and skin protecting emulsions and decorative cosmetics. Here, the particles should have a mean diameter of less than 100 nm, preferably between 5 and 50 nm and especially between 15 and 30 nm. They can be spherical, however elliptical or other shaped particles can also be used. The pigments can also be surface treated, i.e. hydrophilized or hydrophobized. Typical examples are coated titanium dioxides, such as, for example Titandioxid Z 805 (Degussa) or Eusolex® T2000 (Merck); preferably, silicones and particularly preferably trialkoxy octylsilanes or Simethicones are used as the hydrophobic coating agents Preferably, micronized zinc oxide is used. Further suitable UV light protection filters may be found in the review by P. Finkel in SöFW-Journal, Volume 122 (543), p. 1996.

The UV absorbers are normally used in amounts of 0.01 wt. % to 5 wt. %, preferably from 0.03 wt. % to 1 wt. %.

In general, laundry or cleaning active enzymes are also counted among the conventional ingredients for detergents and cleaning agents.

Consequently, detergents or cleaning agents that are characterized by an above described, inventive protein, protein fragment, fusion protein or derivative as well as additional further enzymes, represent preferred embodiments of the present invention. In particular they include other esterases, proteases, amylases, cellulases, hemicellulases such as for example β-glucanases, oxidoreductases such as for example laccases, cutinases and/or lipases, but also esterases and all other enzymes, which are described in the prior art for this field of application.

Enzymes like proteases, amylases, lipases or cellulases have been used for decades as active components in detergents and cleaning agents. Their respective contribution to the washing or cleaning performance of the agents in question is, in the case of proteases the ability to degrade protein-containing stains, in the case of amylases the degradation of starch-containing stains, and in the case of lipases the fat cleaving activity.

Cellulases are preferably used in detergents, in particular due to their contribution to the secondary washing performance of a detergent and due to their fiber action on textiles, in addition to their soil-removing, i.e. primary washing and cleaning performance. The particular hydrolytic products are attacked, dissolved, emulsified or suspended by the other detergent or cleaning agent components or are, due to their greater solubility, washed away with the wash liquor, resulting in synergistic effects between the enzymes and the other components.

Proteases can exert an effect on natural fibers, in particular on wool or silk, comparable to the contribution made by cellulase to the secondary washing performance of a detergent. Due to their action on the surface structure of such fabrics, they can exert a smoothing influence on the material and thereby counteract felting.

Other enzymes extend the cleaning performance of appropriate agents according to their own specific enzyme performance. Examples of these include β-glucanases, oxidoreductases such as for example laccases or pectin-dissolving enzymes, which are used, in particular, in special detergents.

Enzymes suitable for use in inventive detergents or cleaning agents are primarily those isolated from microorganisms such as bacteria or fungi. They are obtained from suitable microorganisms in a manner known per se by means of fermentation processes.

An inventive protein and/or other proteins present can be protected, particularly in storage, against deterioration such as, for example denaturation, decomposition or inactivation, for example through physical influences, oxidation or proteolytic cleavage. This is the case for all inventive agents, particularly detergents and cleaning agents.

One group of stabilizers are reversible protease inhibitors, which dissociate off when the agent is diluted in the wash liquor. Benzamidine hydrochloride and leupeptin are established for this purpose. Frequently, borax, boric acids, boronic acids or salts or esters thereof are used, including especially the derivatives with aromatic groups, ortho-substituted, meta-substituted and para-substituted phenylboronic acids, or salts or esters thereof. Peptide aldehydes, i.e. oligopeptides with reduced C terminus, that is those of 2-50 monomers, are employed to reversibly inhibit detergent and cleaning agent proteases. The peptidic reversible protease inhibitors include, inter alia, ovomucoid For example, specific reversible peptide inhibitors of the protease Subtilisin can be employed in protease-containing agents and corresponding fusion proteins of protease and inhibitor.

Further enzyme stabilizers are amino alcohols like mono-, di-, triethanolamine and -propanolamine and their mixtures, aliphatic carboxylic acids up to $C_{12}$, such as succinic acid, other dicarboxylic acids or salts of the cited acids. End group-capped fatty amide alkoxylates are disclosed for this purpose in the prior art. Certain organic acids used as builders are capable of additionally stabilizing an included enzyme.

Lower aliphatic alcohols, but above all polyols such as, for example glycerine, ethylene glycol, propylene glycol or sorbitol are further frequently used enzyme stabilizers. Likewise, calcium salts are used, such as for example calcium acetate or calcium-formate, and magnesium salts.

Polyamide oligomers or polymeric compounds-like lignin, water-soluble vinyl copolymers or cellulose ethers, acrylic polymers and/or polyamides stabilize enzyme preparations against physical influences or pH variations. Polymers containing polyamine-N-oxide act simultaneously as enzyme stabilizers and color transfer inhibitors. Other polymeric stabilizers are the linear $C_8$-$C_{18}$ polyoxyalkylenes. Alkyl polyglycosides may stabilize the enzymatic components of the inventive agent and even increase their performance. Crosslinked nitrogen-containing compounds fulfill a dual function as soil release agents and as enzyme stabilizers. Hydrophobic, non-ionic polymer in a mixture with other stabilizers acts in a stabilizing manner on a cellulase such that those or similar components may also be suitable for the enzyme essential to the invention.

Reducing agents and antioxidants increase the stability of enzymes against oxidative decomposition. Sulfur-containing reducing agents are known. Other examples are sodium sulfite and reducing sugars.

Combinations of stabilizers are also frequently used, for example of polyols, boric acid and/or borax, the combination of boric acid or borate, reducing salts and succinic acid or other dicarboxylic acids or the combination of boric acid or borate with polyols or polyamino compounds and with reducing salts are disclosed. The action of peptide-aldehyde stabilizers is increased by combination with boric acid and/or boric acid derivatives and polyols and still further increased by the additional use of calcium ions.

Agents containing stabilized enzyme activities are preferred embodiments of the present invention. Particular preference is given to those containing enzymes stabilized by more than one of the illustrated ways.

Since agents of the invention can be provided in any conceivable form, enzymes or proteins of the invention in any formulations that are appropriate for addition to the particular agents, represent respective embodiments of the present invention. Examples thereof include liquid formulations, solid granules or capsules.

The encapsulated form is a way of protecting the enzymes or other ingredients against other components such as, for example, bleaching agents, or of making possible a controlled release. Depending on their size, said capsules are divided into milli-, micro- and nanocapsules, microcapsules being particularly preferred for enzymes. A possible encapsulation method is to encapsulate the proteins, starting from a mixture of the protein solution with a solution or suspension of starch or a starch derivative, in this substance.

In the case of solid agents, the proteins may be used, for example, in dried, granulated and/or encapsulated form. They can be added separately, i.e. as one phase, or together with other ingredients in the same phase, with or without compaction. If microencapsulated, solid enzymes are used, then the water can be removed from the aqueous solutions resulting from the process by means of processes known from the prior art, such as spray-drying, centrifugation or by transdissolution. The particles obtained in this manner normally have a particle size between 50 and 200 µm.

Starting from protein recovery carried out according to the prior art, and preparation in a concentrated aqueous or non-aqueous solution, suspension or emulsion, but also in gel form or encapsulated or as dried powder, the inventive enzymes and also the inventive protein can be added to liquid, gel-like or paste-like agents of the invention. Such detergents or cleaning agents of the invention are usually prepared by simply mixing the ingredients, which may be introduced as solids or as solution into an automated mixer.

Apart from the primary washing performance, the esterases comprised in detergents may further fulfill the function of activating, or, after an appropriate contact time, inactivating other components by esterolytic cleavage. Comparable regulatory functions are also possible via the protein of the invention. Another embodiment of the present invention relates to those agents containing capsules of esterase-sensitive material, which capsules are hydrolyzed, for example, by proteins of the invention at the intended time and release their contents. A comparable effect may also be achieved in other multi-phase agents.

Agents for the treatment of textile raw materials or for textile care, which are characterized in that they comprise one of the above described, inventive proteins, protein fragments, fusion proteins or derivatives, either alone or in addition to other ingredients, are a separate subject matter of the invention, in particular for fibers or textiles with artificial fiber components, and quite particularly for those containing polyester.

Synthetic fibers, such as for example polyester are also characterized by a characteristic surface structure. In the long term, particularly when subjected to a plurality of wash processes, this can result in undesired effects such as, for example, felting, "pilling". In order to avoid such effects, either the raw materials or the finished material, the textile or the fibers are treated with the inventive agents; this contributes, for example, to smoothing the surface structure and thereby counteracts felting.

The inventive agents are preferably used to improve the appearance and/or the surface structure of already felted (pilled) fibers, particularly polyester fibers. The inventive enzymes are capable of cleaving the ester bonds of the felted (pilled) synthetic fibers, and thereby to reverse (depilling), to prevent from the outset, to significantly retard and/or even totally stop the felting or pilling.

In a preferred embodiment, the agent containing an inventive esterase is designed in such a way that it can be used regularly as a conditioner, for example by adding it to the washing process, applying it after washing or independently of the washing. The desired effect is to obtain a smooth surface structure of the textile over a long period and/or to prevent and/or reduce damage to the fabric.

A separate subject matter of the invention is constituted by processes for the automatic cleaning of textiles or of hard surfaces, said processes being characterized in that an above-described, inventive protein, protein fragment, fusion protein or derivative is active in at least one of the process steps in an amount of 0.01 µg to 96 g, preferably 0.05 µg to 72 g, particularly preferably 0.1 µg to 48 g and quite particularly preferably 0.5 µg to 24 g per application.

These processes include both manual as well as automatic processes, automatic processes being preferred due to their more precise controllability that concerns for example the added quantities and contact times.

Processes for the cleaning of textiles are generally characterized in that various cleaning-active substances are applied to the material to be cleaned in a plurality of process steps and, after the contact time, are washed away, or that the material to be cleaned is treated in any other way with a detergent or a solution of said agent. The same applies to methods for cleaning any materials other than textiles, which are classified by the term hard surfaces. It is possible to add inventive proteins to at least one of the process steps of all conceivable washing or cleaning processes; accordingly, these processes then become embodiments of the present invention.

An individual partial step of such a process for automatic cleaning of textiles can consist of applying, if desired in addition to stabilizing compounds, salts or buffer substances, an inventive enzyme as the single active component. This is a particularly preferred embodiment of the present invention.

In a further preferred embodiment of such processes, the inventive enzymes in question are supplied in the context of one of the above listed formulations for inventive agents, preferably inventive detergents or cleaning agents.

Preferred embodiments of this subject matter of the invention are processes for the treatment of textile raw materials or for textile care, which are characterized in that in at least one of the process steps one of the above described, inventive proteins, protein fragments, fusion proteins or derivatives is active, particularly for textile raw materials, fibers or textiles containing synthetic components, and quite particularly for those containing synthetic fibers, particularly polyester.

This can concern processes for example in which materials are prepared for treating textiles, for example for an anti-pilling finish or for example processes that add a care component when cleaning worn textiles. Preferred embodiments concern processes for the treatment of textile raw materials, fibers or textiles containing synthetic components, particularly containing synthetic fibers, preferably polyester.

The use of one of the above described, inventive protein, protein fragment, fusion protein or derivative for the cleaning of textiles or of hard surfaces is a separate subject matter of the invention.

Preferably, the above listed concentration ranges apply to this use.

Inventive proteins, particularly corresponding to the above described characteristics and the above described processes, can be used for the depilling of textiles. Washing by hand or the manual removal of blemishes from textiles or from hard surfaces or the use in connection with an automatic process are exemplary embodiments.

In a preferred embodiment of this use, the inventive enzymes in question are supplied in the context of one of the above listed formulations for inventive agents, preferably inventive detergents or cleaning agents.

The use of one of the above described, inventive protein, protein fragment, fusion protein or derivative for the activation or deactivation of ingredients of detergents or cleaning agents is a further embodiment of this subject matter of the invention.

As is known, ingredients of detergents or cleaning agents can be inactivated by the action of an esterase. A subject matter of the present invention is to purposely utilize this otherwise rather undesired effect. It is likewise possible, as described above, that another component is first activated by esterolytic cleavage, for example if said component is a hybrid protein of the actual enzyme and the corresponding inhibitor. Another example of a regulation of this kind is one in which an active component, in order to protect or control its activity, has been encapsulated in a material susceptible to esterolytic attack. Proteins of the invention can thus be used for inactivation reactions, activation reactions or release reactions, in particular in multi phase agents.

The use for the controlled and/or retarded release of fragrances, such as for example perfume oils, is particularly suitable.

All other technical processes, uses and associated agents residing outside the scope of detergents and cleaning, are summarized, irrespective of their diversity, in a subject matter of the invention, in so far as they are characterized by an inventive protein. This compilation is not to be understood as an exhaustive listing, but rather assembles the most important presently recognized application possibilities of the inventive esterases. Should it transpire that the employment of inventive esterases can further develop additional technical fields then these are included in the scope of protection of the present invention.

The use of one of the above described, inventive protein, protein fragment, fusion protein or derivative for biochemical analysis or for the synthesis of low molecular weight compounds is an embodiment of this subject matter of the invention.

This use preferably occurs in the context of corresponding agents or processes. According to the invention, enzymatic analysis is understood to mean any biochemical analysis that uses specific enzymes or substrates in order to determine on the one hand the identity or the concentration of substrates or on the other hand the identity or activity of enzymes. The fields of application are all those related to biochemistry, in particular molecular biology and protein chemistry. This use preferably occurs in the context of an enzymatic analytical method.

The use of one of the above described, inventive protein, protein fragment, fusion protein or derivative for the preparation, purification or synthesis of natural products or valuable biological products is a further embodiment of this subject matter of the invention.

This use preferably occurs in the context of corresponding agents or processes. Thus, it may be necessary, for example, in the course of purifying natural products or valuable biological products, to remove from said products protein contaminations. These, for example, can be low molecular weight compounds, any cellular constituents or storage substances or proteins. This may be carried out both on the laboratory scale and the industrial scale, for example after the biotechnological production of a valuable product.

In addition, the use of the inventive proteins in detergents and cleaning agents can reduce the satin gloss that is observed with polyester fibers and is regarded as being rather cheap by consumers. In addition, the formation of glossy areas on synthetic fibers on washing can be reduced or even essentially prevented. Glossy areas already formed by strong wear of the fibers, e.g. rubbing or chafing, are reduced by the use of detergents and cleaning agents that comprise the inventive enzymes.

Furthermore, the inventive enzymes can be used to reduce or even to prevent redeposition, i.e. the attachment of soil from the wash liquor during the washing process.

Moreover, the use of inventive enzymes in detergents and cleaning agents permits an overall improvement of the cleaning power.

The use of an inventive esterolytic enzyme for the synthesis of esters or other low molecular weight chemical compounds occurs in reverse of the reaction naturally catalyzed by it, for example then when carboxyl groups are esterified or are intended to be bonded with mono- di- or polyols.

In addition, the esterases, in particular polyesterases, preferably the para-nitrobenzyl esterases can be employed for chemical syntheses or purification in a chemical synthesis. As enzymes generally possess stereoselective catalytic centers, it is possible to employ the cited enzymes for the separation of racemates or for stereoselective syntheses.

The use of one of the above described, inventive protein, protein fragment, fusion protein or derivative for the treatment of natural or synthetic raw materials, particularly for surface treatment, is a further embodiment of this subject matter of the invention.

This use preferably occurs in the context of corresponding agents or processes. It is required, for example, when certain impurities have to be eliminated from raw materials. Among these are primarily understood synthetically obtainable raw materials, such as polyester compounds, although also substances manufactured biotechnologically using fermentation, such as for example antibiotics.

Using polyesterases, in particular p-nitrobenzyl esterases, preferably obtainable from bacteria of the genus *Bacillus*, in processes for the manufacture and/or purification of polyesters, in particular polyalkylene terephthalates. In the manufacture of polyalkylene terephthalates, in particular polyethylene terephthalate (PET), the polymer yield is influenced by a side reaction that leads to the formation of cyclic oligomers. By means of the inventive use, it is possible to effect the retro synthesis of the formed cyclic oligomers and make available the monomers for further reaction. The products from the side reaction are thus repressed and a higher yield of desired polymer is achieved.

The use of one of the above described, inventive protein, protein fragment, fusion protein or derivative for the production or treatment of raw materials or intermediates in textile manufacturing, in particular to remove protective layers on fabrics, is a further embodiment of this subject matter of the invention.

This use preferably occurs in the context of corresponding agents or processes. An example for the production or treatment of raw materials or intermediates in textile manufacturing is the finishing of synthetic fibers. Enzymatic processes or uses are superior to comparable chemical processes, particularly in regard to their environmental impact.

In a preferred embodiment, inventive proteins are used to remove protective layers of textiles, in particular intermediates or materials, or to smooth their surface, prior to further treatment in a subsequent processing step.

The use of one of the above described, inventive protein, protein fragment, fusion protein or derivative for the treatment of textile raw materials or for textile care, in particular for the treatment of synthetic fibers, particularly polyesters, or mixed textiles containing synthetic fibers, is a further embodiment of this subject matter of the invention.

This use preferably occurs in the context of corresponding agents or processes. In accordance with the above statements, the textile raw materials in question are freed from impurities by the esterases; furthermore the surface smoothing and care properties of the esterolytic enzyme benefit a material consisting at least partially of protein. For this reason the use for caring for the materials in question is also included. Consequently, in particular the surface treatment of synthetic fibers, particularly polyesters, or of mixed textiles comprising synthetic fibers, is claimed. This applies both to the preparation of such textiles and also to the care during usage, for example in connection with the cleaning of textiles (see above).

In a further embodiment of this subject matter of the invention, the above described, inventive proteins are employed for cosmetic purposes.

Consequently, are claimed cosmetics with one of the above described inventive protein, protein fragment, fusion protein or derivative, or cosmetic processes involving one of the above described inventive protein, protein fragment, fusion protein or derivative, or the use of one of the above described inventive protein, protein fragment, fusion protein or derivative for cosmetic purposes, particularly in the context of appropriate processes or in appropriate agents.

Accordingly, the use of esterolytic enzymes of this kind for cosmetic purposes, in particular in appropriate agents such as, for example, shampoos, soaps or washing lotions or in care compositions provided, for example, in the form of creams, is also included in this subject matter of the invention. The use in a peeling medicament and its manufacture is also included in this claim.

A further subject of the invention is the use of inventive esterases for applications in the manufacture of medicaments, particularly the manufacture of antibiotics. During synthesis, carboxyl groups in substances are often protected by a para-nitrobenzyl protective group. It is therefore preferred to utilize the inventive esterases in chemical syntheses to cleave the protecting group, particularly in the manufacture of medicaments, particularly the manufacture of antibiotics. Preferably, this occurs in aqueous media at temperatures between 25 and 40° C.

A further subject of the invention concerns articles of polyester that result from the inventive use or the application of the inventive process and/or are produced and/or treated with one of the abovementioned agents, wherein the article of polyester possesses an improved handling and feel, depilling characteristics or protection against pilling.

For the cited inventive uses, those esterases are particularly preferred, which according to the methods 2.4 cited in the examples exhibit a specific activity towards the substrate bis-(p-methylbenzoic acid) ester of ethylene glycol of 0.1 to 30, preferably 0.6 to 20, particularly 0.7 to 15, quite particularly preferably 0.9 to 10, even more strongly preferably 1 to 5, particularly 1.1 to 4, quite particularly preferably 1.5 to 3 (μmol liberated acid)/(min*mg enzyme). These esterases have proved to be particularly advantageous for use in the inventive agents or uses and processes.

Furthermore, those esterases are particularly preferred which are homologous to the protein sequences listed under Seq. ID Nr. 12 to at least 50%, at least 55%, particularly at least 60%, preferably at least 65%, particularly preferably at least 70%, advantageously at least 75%, quite particularly preferably at least 80%, particularly preferably at least 85%, at least 90%, at least 95%, at least 99%, especially 100%.

EXAMPLES

1. Sequences of the Inventive Esterases

TABLE 1

Classification of the sequence ID numbers

| SEQ ID No. | Organism | Protein/DNA/RNA | Databank entry no. NCBI | Esterase/Lipase |
|---|---|---|---|---|
| 1 | Bacillus subtilis | Protein | — | PNBE |
| 2 | Bacillus licheniformis | Protein | — | PNBE |
| 3 | Bacillus subtilis | DNA/RNA | — | PNBE |
| 4 | Bacillus licheniformis | DNA/RNA | — | PNBE |
| 5 | Bacillus subtilis | Preprotein | | PNBE |
| 6 | Bacillus licheniformis | Preprotein | | PNBE |
| 7 | Bacillus subtilis | DNA/RNA | | PNBE |
| 8 | Bacillus subtilis | DNA/RNA | | PNBE |
| 9 | Artificial | Signal peptide | | PNBE |
| 10 | Artificial | DNA/RNA | | PNBE |
| 11 | Bacillus subtilis | Protein | gi 1762126 | PNBE |
| 12 | Bacillus licheniformis DSM13 | Protein | gi 52346943 | PNBE |
| 13 | Bacillus subtilis | Protein | gi 7546321 | PNBE |
| 14 | Bacillus subtilis | Protein | gi 468046 | PNBE |
| 15 | Bacillus subtilis | Protein | gi 17621265 | PNBE |
| 16 | Bacillus subtilis | Protein | gi 1495277 | PNBE |
| 17 | Bacillus subtilis | Protein | gi 1945688 | PNBE |
| 18 | Bacillus subtilis | Protein | gi 2635952 | PNBE |
| 19 | Bacillus licheniformis ATCC 14580 | Protein | gi 52002286 | PNBE |
| 20 | Staphylococcus epidermis ATCC 12228 | Protein | gi 27316488 | PNBE |
| 21 | Staphylococcus aureus | Protein | gi 57286454 | PNBE |
| 22 | Streptomyces avermitilis MA-4860 | Protein | gi 29611030 | PNBE |
| 23 | Caulobacterium crescentus CB15 | Protein | gi 13422044 | PNBE |
| 24 | Clostridium acetobutylicum ATCC824 | Protein | gi 14994366 | PNBE |
| 25 | Artificial | Protein | gi 7546320 | PNBE |
| 26 | Burkholderia cepacia | Protein | gi 67464317 | Lipase |
| 27 | Bacillus licheniformis DSM13 | DNA | | PNBE |

2. Determination of the Enzyme Activities 2.1 Determination of Esterase Activity with Para-Nitrophenyl Esters The detection of the esterase activity was determined using standard methods with para-nitrophenyl acetate (pNPA). For this a 400 mM parent solution was mixed with DMSO. 980 μL of a 50 mM tris-HCl-buffer (pH 8.0) were mixed with 10 μL para-nitrophenyl acetate dissolved in DMSO. The reaction was carried out—if not otherwise described—at room temperature and started by adding 10 µL of enzyme solution. The increase in absorption at 410 nm was then measured (UV MC2, SAFAS, Monaco). The enzyme activity was calculated with a molar extinction coefficient of 17100 [M−1 cm−1], wherein 1 unit was defined as the quantity of enzyme that released 1 µmol p-nitrophenol per minute.

2.2 Determination of Esterase Activity with Phenol Red

For the biochemical purification of dialkyl phthalate-hydrolases, esterolytic activity determinations were used against diethyl terephthalate (DET) as the substrate with a photometric measurement method that showed the acidification of the test system by means of pH indicators. The basic principle of this test system is the same proton affinity of the added buffer (EPPS-P$_{uffer}$; PK$_a$=8.0) and of the added pH indicator (phenol red; pK$_a$=8.0), which enable a linear trend of the decrease in absorption at 560 nm. To calculate the activity, the following formula 2.1 and 2.2 were used with Q=buffer factor; cb$_{uffer}$=final concentration of buffer; c$_{indicator}$=final concentration of indicator; $\Delta\epsilon_{560nm}$: difference of the deprotonated form and protonated form of phenol red; A: activity of the esterase; dE/dt: extinction decrease over time; V$_{reaction}$: reaction volume:

$$Q = \frac{C_{buffer}}{C_{indicator}} * \frac{t}{\Delta\varepsilon_{560nm} * L} \quad (2.1)$$

$$A = (\mu mol * min^{-1}) = \frac{dE}{dt} * Q * V_{reaction} * 10^{-6} \quad (2.2)$$

The enzyme activity was calculated using an empirically determined molar extinction coefficient of 58000 [M$^{-1}$cm$^{-1}$] for the deprotonated and 100 [M$^{-1}$cm$^{-1}$] for the protonated form, wherein 1 unit is defined as the quantity of enzyme that releases 1 µmol acid per minute.

2.3 Determination of the Esterase Activity by Titration

Figure 4:
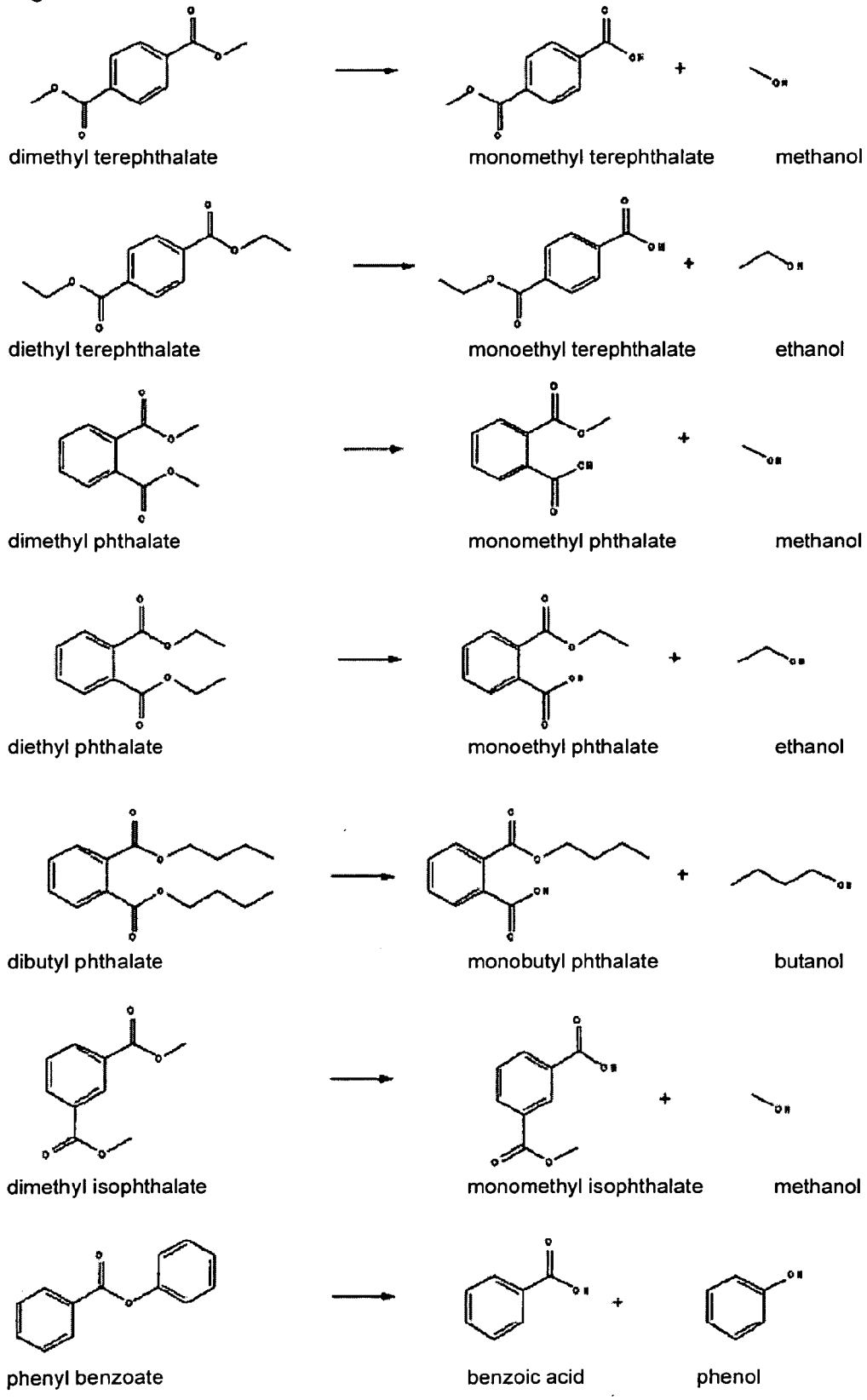

The enzyme activities of the esterases were measured with the titration apparatus 702 SAT (METROHM Ltd., Switzerland) for various substrates of the phthalate family (FIG. 4). The phthalates were dissolved in diethyl ether with 0.5 g Triton X100. The diethyl ether was then removed under a stream of nitrogen. 50 ml buffer (2 mM Tris/HCl, pH 9) was added, homogenized by ultrasound and used in different final concentrations (0.3 mM to 100 mM) in a total reaction volume of 2 mL (including enzyme). The reaction buffer was pre-incubated at 30° C. for 10 minutes. After addition of the enzyme, the NaOH consumption (concentration determination by triple titration with oxalic acid) at a reaction temperature of 30° C. was plotted. One unit is defined as the enzyme activity that releases 1 µmol acid per minute.

2.4 Determination of the Esterase Activity by Hydrolysis of Bis-(P-Methylbenzoic Acid) Ester of Ethylene Glycol 2.4.1 Synthesis of Bis-(P-Methylbenzoic Acid) Ester of Ethylene Glycol Bis-(p-methylbenzoic acid) ester of ethylene glycol was synthesized by the esterification of 4-methylbenzoyl chloride and ethylene glycol (see FIG. 1). Ethylene glycol and pyridine were placed in a round bottomed flask equipped with a reflux column and 4-methylbenzoyl chloride was added drop wise under ice cooling. The mixture was allowed to stand for 16 hours and then the resulting solid ester was filtered off and recrystallized in 70% ethanol 30% water. The resulting solid was then washed with 70% ethanol and lyophilised for 24 hours.

2.4.2 Determination of the Enzymatic Activity

Figure 2:
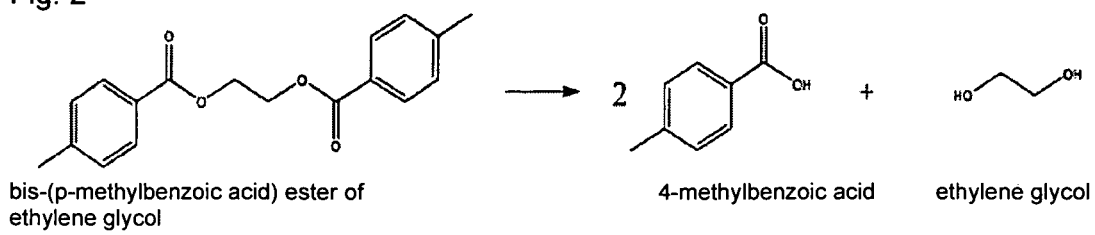

The cleavage of the bis-(p-methylbenzoic acid) ester of ethylene glycol catalyzed by the inventive enzymes affords 2 equivalents of 4-methylbenzoic acid and ethylene glycol (see FIG. 2).

For the preparation of the enzyme assay, the desired amount of substrate was mixed with 0.5 g Triton X100 and dissolved with heating in 50 mL ethanol (99%, denatured). Once all the substrate was dissolved, the solution was added to 50 mL buffer (2 mM tris/HCl buffer; pH 9.0) with intense stirring by Ultra-Turrax. This solution was then stirred at room temperature for at least 12 hours in order to remove a large part of the added ethanol. The thus-prepared substrate solution was immediately titrated. The reaction buffer was pre-incubated at 30° C. for 10 minutes.

Different final concentrations (0.67 mM to 50 mM) were used in a total reaction volume of 2 mL including enzyme. After addition of the enzyme, the NaOH consumption (concentration determination by triple titration with oxalic acid) with the titration apparatus 702 SAT (METROHM Ltd., Switzerland)) at a reaction temperature of 30° C. was plotted. One unit is defined as the enzyme activity that releases 1 µmol acid per minute.

In this and the subsequent examples, the following abbreviations are used for the tested esterases: enzyme according to Seq ID No. 12 (pNB-Est13), enzyme according to Seq ID No. 2 (pNB-Est19), enzyme according to Seq ID No. 1 (pNB-Est17). The data obtained for the cited esterases in Table 2 were determined by titrimetric measurements and represent mean values from: three independent measurements with a relative standard deviation of less than 5%.

TABLE 2

Kinetic data of the hydrolysis of the bis-(p-methylbenzoic acid) ester of ethylene glycol by para-nitrobenzyl esterases pNB-Est17, pNB-Est19 and pNB-Est13

| bis-(p-methylbenzoic acid) ester of ethylene glycol | v$_{max}$ [µmol/min] | k$_M$ [mM] | k$_{cat}$ [1/s] | k$_{cat}$/k$_M$ [1/mM * s] | Specific Activity [µmol/min * mg] |
|---|---|---|---|---|---|
| Enzyme acc. Seq ID No. 1 (pNB-Est17) | 0.642 | 9.83 | 5177 | 527 | 1.60 |
| Enzyme acc. Seq ID No. 2 (pNB-Est19) | 0.385 | 3.59 | 3838 | 1070 | 1.19 |
| Enzyme acc. Seq ID No. 12 (pNB-Est13) | 1.801 | 11.21 | 9358 | 835 | 2.87 |

3. Investigation of the Substrate Specificity to Para-Nitrophenyl Esters and Triglycerides of Different Chain Lengths For the determination of chain length specificities of the investigated esterases, p-nitrophenyl esters with different chain lengths were used as the substrate for the spectroscopic measurements of activity. To the p-nitrophenyl esters dissolved in 10 mL isopropanol were added 90 mL phosphate buffer (pH 8, disodium hydrogen phosphate and potassium dihydrogen phosphate). The final concentration of the substrate was 0.8 mM. Each 990 µL buffer-substrate mixture was mixed with 10 µL of the enzyme sample and incubated at room temperature for one minute. The increase in absorption at 410 nm was then measured (UV MC$^2$, SAFAS, Monaco). The enzyme activity was calculated using a molar extinction coefficient of 17100 [M$^{-1}$cm$^{-1}$], wherein 1 unit was defined as the quantity of enzyme that released 1 µmol p-nitrophenol per minute.

The data in Table 3 represent mean values from three independent measurements with a relative standard deviation of less than 10%.

TABLE 3

Substrate specificities of pNB-Est13, pNB-Est17 and pNB-Est19 with different chain lengths of the para-nitrophenyl esters

| | Specific Activity [U/mg] | | |
|---|---|---|---|
| Substrate | pNB-Est13 | pNB-EST17 | pNB-Est19 |
| p-NP-butyrate | 22.4 | 196.3 | 234.8 |
| p-NP-caproate | 50.5 | 102.7 | 249.6 |
| p-NP-caprylate | 13.0 | 73.2 | 83.6 |
| p-NP-caprate | 4.4 | 10.2 | 3.9 |
| p-NP-laurate | 1.3 | 3.4 | 4.0 |
| p-NP-myristate | <1 | <1 | 1.3 |
| p-NP-palmitate | <1 | <1 | <1 |
| p-NP-stearate | <1 | <1 | <1 |

4. Analytical Detection of the Hydrolysis Products of Various Dialkyl Phthalates after Incubation with the Para-Nitrobenzyl Esterases pNB-Est17, pNB-Est19 and pNB-Est13

The esterolytic activity of the pNB esterases towards different dialkyl phthalates was verified by detecting the products of cleavage. The detection involved both thin layer chromatography and gas chromatography coupled to mass spectroscopy (GC/MS). The RF-values of the starting materials and reaction products determined by thin layer chromatography are shown in Table 3. The detection of one or two new spots indicates hydrolysis. Each of the blind samples exhibited no additional spots.

A mixture of 90% dichloromethane/10% methanol was used as the eluent in a presaturated TLC chamber; the separation of the substances was carried out with silica gel 60 F254 coated plates; detection of the individual spots was made under UV light; substrate concentration in the mixture was 6.67 mM, incubation time 2 h at room temperature.

TABLE 4

Characteristic RF values of the starting materials and products determined by thin layer chromatographic analyses of the reaction mixtures containing pNB esterases.

| Substrate | RF Substrate | RF Product 1 | RF Product 2 |
|---|---|---|---|
| Dimethyl terephthalate | 0.78 | 0.18 | |
| Diethyl terephthalate | 0.75 | 0.21 | |
| Dimethyl isophthalate | 0.78 | 0.23 | |
| Dimethyl phthalate | 0.70 | 0.07 | |
| Diethyl phthalate | 0.73 | 0.13 | |
| Dibutyl phthalate | 0.74 | 0.13 | |
| Phenyl benzoate | 0.76 | 0.45 | 0.25 |

Peak assignments of the mass peaks from GC/MS of the cleavage products of the reaction mixtures were carried out by comparison with the WILEY databank and confirmed the hydrolysis that had already been observed by thin layer chromatographic analyses. All observed reactions are schematically illustrated in FIG. 4. Each enzymatic reaction was measured against a blank sample that consisted of the reaction mixture without enzyme or the reaction mixture without substrate. It was shown that for all investigated phthalates and terephthalates, only one of the two possible ester functional groups is hydrolyzed. Free phthalic acid or terephthalic acid or isophthalic acid was not detected in any reaction mixture. In each case the reaction products are the monoester of the starting compound and the relevant alcohol. The hydrolysis of phenyl benzoate was investigated as a substrate that did not belong to the phthalates. Phenol and benzoic acid were detected as the hydrolysis products.

5. Determination of $v_{max}$, $k_M$, $k_{cat}$ and $k_{cat}/k_M$ of the para-nitrobenzyl Esterases pNB-Est17, pNB-Est19 and pNB-Est13 Towards Different Phthalates and Terephthalates Titrimetric measurements were carried out to determine the kinetic constants $v_{max}$, $k_M$, $k_{cat}$ and $k_{cat}/k_M$ of the three para-nitrobenzyl esterases pNB-Est17, pNB-Est19 and pNB-Est13 towards different phthalates and terephthalates. The enzyme activities were determined for different substrate concentrations and evaluated according to MICHAELIS-MENTEN (see FIGS. 5 to 7). The measured $k_M$ and $v_{max}$ values and the added enzyme concentrations were used to calculate the kinetic constants ($k_{cat}$ and $k_2$) and the catalytic efficiency ($k_{cat}/k_M$)—under the assumption that the added enzyme concentration was the same as the concentration of the active enzyme. The resulting values are each summarized in the tables.

Figure 5A:
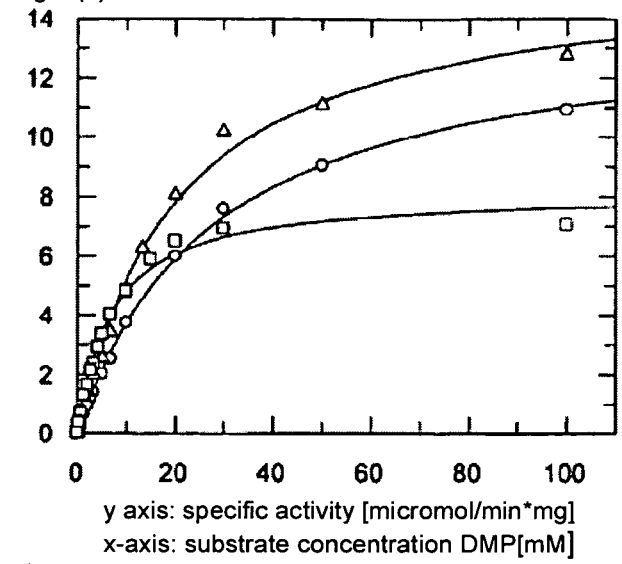
Figure 5B:
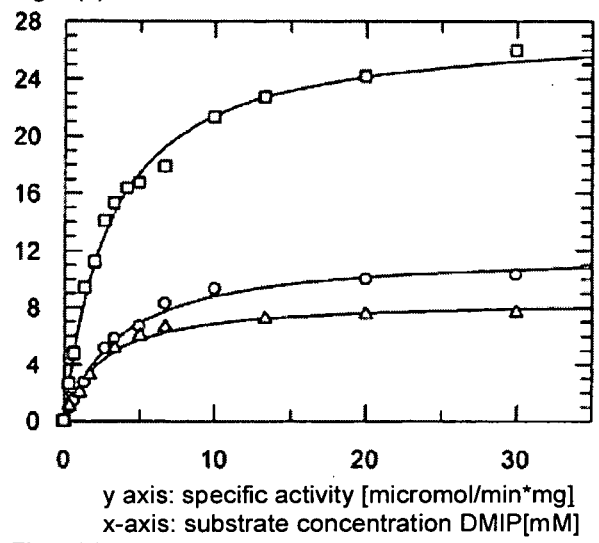
Figure 5:
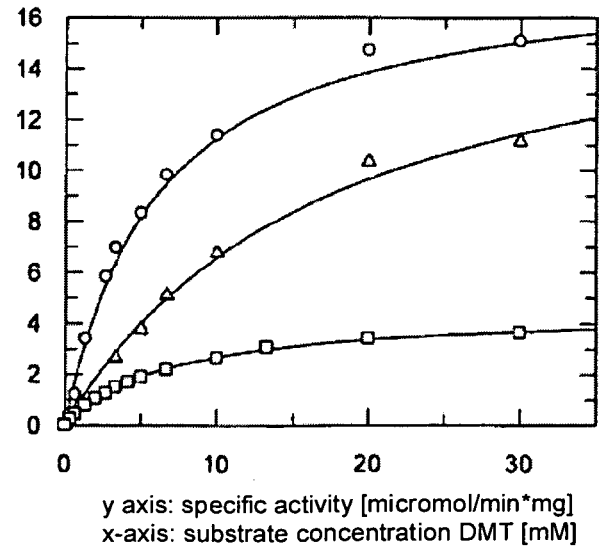
Figure 6A:
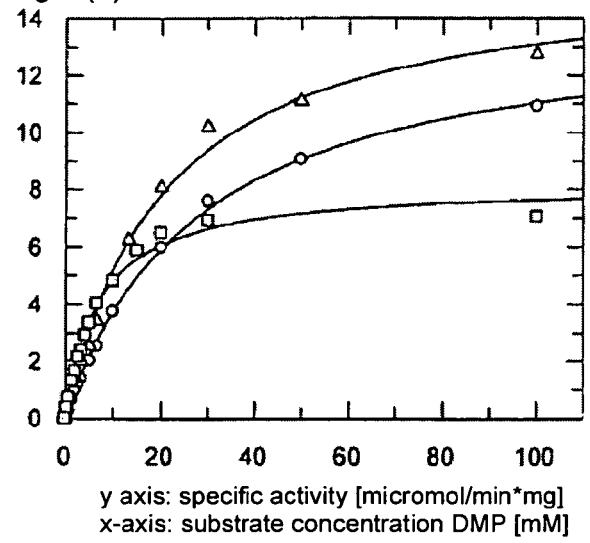
Figure 6B:
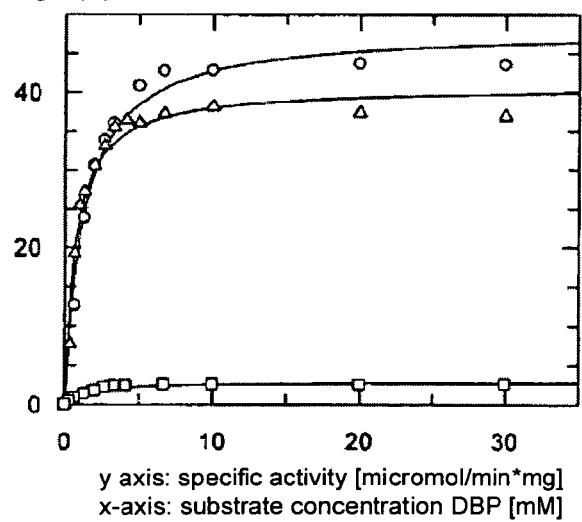
Figure 6:
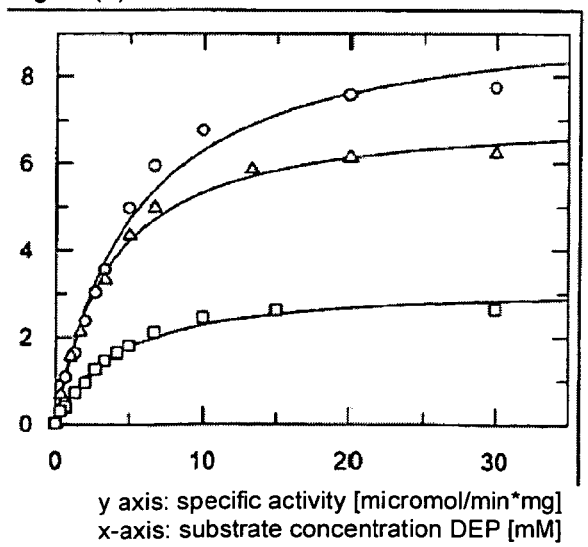
Figure 7:
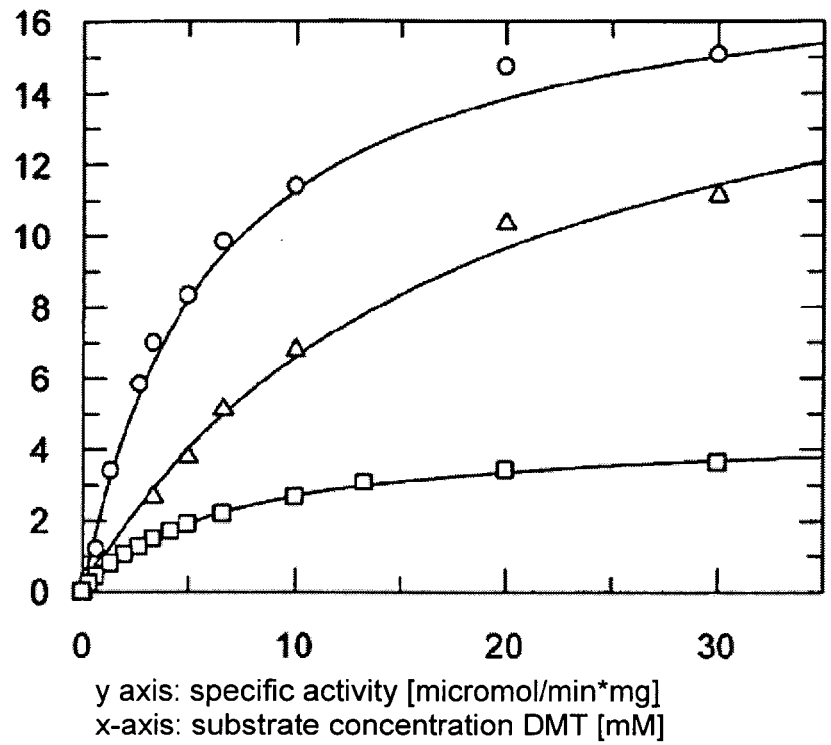
Figure 7:
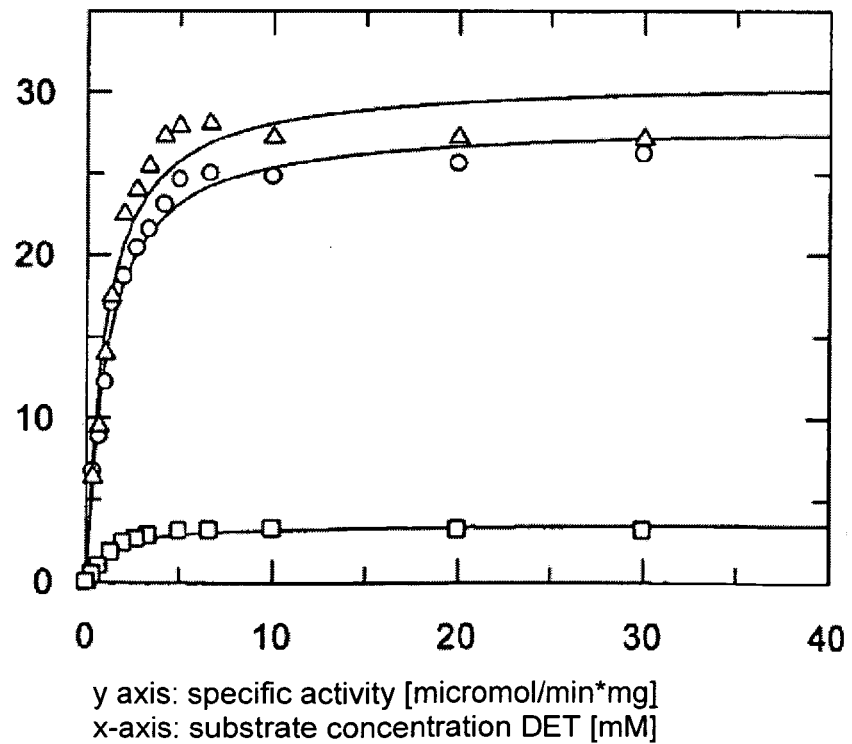

The data in FIGS. 5 to 7 and Tables 5 to 7 represent mean values from three independent titrimetric measurements with a relative standard deviation of less than 5%. The calculation of $k_{cat}$ and $k_{cat}/k_M$ was based on the assumption that the added enzyme concentration was the same as the concentration of the active enzyme.

The monoester of the starting compound with the relevant alcohol could be detected for all three investigated para-nitrobenzyl esterases. In no case could the free phthalic acid or terephthalic acid or isophthalic acid be detected.

Hydrolysis of the Different Isomers (Ortho, Meta, Para) of Dimethyl Phthalates.

TABLE 5

$k_M$ and $V_{max}$ values and $k_{cat}$ and $k_{cat}/k_M$ of the hydrolysis of ortho, meta, para positional isomers of dimethyl phthalate, DMP = dimethyl phthalate; DMIP = dimethyl isophthalate; DMT = dimethyl terephthalate by pNB-Est17, pNB-Est19 and pNB-Est13.

| | pNB-Est17 | pNB-Est19 | pNB-Est13 |
|---|---|---|---|
| Substrat DMP | | | |
| $v_{Max}$ [U/mg] | 14.09 | 15.76 | 9.11 |
| $k_M$ [mM] | 27.70 | 20.35 | 8.68 |
| $k_{cat}$ [1/s] | 45672 | 50970 | 29735 |
| $k_{cat}/k_M$ [1/mM * s] | 1649 | 2505 | 3427 |
| Substrat DMIP | | | |
| $v_{Max}$ [U/mg] | 11.99 | 8.55 | 27.67 |
| $k_M$ [mM] | 3.67 | 2.44 | 2.93 |
| $k_{cat}$ [1/s] | 38880 | 27637 | 90267 |
| $k_{cat}/k_M$ [1/mM * s] | 10594 | 11327 | 30808 |
| Substrat DMT | | | |
| $v_{Max}$ [U/mg] | 18.52 | 15.69 | 4.53 |
| $k_M$ [mM] | 5.99 | 13.56 | 6.87 |
| $k_{cat}$ [1/s] | 60028 | 50718 | 14784 |
| $k_{cat}/k_M$ [1/mM * s] | 10021 | 3741 | 2152 |

Substrat = substrate

Hydrolysis of (Ortho) Phthalates with Different Chain Lengths

TABLE 6

$k_M$ and $V_{max}$ values and $k_{cat}$ and $k_{cat}/k_M$ of the hydrolysis of ortho phthalates with different alkyl chain lengths (DMP = dimethyl phthalate: DEP = diethyl phthalate: DBP = dibutyl phthalate: by pNB-Est17, pNB-Est19 and pNB-Est13.

|  | pNB-Est17 | pNB-Est19 | pNB-Est13 |
|---|---|---|---|
| Substrat DMP |  |  |  |
| $v_{Max}$ [U/mg] | 14.09 | 15.76 | 9.11 |
| $k_M$ [mM] | 27.70 | 20.35 | 8.68 |
| $k_{cat}$ [1/s] | 45672 | 50970 | 29735 |
| $k_{cat}/k_M$ [1/mM * s] | 1649 | 2505 | 3427 |
| Substrat DEP |  |  |  |
| $v_{Max}$ [U/mg] | 9.57 | 7.20 | 3.21 |
| $k_M$ [mM] | 5.20 | 3.55 | 4.14 |
| $k_{cat}$ [1/s] | 31065 | 23265 | 10468 |
| $k_{cat}/k_M$ [1/mM * s] | 5974 | 6554 | 2528 |
| Substrat DBP |  |  |  |
| $v_{Max}$ [U/mg] | 48.03 | 40.69 | 2.87 |
| $k_M$ [mM] | 1.24 | 0.70 | 1.16 |
| $k_{cat}$ [1/s] | 155676 | 23265 | 9356 |
| $k_{cat}/k_M$ [1/mM * s] | 125545 | 187329 | 8066 |

Substrat = substrate

Hydrolysis of (Para) Phthalates with Different Chain Lengths

TABLE 7

$k_M$ and $V_{max}$ values and $k_{cat}$ and $k_{cat}/k_M$ of the hydrolysis of dimethyl terephthalate (DMT) diethyl terephthalate (PET) by pNB-Est17, pNB-Est19 and pNB-Est13.

|  | pNB-Est17 | pNB-Est19 | pNB-Est13 |
|---|---|---|---|
| Substrat DMT |  |  |  |
| $v_{Max}$ [U/mg] | 18.52 | 15.69 | 4.53 |
| $k_M$ [mM] | 5.99 | 13.56 | 6.87 |
| $k_{cat}$ [1/s] | 60028 | 50718 | 14784 |
| $k_{cat}/k_M$ [1/mM * s] | 10021 | 3741 | 2152 |
| Substrat DET |  |  |  |
| $v_{Max}$ [U/mg] | 28.06 | 30.79 | 3.57 |
| $k_M$ [mM] | 1.06 | 0.97 | 1.21 |
| $k_{cat}$ [1/s] | 90998 | 99411 | 12574 |
| $k_{cat}/k_M$ [1/mM * s] | 85847 | 102486 | 10392 |

Substrat = substrate

NOTES TO THE FIGURES

Figure 3:
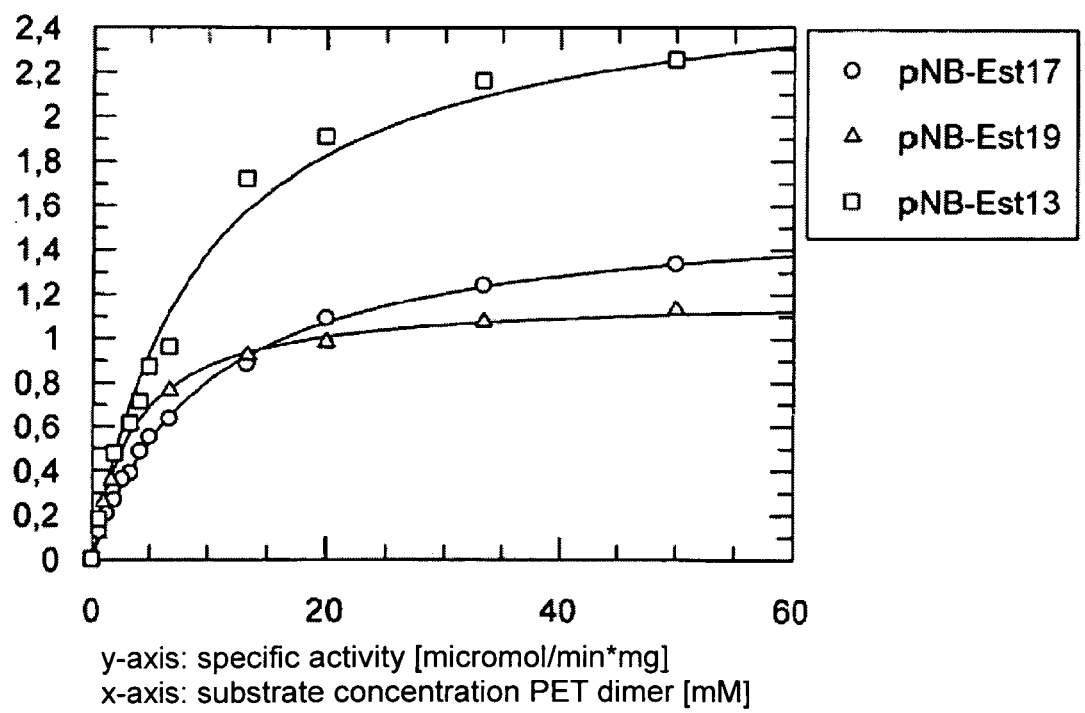

FIG. 1: Synthesis of bis-(p-methylbenzoic acid) ethylene glycol ester by esterification of 4-methylbenzoic acid and ethylene glycol FIG. 2: Scheme of the enzymatic hydrolysis of bis-(p-methylbenzoic acid) ethylene glycol ester FIG. 3. Detection of the enzymatic hydrolysis and identification of the hydrolysis products of bis-(p-methylbenzoic acid) ethylene glycol ester by para-nitrobenzyl esterase FIG. 4: Schematic illustration of the enzyme catalyzed reactions of dimethyl phthalate, diethyl phthalate, dimethyl phthalate, diethyl phthalate, dibutyl phthalate, dimethyl isophthalate and phenyl benzoate.

FIG. 5: MICHAELIS-MENTEN kinetics of the para-nitrobenzyl esterases pNB-Est17 (o), pNB-Est19 (Δ) and pNB-Est13 (□) towards dimethyl phthalate (DMP), dimethyl isophthalate (DMIP) and dimethyl terephthalate (DMT)

FIG. 6: MICHAELIS-MENTEN kinetics of the para-nitrobenzyl esterases pNB-Est17 (o), pNB-Est19 (Δ) and pNB-Est13 (□) towards ortho phthalates: dimethyl phthalate (DMP), diethyl phthalate (DEP) and dibutyl phthalate (DBP).

FIG. 7: MICHAELIS-MENTEN kinetics of the para-nitrobenzyl esterases pNB-Est17 (o), pNB-Est19 (Δ) and pNB-Est13 (□) towards para phthalates: dimethyl terephthalate (DMT) and diethyl terephthalate (DET)

The invention claimed is:

1. A fiber finishing agent comprising an esterase, wherein the agent prevents or reduces pilling of the fibers or of a fabric into which the fibers are woven, wherein the esterase is a para-nitrobenzyl esterase comprising an amino acid sequence that is greater than 99% identical to the amino acid sequence of SEQ ID NOs: 1 or 5, and further comprising an ingredient selected from the group consisting of enzyme stabilizers, surfactants, bleaching agents, and builders.

2. The agent of claim 1, wherein the fiber finishing is selected from the group consisting of treatment of textile raw materials and textile care.

3. The agent of claim 1, wherein the para-nitrobenzyl esterase comprises an amino acid sequence that is identical to at least one of SEQ ID NOs: 1 or 5.

4. An isolated para-nitrobenzyl esterase comprising an amino acid sequence that is greater than 99% identical to the amino acid sequence of at least one of SEQ ID NOs: 1 or 5.

5. The isolated para-nitrobenzyl esterase of claim 4 comprising an amino acid sequence that is identical to the amino acid sequence of at least one of SEQ ID NOs: 1 or 5.

6. A process for the treatment of a textile or a textile raw material comprising reducing pilling of a fabric by treating the textile or textile raw material with a para-nitrobenzyl esterase comprising an amino acid sequence that is greater than 99% identical to the amino acid sequence of at least one of SEQ ID NOs: 1 or 5.

7. The process of claim 6, wherein the para-nitrobenzyl esterase comprises an amino acid sequence that is identical to at least one of SEQ ID NOs: 1 or 5.

8. The process of claim 6, wherein the textile or textile raw material comprises a synthetic fiber.

9. The process of claim 8, wherein the synthetic fiber comprises polyester.

10. The fiber finishing agent of claim 1, wherein the surfactants are selected from the group consisting of non-ionic surfactants, anionic surfactants and amphoteric surfactants.

* * * * *

SEQUENCE LISTING

<160> NUMBER OF SEQ ID NOS: 27

<210> SEQ ID NO 1
<211> LENGTH: 489
<212> TYPE: PRT
<213> ORGANISM: Bacillus subtilis

<400> SEQUENCE: 1

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn

```
            85                  90                  95
Leu Pro Val Met Val Trp Ile His Gly Ala Phe Tyr Leu Gly Ala
            100                 105                 110
Gly Ser Glu Pro Leu Tyr Asp Gly Ser Lys Leu Ala Ala Gln Gly Glu
            115                 120                 125
Val Ile Val Val Thr Leu Asn Tyr Arg Leu Gly Pro Phe Gly Phe Leu
            130                 135                 140
His Leu Ser Ser Phe Asp Glu Ala Tyr Ser Asp Asn Leu Gly Leu Leu
145                 150                 155                 160
Asp Gln Ala Ala Ala Leu Lys Trp Val Arg Glu Asn Ile Ser Ala Phe
                    165                 170                 175
Gly Gly Asp Pro Asp Asn Val Thr Val Phe Gly Glu Ser Ala Gly Gly
                    180                 185                 190
Met Ser Ile Ala Ala Leu Leu Ala Met Pro Ala Ala Lys Gly Leu Phe
                    195                 200                 205
Gln Lys Ala Ile Met Glu Ser Gly Ala Ser Arg Thr Met Thr Lys Glu
                    210                 215                 220
Gln Ala Ala Ser Thr Ser Ala Ala Phe Leu Gln Val Leu Gly Ile Asn
225                 230                 235                 240
Glu Gly Gln Leu Asp Lys Leu His Thr Val Ser Ala Glu Asp Leu Leu
                    245                 250                 255
Lys Ala Ala Asp Gln Leu Arg Ile Ala Glu Lys Glu Asn Ile Phe Gln
                    260                 265                 270
Leu Phe Phe Gln Pro Ala Leu Asp Pro Lys Thr Leu Pro Ala Glu Pro
                    275                 280                 285
Glu Lys Ala Ile Ser Glu Gly Ala Ala Ser Gly Ile Pro Leu Leu Ile
                    290                 295                 300
Gly Thr Thr Arg Asp Glu Gly Tyr Leu Phe Phe Thr Pro Asp Ser Asp
305                 310                 315                 320
Val His Ser Gln Glu Thr Leu Asp Ala Ala Leu Glu Tyr Leu Leu Gly
                    325                 330                 335
Lys Pro Leu Ala Glu Lys Ala Ala Asp Leu Tyr Pro Arg Ser Leu Glu
                    340                 345                 350
Ser Gln Ile His Met Met Thr Asp Leu Leu Phe Trp Arg Pro Ala Val
                    355                 360                 365
Ala Tyr Ala Ser Ala Gln Ser His Tyr Ala Pro Val Trp Met Tyr Arg
                    370                 375                 380
Phe Asp Trp His Pro Lys Lys Pro Pro Tyr Asn Lys Ala Phe His Ala
385                 390                 395                 400
Leu Glu Leu Pro Phe Val Phe Gly Asn Leu Asp Gly Leu Glu Arg Met
                    405                 410                 415
Ala Lys Ala Glu Ile Thr Asp Glu Val Lys Gln Leu Ser His Thr Ile
                    420                 425                 430
Gln Ser Ala Trp Ile Thr Phe Ala Lys Thr Gly Asn Pro Ser Thr Glu
                    435                 440                 445
Ala Val Asn Trp Pro Thr Tyr His Glu Glu Thr Arg Glu Thr Leu Ile
                    450                 455                 460
Leu Asp Ser Glu Ile Thr Ile Glu Asn Asp Pro Glu Ser Glu Lys Arg
465                 470                 475                 480
Gln Lys Leu Phe Pro Ser Lys Gly Glu
                    485

<210> SEQ ID NO 2
<211> LENGTH: 489
```

<212> TYPE: PRT
<213> ORGANISM: Bacillus licheniformis

<400> SEQUENCE: 2

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Glu Val Trp
        35                  40                  45

Glu Asp Val Leu Asp Ala Thr Ala Tyr Gly Pro Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Ala Glu Pro
        275                 280                 285

Glu Lys Ala Ile Ser Glu Gly Ala Ala Ser Gly Ile Pro Leu Leu Ile
290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335

Lys Pro Leu Ala Glu Lys Ala Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala Gln Ser His Tyr Ala Pro Val Trp Met Tyr Arg
370                 375                 380

Phe Asp Trp His Pro Lys Lys Pro Pro Tyr Asn Lys Ala Phe His Ala
385                 390                 395                 400
```

| Leu | Glu | Leu | Pro | Phe | Val | Phe | Gly | Asn | Leu | Asp | Gly | Leu | Glu | Arg | Met |
|---|---|---|---|---|---|---|---|---|---|---|---|---|---|---|---|
| | | | 405 | | | | | 410 | | | | | 415 | | |

| Ala | Lys | Ala | Glu | Ile | Thr | Asp | Glu | Val | Lys | Gln | Leu | Ser | His | Thr | Ile |
|---|---|---|---|---|---|---|---|---|---|---|---|---|---|---|---|
| | | | 420 | | | | | 425 | | | | | 430 | | |

| Gln | Ser | Ala | Trp | Ile | Thr | Phe | Ala | Lys | Thr | Gly | Asn | Pro | Ser | Thr | Glu |
|---|---|---|---|---|---|---|---|---|---|---|---|---|---|---|---|
| | | | 435 | | | | | 440 | | | | | 445 | | |

| Ala | Val | Asn | Trp | Pro | Thr | Tyr | His | Glu | Glu | Thr | Arg | Glu | Thr | Leu | Ile |
|---|---|---|---|---|---|---|---|---|---|---|---|---|---|---|---|
| | | | 450 | | | | | 455 | | | | | 460 | | |

| Leu | Asp | Ser | Glu | Ile | Thr | Ile | Glu | Asn | Asp | Pro | Glu | Ser | Glu | Lys | Arg |
|---|---|---|---|---|---|---|---|---|---|---|---|---|---|---|---|
| 465 | | | | 470 | | | | | 475 | | | | | 480 | |

| Gln | Lys | Leu | Phe | Pro | Ser | Lys | Gly | Glu |
|---|---|---|---|---|---|---|---|---|
| | | | | 485 | | | | |

<210> SEQ ID NO 3
<211> LENGTH: 1470
<212> TYPE: DNA
<213> ORGANISM: Bacillus subtilis

<400> SEQUENCE: 3

| atgactcatc | aaatagtaac | gactcaatac | ggcaaagtaa | aaggcacaac | ggaaaacggc | 60 |
|---|---|---|---|---|---|---|
| gtacataagt | ggaaaggcat | ccctatgcc | aagccgcctg | tcggacaatg | gcgttttaaa | 120 |
| gcacctgagc | cgcctgaagt | gtgggaagat | gtccttgatg | ccacagcgta | cggccctatt | 180 |
| tgcccgcagc | cgtctgattt | gctctcactg | tcgtatacag | agctgccccg | ccagtccgag | 240 |
| gattgcttgt | atgtcaatgt | atttgcgcct | gacaccccaa | gtcaaaatct | tcctgtcatg | 300 |
| gtgtggattc | acggaggcgc | tttttatctt | ggagcgggca | gtgagccatt | gtatgacgga | 360 |
| tcaaaacttg | cggcacaggg | agaagtcatt | gtcgttacat | gaactatcg | gctgggccg | 420 |
| tttggctttt | tgcacttgtc | ttcgtttgat | gaggcgtatt | ccgataacct | tgggctttta | 480 |
| gaccaagccg | ccgcactgaa | atgggtgcgg | gagaatattt | cagcgtttgg | cggtgatccc | 540 |
| gataacgtaa | cagtatttgg | agaatccgcc | ggcgggatga | gcattgccgc | gcttctcgct | 600 |
| atgcctgcgg | caaaaggcct | gttccagaaa | gcaatcatgg | aaagcggcgc | ttctcgaacg | 660 |
| atgacgaaag | aacaagcggc | gagcacctcg | gcagcctttt | tacaggtcct | tgggattaac | 720 |
| gagggccaat | ggataaaatt | gcatacggtt | tctgcagaag | atttgctaaa | gcggctgat | 780 |
| cagcttcgga | ttgcagaaaa | agaaaatatc | tttcagctgt | tcttccagcc | cgcccttgat | 840 |
| ccaaaaacgc | tgcctgctga | accagaaaaa | gcgatctcag | aaggggctgc | ttccggcatt | 900 |
| cctctattga | ttgaacaac | ccgtgatgaa | ggatatttat | ttttcacccc | ggattcagac | 960 |
| gttcattctc | aggaaacgct | tgatgcagca | ctcgagtatt | tactagggaa | gccgctggca | 1020 |
| gagaaagctg | ccgatttgta | tccgcgttct | ctggaaagcc | aaattcatat | gatgactgat | 1080 |
| ttattatttt | ggcgccctgc | cgtcgcctat | gcatccgcac | agtctcatta | cgcccctgtc | 1140 |
| tggatgtaca | ggttcgattg | gcacccgaag | aagccgccgt | acaataaagc | gtttcacgca | 1200 |
| ttagagcttc | cttttgtctt | tggaaatctg | gacggattgg | aacgaatggc | aaaagcggag | 1260 |
| attacggatg | aggtgaaaca | gctttctcac | acgatacaat | cagcgtggat | cacgttcgct | 1320 |
| aaaacaggaa | acccaagcac | cgaagctgtg | aattggccga | cgtatcatga | agaaacgaga | 1380 |
| gagacgctga | ttttagattc | agagattacg | atcgaaaacg | atcccgaatc | tgaaaaaagg | 1440 |
| cagaagctat | tcccttcaaa | aggagaataa | | | | 1470 |

<210> SEQ ID NO 4
<211> LENGTH: 1470
<212> TYPE: DNA

<213> ORGANISM: Bacillus licheniformis

<400> SEQUENCE: 4

```
atgtctcata aaacagtaac aactcaatac ggcaaagtaa aaggcacaac agaaaacggc      60
gtacataaat ggaaaggcat ccctatgcc aaacctcctg tcgggccatt gcgttttaaa     120
gcaccggaac tcctgaagc gtgggagaac gaactggacg caacagcata cggctctatt     180
tgcccgcagc cgtctgattt gctgtcactt tcgtatactg agctgccccg ccagtctgag     240
gattgcttgt atatcaatgt atttgcgcct gatactccaa gtcaaaacct gcctgtcatg    300
gtatggattc acggcggcgc ttttatctt ggagcgggca gtgagccatt atatgatggg     360
tcaagacttg cggcgcaggg agaagtcatt gtcgttacac tgaattatcg tctggggccg     420
tttggatttt tacatttgtc ttcgtttgaa gagacgtatt ccgataacct tgggcttttg     480
gaccaagccg ccgcactgaa atgggtgcga acaatatct cagcatttgg cggtgatccg      540
gataacgtaa cagtatttgg agaatcagca ggcggcatga gcattgccgc gctgctcgca    600
atgcctgcgg caaaaggcct gttccagaaa gcaatcatgg aaagtggcgc ttccagaacg    660
atgacaaaag aaaagcggc tagcaccgcg gcagccttt tagaggtcct tgggattgac      720
gagagccaat tggacaggtt gcatactgta tctgcggaag atttgcttaa agcggccgat    780
cagcttcgga agcagaaaa tgaaaatctc tttcagctgt tcttccagcc cgcccttgat    840
ccgaaaacgc tgcctgctga accagaaaaa gcgatcgcag agggtgctgc tgccggcatt    900
ccgctgttaa tcggaacaaa ccgcgatgaa ggatatttat ttttcacccc ggactcagac     960
gttcattctc aggaaacgtt tgatgccgcg cttgtgtatt tattagggca gccgctggca   1020
gagaaagccg ccgatctgta tccgcgttcg ctggaaagcc aaattcatat gatgactgat   1080
tgttattttt ggcgcccggc cgtcgcctgt gcctccgcac agtcccatta cgcgcctgtc   1140
tggatgtacc gattcgattg gcactctgat aagccgccgt ataataaagc gtttcacgca   1200
ttagagcttc ctttgtttt cggaaatctg acgggttag aacggatggc aaaagcagag   1260
attacggatg aagtgaaaca gctctctcac accatacaat cagcatggat cacgttcgcc   1320
aaaacaggga acccaagcac tgaagatgta aaatggccgg cgtatcatga ggaaacaaga   1380
gagacgctga ttttaaattc agagattgcg attgaaaacg accctgaagc tgaaaaaagg   1440
cagaaactat tcccttcaca aggagaataa                                    1470
```

<210> SEQ ID NO 5
<211> LENGTH: 518
<212> TYPE: PRT
<213> ORGANISM: Bacillus subtilis

<400> SEQUENCE: 5

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Met Thr His
            20                  25                  30

Gln Ile Val Thr Thr Gln Tyr Gly Lys Val Lys Gly Thr Thr Glu Asn
        35                  40                  45

Gly Val His Lys Trp Lys Gly Ile Pro Tyr Ala Lys Pro Pro Val Gly
    50                  55                  60

Gln Trp Arg Phe Lys Ala Pro Glu Pro Pro Glu Val Trp Glu Asp Val
65                  70                  75                  80

Leu Asp Ala Thr Ala Tyr Gly Pro Ile Cys Pro Gln Pro Ser Asp Leu
            85                  90                  95
```

```
Leu Ser Leu Ser Tyr Thr Glu Leu Pro Arg Gln Ser Glu Asp Cys Leu
            100                 105                 110
Tyr Val Asn Val Phe Ala Pro Asp Thr Pro Ser Gln Asn Leu Pro Val
            115                 120                 125
Met Val Trp Ile His Gly Gly Ala Phe Tyr Leu Gly Ala Gly Ser Glu
130                 135                 140
Pro Leu Tyr Asp Gly Ser Lys Leu Ala Ala Gln Gly Glu Val Ile Val
145                 150                 155                 160
Val Thr Leu Asn Tyr Arg Leu Gly Pro Phe Gly Phe Leu His Leu Ser
                165                 170                 175
Ser Phe Asp Glu Ala Tyr Ser Asn Leu Gly Leu Leu Asp Gln Ala
            180                 185                 190
Ala Ala Leu Lys Trp Val Arg Glu Asn Ile Ser Ala Phe Gly Gly Asp
            195                 200                 205
Pro Asp Asn Val Thr Val Phe Gly Glu Ser Ala Gly Gly Met Ser Ile
            210                 215                 220
Ala Ala Leu Leu Ala Met Pro Ala Ala Lys Gly Leu Phe Gln Lys Ala
225                 230                 235                 240
Ile Met Glu Ser Gly Ala Ser Arg Thr Met Thr Lys Glu Gln Ala Ala
                245                 250                 255
Ser Thr Ser Ala Ala Phe Leu Gln Val Leu Gly Ile Asn Glu Gly Gln
            260                 265                 270
Leu Asp Lys Leu His Thr Val Ser Ala Glu Asp Leu Leu Lys Ala Ala
            275                 280                 285
Asp Gln Leu Arg Ile Ala Glu Lys Glu Asn Ile Phe Gln Leu Phe Phe
            290                 295                 300
Gln Pro Ala Leu Asp Pro Lys Thr Leu Pro Ala Glu Pro Glu Lys Ala
305                 310                 315                 320
Ile Ser Glu Gly Ala Ala Ser Gly Ile Pro Leu Leu Ile Gly Thr Thr
                325                 330                 335
Arg Asp Glu Gly Tyr Leu Phe Phe Thr Pro Asp Ser Asp Val His Ser
            340                 345                 350
Gln Glu Thr Leu Asp Ala Ala Leu Glu Tyr Leu Leu Gly Lys Pro Leu
            355                 360                 365
Ala Glu Lys Ala Ala Asp Leu Tyr Pro Arg Ser Leu Glu Ser Gln Ile
            370                 375                 380
His Met Met Thr Asp Leu Leu Phe Trp Arg Pro Ala Val Ala Tyr Ala
385                 390                 395                 400
Ser Ala Gln Ser His Tyr Ala Pro Val Trp Met Tyr Arg Phe Asp Trp
                405                 410                 415
His Pro Lys Lys Pro Pro Tyr Asn Lys Ala Phe His Ala Leu Glu Leu
            420                 425                 430
Pro Phe Val Phe Gly Asn Leu Asp Gly Leu Glu Arg Met Ala Lys Ala
            435                 440                 445
Glu Ile Thr Asp Glu Val Lys Gln Leu Ser His Thr Ile Gln Ser Ala
            450                 455                 460
Trp Ile Thr Phe Ala Lys Thr Gly Asn Pro Ser Thr Glu Ala Val Asn
465                 470                 475                 480
Trp Pro Thr Tyr His Glu Glu Thr Arg Glu Thr Leu Ile Leu Asp Ser
                485                 490                 495
Glu Ile Thr Ile Glu Asn Asp Pro Glu Ser Glu Lys Arg Gln Lys Leu
            500                 505                 510
Phe Pro Ser Lys Gly Glu
            515
```

<210> SEQ ID NO 6
<211> LENGTH: 518
<212> TYPE: PRT
<213> ORGANISM: Bacillus licheniformis

<400> SEQUENCE: 6

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Met Thr His
            20                  25                  30

Gln Ile Val Thr Gln Tyr Gly Lys Val Lys Gly Thr Thr Glu Asn
        35                  40                  45

Gly Val His Lys Trp Lys Gly Ile Pro Tyr Ala Lys Pro Pro Val Gly
    50                  55                  60

Gln Trp Arg Phe Lys Ala Pro Glu Pro Pro Glu Val Trp Glu Asp Val
65              70                  75                  80

Leu Asp Ala Thr Ala Tyr Gly Pro Ile Cys Pro Gln Pro Ser Asp Leu
                85                  90                  95

Leu Ser Leu Ser Tyr Thr Glu Leu Pro Arg Gln Ser Glu Asp Cys Leu
            100                 105                 110

Tyr Val Asn Val Phe Ala Pro Asp Thr Pro Ser Gln Asn Leu Pro Val
        115                 120                 125

Met Val Trp Ile His Gly Gly Ala Phe Tyr Leu Gly Ala Gly Ser Glu
    130                 135                 140

Pro Leu Tyr Asp Gly Ser Lys Leu Ala Ala Gln Gly Glu Val Ile Val
145                 150                 155                 160

Val Thr Leu Asn Tyr Arg Leu Gly Pro Phe Gly Phe Leu His Leu Ser
                165                 170                 175

Ser Phe Asp Glu Ala Tyr Ser Asp Asn Leu Gly Leu Leu Asp Gln Ala
            180                 185                 190

Ala Ala Leu Lys Trp Val Arg Glu Asn Ile Ser Ala Phe Gly Gly Asp
        195                 200                 205

Pro Asp Asn Val Thr Val Phe Gly Glu Ser Ala Gly Gly Met Ser Ile
    210                 215                 220

Ala Ala Leu Leu Ala Met Pro Ala Ala Lys Gly Leu Phe Gln Lys Ala
225                 230                 235                 240

Ile Met Glu Ser Gly Ala Ser Arg Thr Met Thr Lys Glu Gln Ala Ala
                245                 250                 255

Ser Thr Ser Ala Ala Phe Leu Gln Val Leu Gly Ile Asn Glu Gly Gln
            260                 265                 270

Leu Asp Lys Leu His Thr Val Ser Ala Glu Asp Leu Leu Lys Ala Ala
        275                 280                 285

Asp Gln Leu Arg Ile Ala Glu Lys Glu Asn Ile Phe Gln Leu Phe Phe
    290                 295                 300

Gln Pro Ala Leu Asp Pro Lys Thr Leu Pro Ala Glu Pro Glu Lys Ala
305                 310                 315                 320

Ile Ser Glu Gly Ala Ala Ser Gly Ile Pro Leu Leu Ile Gly Thr Thr
                325                 330                 335

Arg Asp Glu Gly Tyr Leu Phe Phe Thr Pro Asp Ser Asp Val His Ser
            340                 345                 350

Gln Glu Thr Leu Asp Ala Ala Leu Glu Tyr Leu Leu Gly Lys Pro Leu
        355                 360                 365

Ala Glu Lys Ala Ala Asp Leu Tyr Pro Arg Ser Leu Glu Ser Gln Ile
    370                 375                 380
```

His Met Met Thr Asp Leu Leu Phe Trp Arg Pro Ala Val Ala Tyr Ala
385                 390                 395                 400

Ser Ala Gln Ser His Tyr Ala Pro Val Trp Met Tyr Arg Phe Asp Trp
            405                 410                 415

His Pro Lys Lys Pro Pro Tyr Asn Lys Ala Phe His Ala Leu Glu Leu
        420                 425                 430

Pro Phe Val Phe Gly Asn Leu Asp Gly Leu Glu Arg Met Ala Lys Ala
        435                 440                 445

Glu Ile Thr Asp Glu Val Lys Gln Leu Ser His Thr Ile Gln Ser Ala
    450                 455                 460

Trp Ile Thr Phe Ala Lys Thr Gly Asn Pro Ser Thr Glu Ala Val Asn
465                 470                 475                 480

Trp Pro Thr Tyr His Glu Glu Thr Arg Glu Thr Leu Ile Leu Asp Ser
            485                 490                 495

Glu Ile Thr Ile Glu Asn Asp Pro Glu Ser Glu Lys Arg Gln Lys Leu
        500                 505                 510

Phe Pro Ser Lys Gly Glu
        515

<210> SEQ ID NO 7
<211> LENGTH: 1557
<212> TYPE: DNA
<213> ORGANISM: Bacillus subtilis

<400> SEQUENCE: 7
atgatgagga aaaagagttt ttggcttggg atgctgacgg ccttcatgct cgtgttcacg      60
atggcattca gcgattccgc ttctgctatg actcatcaaa tagtaacgac tcaatacggc     120
aaagtaaaag gcacaacgga aaacggcgta cataagtgga aaggcatccc ctatgccaag     180
ccgcctgtcg acaatggcg tttttaaagca cctgagccgc tgaagtgtg gaagatgtc      240 cttgatgcca cagcgtacgg ccctattgc ccgcagccgt ctgatttgct ctcactgtcg     300
tatacagagc tgccccgcca gtccgaggat tgcttgtatg tcaatgtatt tgcgcctgac     360
accccaagtc aaaatcttcc tgtcatggtg tggattcacg gaggcgcttt ttatcttgga     420
gcgggcagtg agccattgta tgacggatca aaacttgcgg cacagggaga agtcattgtc     480
gttacattga actatcggct ggggccgttt ggcttttgc acttgtcttc gtttgatgag     540
gcgtattccg ataaccttgg ctttttagac caagccgccg cactgaaatg ggtgcgggag     600
aatatttcag cgtttggcgg tgatcccgat aacgtaacag tatttggaga atccgccggc     660
gggatgagca ttgccgcgct ctcgctatg cctgcggcaa aaggcctgtt ccagaaagca     720
atcatggaaa gcggcgcttc tcgaacgatg acgaaagaac aagcggcgag cacctcggca     780 gccttttac aggtccttgg gattaacgag ggccaattgg ataaattgca tacggtttct     840
gcagaagatt tgctaaaagc ggctgatcag cttcggattg cagaaaaaga aaatatcttt     900
cagctgttct tccagcccgc ccttgatcca aaaacgctgc tgctgaacc agaaaaagcg     960 atctcagaag gggctgcttc cggcattcct ctattgattg aacaacccg tgatgaagga    1020 tattattttt tcaccccgga ttcagacgtt cattctcagg aaacgcttga tgcagcactc    1080
gagtatttac tagggaagcc gctggcagag aaagctgccg attttgtatcc gcgttctctg    1140 gaaagccaaa ttcatatgat gactgattta ttattttggc gccctgccgt cgcctatgca    1200
tccgcacagt ctcattacgc ccctgtctgg atgtacaggt tcgattggca cccgaagaag    1260
ccgccgtaca ataaagcgtt tcacgcatta gagcttcctt ttgtctttgg aaatctggac    1320

| ggattggaac gaatggcaaa agcggagatt acggatgagg tgaaacagct ttctcacacg | 1380 |
| atacaatcag cgtggatcac gttcgctaaa acaggaaacc caagcaccga agctgtgaat | 1440 |
| tggccgacgt atcatgaaga aacgagagag acgctgattt tagattcaga gattacgatc | 1500 |
| gaaaacgatc ccgaatctga aaaaaggcag aagctattcc cttcaaaagg agaataa | 1557 |

<210> SEQ ID NO 8
<211> LENGTH: 1557
<212> TYPE: DNA
<213> ORGANISM: Bacillus licheniformis

<400> SEQUENCE: 8

| atgatgagga aaagagtttt ttggcttggg atgctgacgg ccttcatgct cgtgttcacg | 60 |
| atggcattca gcgattccgc ttctgctatg tctcataaaa cagtaacaac tcaatacggc | 120 |
| aaagtaaaag gcacaacaga aaacggcgta cataaatgga aaggcatccc ctatgccaaa | 180 |
| cctcctgtcg ggccattgcg ttttaaagca ccggaacctc ctgaagcgtg ggagaacgaa | 240 |
| ctggacgcaa cagcatacgg ctctatttgc ccgcagccgt ctgatttgct gtcactttcg | 300 |
| tatactgagc tgccccgcca gtctgaggat tgcttgtata tcaatgtatt tgcgcctgat | 360 |
| actccaagtc aaaacctgcc tgtcatggta tggattcacg gcggcgcttt ttatcttgga | 420 |
| gcgggcagtg agccattata tgatgggtca agacttgcgg cgcagggaga agtcattgtc | 480 |
| gttacactga attatcgtct ggggccgttt ggattttttac atttgtcttc gtttgaagag | 540 |
| acgtattccg ataaccttgg gcttttggac caagccgccg cactgaaatg ggtgcgagac | 600 |
| aatatctcag catttggcgg tgatccggat aacgtaacag tatttggaga atcagcaggc | 660 |
| ggcatgagca ttgccgcgct gctcgcaatg cctgcggcaa aaggcctgtt ccagaaagca | 720 |
| atcatggaaa gtggcgcttc cagaacgatg acaaaagaaa aagcggctag caccgcggca | 780 |
| gcctttttag aggtccttgg gattgacgag agccaattgg acaggttgca tactgtatct | 840 |
| gcggaagatt tgcttaaagc ggccgatcag cttcggaaag cagaaaatga aaatctcttt | 900 |
| cagctgttct tccagcccgc ccttgatccg aaaacgctgc ctgctgaacc agaaaaagcg | 960 |
| atcgcagagg gtgctgctgc cggcattccg ctgttaatcg gaacaaaccg cgatgaagga | 1020 |
| tattttatttt tcaccccgga ctcagacgtt cattctcagg aaacgtttga tgccgcgctt | 1080 |
| gtgtatttat tagggcagcc gctggcagag aaagccgccg atctgtatcc gcgttcgctg | 1140 |
| gaaagccaaa ttcatatgat gactgatttg ttatttttggc gcccggccgt cgcctgtgcc | 1200 |
| tccgcacagt cccattacgc gcctgtctgg atgtaccgat tcgattggca ctctgataag | 1260 |
| ccgccgtata ataaagcgtt tcacgcatta gagcttcctt ttgttttcgg aaatctggac | 1320 |
| gggttagaac ggatggcaaa agcagagatt acggatgaag tgaaacagct ctctcacacc | 1380 |
| atacaatcag catggatcac gttcgccaaa acagggaacc caagcactga agatgtaaaa | 1440 |
| tggccggcgt atcatgagga aacaagagag acgctgattt taaattcaga gattgcgatt | 1500 |
| gaaaacgacc ctgaagctga aaaaaggcag aaactattcc cttcacaagg agaataa | 1557 |

<210> SEQ ID NO 9
<211> LENGTH: 29
<212> TYPE: PRT
<213> ORGANISM: Artificial
<220> FEATURE:
<223> OTHER INFORMATION: SIGNAL

<400> SEQUENCE: 9

Met Met Arg Lys Lys Ser Phe Trp Leu Gly Met Leu Thr Ala Phe Met
1               5                   10                  15

```
Leu Val Phe Thr Met Ala Phe Ser Asp Ser Ala Ser Ala
        20                  25
```

<210> SEQ ID NO 10
<211> LENGTH: 87
<212> TYPE: DNA
<213> ORGANISM: Artificial
<220> FEATURE:
<223> OTHER INFORMATION: sig_peptide

<400> SEQUENCE: 10

```
atgatgagga aaaagagttt ttggcttggg atgctgacgg ccttcatgct cgtgttcacg    60
atggcattca gcgattccgc ttctgct                                        87
```

<210> SEQ ID NO 11
<211> LENGTH: 489
<212> TYPE: PRT
<213> ORGANISM: Bacillus subtilis

<400> SEQUENCE: 11

```
Met Thr His Gln Ile Val Thr Thr Gln Tyr Gly Lys Val Lys Gly Thr
 1               5                  10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Ser Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asn Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285
```

```
Glu Lys Ala Ile Ala Glu Gly Ala Ser Gly Ile Pro Leu Leu Ile
    290             295             300

Gly Thr Thr Arg Asp Glu Gly Tyr Leu Phe Thr Pro Asp Ser Asp
305             310             315             320

Val His Ser Gln Glu Thr Leu Asp Ala Ala Leu Glu Tyr Leu Gly
                325             330             335

Lys Pro Leu Ala Glu Lys Val Ala Asp Leu Tyr Pro Arg Ser Leu Glu
        340             345             350

Ser Gln Ile His Met Met Thr Asp Leu Leu Phe Trp Arg Pro Ala Val
        355             360             365

Ala Tyr Ala Ser Ala Gln Ser His Tyr Ala Pro Val Trp Met Tyr Arg
370             375             380

Phe Asp Trp His Pro Lys Lys Pro Pro Tyr Asn Lys Ala Phe His Ala
385             390             395             400

Leu Glu Leu Pro Phe Val Phe Gly Asn Leu Asp Gly Leu Glu Arg Met
                405             410             415

Ala Lys Ala Glu Ile Thr Asp Glu Val Lys Gln Leu Ser His Thr Ile
        420             425             430

Gln Ser Ala Trp Ile Thr Phe Ala Lys Thr Gly Asn Pro Ser Thr Glu
        435             440             445

Ala Val Asn Trp Pro Ala Tyr His Glu Glu Thr Arg Glu Thr Leu Ile
450             455             460

Leu Asp Ser Glu Ile Thr Ile Glu Asn Asp Pro Glu Ser Glu Lys Arg
465             470             475             480

Gln Lys Leu Phe Pro Ser Lys Gly Glu
            485

<210> SEQ ID NO 12
<211> LENGTH: 490
<212> TYPE: PRT
<213> ORGANISM: Bacillus licheniformis

<400> SEQUENCE: 12

Met Tyr Asp Thr Thr Val Glu Thr Arg Phe Gly Lys Leu Lys Gly Arg
1               5               10              15

Ala Glu Asn Gly Val Arg Ile Phe Lys Gly Val Pro Tyr Ala Lys Pro
            20              25              30

Pro Val Gly Asp Leu Arg Phe Arg Glu Pro Gln Arg Met Glu Ala Trp
        35              40              45

Glu Gly Glu Leu Asp Ala Phe Gln Phe Gly Pro Val Cys Pro Gln Pro
    50              55              60

Asp Gly Val Leu Pro Glu Ser Ala Gly Val Gln Lys Ser Glu Asp Cys
65              70              75              80

Leu Tyr Leu Asn Val Tyr Ala Pro Glu Glu Ala Asp Gly Asp Leu Pro
                85              90              95

Val Met Val Trp Ile His Gly Gly Ala Phe Tyr Arg Gly Ala Gly Ser
            100             105             110

Glu Pro Leu Tyr Asp Gly Thr Gln Leu Ala Lys Gln Gly Lys Val Ile
        115             120             125

Val Val Thr Ile Asn Tyr Arg Leu Gly Pro Phe Gly Phe Leu His Leu
    130             135             140

Ser Ser Ile Asp Asp Ser Tyr Ser Ser Asn Leu Gly Leu Leu Asp Gln
145             150             155             160

Ile Ala Ala Leu Glu Trp Val Lys Asp Asn Ile Ala Phe Phe Gly Gly
                165             170             175
```

-continued

```
Asp Arg His His Ile Thr Val Phe Gly Glu Ser Ala Gly Ser Met Ser
            180                 185                 190

Ile Ala Ser Leu Leu Ala Met Pro Lys Ala Lys Gly Leu Phe Gln Gln
    195                 200                 205

Ala Ile Met Glu Ser Gly Ala Ser Ala Thr Met Ser Asp Lys Leu Ala
210                 215                 220

Lys Ala Ala Ala Glu Arg Phe Leu Arg Ile Leu Asp Ile Asp His His
225                 230                 235                 240

His Leu Glu Arg Leu His Asp Val Ser Asp Gln Glu Leu Leu Glu Ala
                245                 250                 255

Ala Asp Gln Leu Arg Thr Leu Met Gly Glu Asn Ile Phe Glu Leu Ile
            260                 265                 270

Phe Leu Pro Ala Leu Asp Glu Lys Thr Leu Pro Leu Lys Pro Glu Val
        275                 280                 285

Ala Val Ala Lys Gly Ala Ala Lys Glu Ile Asn Leu Leu Ile Gly Thr
    290                 295                 300

Asn Arg Asp Glu Gly Val Leu Phe Phe Pro Ser Asp Ser Asp Leu Leu
305                 310                 315                 320

Pro Glu Ser Lys Ile Asn Glu Ile Leu Glu Glu Tyr Met Gly Lys Glu
                325                 330                 335

Ala Ala Glu Ala Ala Ser Ser Leu Tyr Pro Arg Ser Leu Glu Gly His
            340                 345                 350

Val Asp Met Met Thr Asp Leu Ile Phe Trp His Pro Ser Val Val Phe
        355                 360                 365

Ala Ser Ala Gln Ser Arg Tyr Ala Ser Val Phe Met Tyr Arg Phe Asp
    370                 375                 380

Trp His Ala Asp Ser Glu Gln Pro Pro Phe Asn Lys Ala Ala His Gly
385                 390                 395                 400

Leu Glu Ile Pro Phe Val Phe Gly Asn Met Asp Ile Leu Glu Gln Leu
                405                 410                 415

Thr Gly Thr Lys Ala Gly Glu Glu Ala Gln Leu Leu Ala Glu Gln Ile
            420                 425                 430

Gln Ala Ala Trp Val Ser Phe Ala Arg Ser Gly Asn Pro Ser Thr Asp
        435                 440                 445

Asp Val Ser Trp Pro Asp Tyr Asp Glu Asp Ser Arg Lys Thr Leu Ile
    450                 455                 460

Phe Asp Gln Glu Val Ala Val Glu Ser Asp Pro Tyr Ser Asp Lys Arg
465                 470                 475                 480

Lys Met Leu Thr Ala Pro Asn Pro Gln Ile
                485                 490

<210> SEQ ID NO 13
<211> LENGTH: 489
<212> TYPE: PRT
<213> ORGANISM: Bacillus subtilis

<400> SEQUENCE: 13

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Val Cys Pro Gln Pro
        50                  55                  60
```

```
Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Ser Asp Ser Asp
305                 310                 315                 320

Val Arg Ser Gln Glu Thr Leu Asp Ala Ala Leu Glu Tyr Ser Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

<210> SEQ ID NO 14
<211> LENGTH: 489
<212> TYPE: PRT
<213> ORGANISM: Bacillus subtilis

<400> SEQUENCE: 14

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335

Lys Pro Leu Ala Glu Lys Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala Gln Ser His Tyr Ala Pro Val Trp Met Tyr Arg
    370                 375                 380
```

```
Phe Asp Trp His Pro Glu Lys Pro Tyr Asn Lys Ala Phe His Ala
385                 390                 395                 400

Leu Glu Leu Pro Phe Val Phe Gly Asn Leu Asp Gly Leu Glu Arg Met
            405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Val Ile
            450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 15
<211> LENGTH: 489
<212> TYPE: PRT
<213> ORGANISM: Bacillus subtilis

<400> SEQUENCE: 15

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Ser Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asn Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270
```

```
Leu Phe Phe Gln Pro Ala Leu Asp Pro Lys Thr Leu Pro Glu Glu Pro
        275                 280                 285

Glu Lys Ala Ile Ala Glu Gly Ala Ser Gly Ile Pro Leu Leu Ile
290                 295                 300

Gly Thr Thr Arg Asp Glu Gly Tyr Leu Phe Thr Pro Asp Ser Asp
305                 310                 315                 320

Val His Ser Gln Glu Thr Leu Asp Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Met Thr Asp Leu Leu Phe Trp Arg Pro Ala Val
            355                 360                 365

Ala Tyr Ala Ser Ala Gln Ser His Tyr Ala Pro Val Trp Met Tyr Arg
370                 375                 380

Phe Asp Trp His Pro Lys Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Leu Ile
450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 16
<211> LENGTH: 489
<212> TYPE: PRT
<213> ORGANISM: Bacillus subtilis

<400> SEQUENCE: 16

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Ser Ile Cys Pro Gln Pro
        50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Leu
        130                 135                 140

His Leu Ser Ser Phe Asn Glu Ala Tyr Ser Asp Asn Leu Gly Leu Leu
145                 150                 155                 160
```

```
Asp Gln Ala Ala Ala Leu Lys Trp Val Arg Glu Asn Ile Ser Ala Phe
            165                 170                 175

Gly Gly Asp Pro Asp Asn Val Thr Val Phe Gly Ser Ala Gly Gly
        180                 185                 190

Met Ser Ile Ala Ala Leu Leu Ala Met Pro Ala Ala Lys Gly Leu Phe
            195                 200                 205

Gln Lys Ala Ile Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
    275                 280                 285

Glu Lys Ala Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
                340                 345                 350

Ser Gln Ile His Met Met Thr Asp Leu Leu Phe Trp Arg Pro Ala Val
            355                 360                 365

Ala Tyr Ala Ser Ala Gln Ser His Tyr Ala Pro Val Trp Met Tyr Arg
            370                 375                 380

Phe Asp Trp His Pro Lys Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
    435                 440                 445

Ala Val Asn Trp Pro Ala Tyr His Glu Glu Thr Arg Glu Thr Leu Ile
450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 17
<211> LENGTH: 489
<212> TYPE: PRT
<213> ORGANISM: Bacillus subtilis

<400> SEQUENCE: 17

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45
```

-continued

Glu Asp Val Leu Asp Ala Thr Ala Tyr Gly Ser Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                    85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Leu
    130                 135                 140

His Leu Ser Ser Phe Asn Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                    165                 170                 175

Gly Gly Asp Pro Asp Asn Val Thr Val Phe Gly Glu Ser Ala Gly Gly
                180                 185                 190

Met Ser Ile Ala Ala Leu Leu Ala Met Pro Ala Ala Lys Gly Leu Phe
            195                 200                 205

Gln Lys Ala Ile Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                    245                 250                 255

Lys Ala Ala Asp Gln Leu Arg Ile Ala Glu Lys Glu Asn Ile Phe Gln
                260                 265                 270

Leu Phe Phe Gln Pro Ala Leu Asp Pro Lys Thr Leu Pro Glu Glu Pro
            275                 280                 285

Glu Lys Ala Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                    325                 330                 335

Lys Pro Leu Ala Glu Lys Val Ala Asp Leu Tyr Pro Arg Ser Leu Glu
                340                 345                 350

Ser Gln Ile His Met Met Thr Asp Leu Leu Phe Trp Arg Pro Ala Val
            355                 360                 365

Ala Tyr Ala Ser Ala Gln Ser His Tyr Ala Pro Val Trp Met Tyr Arg
    370                 375                 380

Phe Asp Trp His Pro Lys Lys Pro Pro Tyr Asn Lys Ala Phe His Ala
385                 390                 395                 400

Leu Glu Leu Pro Phe Val Phe Gly Asn Leu Asp Gly Leu Glu Arg Met
                    405                 410                 415

Ala Lys Ala Glu Ile Thr Asp Glu Val Lys Gln Leu Ser His Thr Ile
                420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Leu Ile
    450                 455                 460

Leu Asp Ser Glu Ile Thr Ile Glu Asn Asp Pro Glu Ser Glu Lys Arg

```
                    465                 470                 475                 480
Gln Lys Leu Phe Pro Ser Lys Gly Glu
                485

<210> SEQ ID NO 18
<211> LENGTH: 489
<212> TYPE: PRT
<213> ORGANISM: Bacillus subtilis

<400> SEQUENCE: 18

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Ser Ile Cys Pro Gln Pro
50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
130                 135                 140

His Leu Ser Ser Phe Asn Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ala Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Met Thr Asp Leu Leu Phe Trp Arg Pro Ala Val
```

```
                      355                 360                 365
Ala Tyr Ala Ser Ala Gln Ser His Tyr Ala Pro Val Trp Met Tyr Arg
            370                 375                 380

Phe Asp Trp His Pro Lys Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Leu Ile
        450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 19
<211> LENGTH: 490
<212> TYPE: PRT
<213> ORGANISM: Bacillus licheniformis

<400> SEQUENCE: 19

Met Tyr Asp Thr Thr Val Glu Thr Arg Phe Gly Lys Leu Lys Gly Arg
1               5                   10                  15

Ala Glu Asn Gly Val Arg Ile Phe Lys Gly Val Pro Tyr Ala Lys Pro
            20                  25                  30

Pro Val Gly Asp Leu Arg Phe Arg Glu Pro Gln Arg Met Glu Ala Trp
        35                  40                  45

Glu Gly Glu Leu Asp Ala Phe Gln Phe Gly Pro Val Cys Pro Gln Pro
    50                  55                  60

Asp Gly Val Leu Pro Glu Ser Ala Gly Val Gln Lys Ser Glu Asp Cys
65                  70                  75                  80

Leu Tyr Leu Asn Val Tyr Ala Pro Glu Glu Ala Asp Gly Asp Leu Pro
                85                  90                  95

Val Met Val Trp Ile His Gly Gly Ala Phe Tyr Arg Gly Ala Gly Ser
            100                 105                 110

Glu Pro Leu Tyr Asp Gly Thr Gln Leu Ala Lys Gln Gly Lys Val Ile
        115                 120                 125

Val Val Thr Ile Asn Tyr Arg Leu Gly Pro Phe Gly Phe Leu His Leu
    130                 135                 140

Ser Ser Ile Asp Asp Ser Tyr Ser Ser Asn Leu Gly Leu Leu Asp Gln
145                 150                 155                 160

Ile Ala Ala Leu Glu Trp Val Lys Asp Asn Ile Ala Phe Phe Gly Gly
                165                 170                 175

Asp Arg His His Ile Thr Val Phe Gly Glu Ser Ala Gly Ser Met Ser
            180                 185                 190

Ile Ala Ser Leu Leu Ala Met Pro Lys Ala Lys Gly Leu Phe Gln Gln
        195                 200                 205

Ala Ile Met Glu Ser Gly Ala Ser Ala Thr Met Ser Asp Lys Leu Ala
    210                 215                 220

Lys Ala Ala Ala Glu Arg Phe Leu Arg Ile Leu Asp Ile Asp His His
225                 230                 235                 240

His Leu Glu Arg Leu His Asp Val Ser Asp Gln Glu Leu Leu Glu Ala
```

```
                    245                 250                 255
Ala Asp Gln Leu Arg Thr Leu Met Gly Glu Asn Ile Phe Glu Leu Ile
            260                 265                 270

Phe Leu Pro Ala Leu Asp Glu Lys Thr Leu Pro Leu Lys Pro Glu Val
            275                 280                 285

Ala Val Ala Lys Gly Ala Lys Glu Ile Asn Leu Leu Ile Gly Thr
            290                 295                 300

Asn Arg Asp Glu Gly Val Leu Phe Phe Pro Ser Asp Ser Asp Leu Leu
305                 310                 315                 320

Pro Glu Ser Lys Ile Asn Glu Ile Leu Glu Glu Tyr Met Gly Lys Glu
                    325                 330                 335

Ala Ala Glu Ala Ala Ser Ser Leu Tyr Pro Arg Ser Leu Glu Gly His
            340                 345                 350

Val Asp Met Met Thr Asp Leu Ile Phe Trp His Pro Ser Val Val Phe
            355                 360                 365

Ala Ser Ala Gln Ser Arg Tyr Ala Ser Val Phe Met Tyr Arg Phe Asp
            370                 375                 380

Trp His Ala Asp Ser Glu Gln Pro Pro Phe Asn Lys Ala Ala His Gly
385                 390                 395                 400

Leu Glu Ile Pro Phe Val Phe Gly Asn Met Asp Ile Leu Glu Gln Leu
                    405                 410                 415

Thr Gly Thr Lys Ala Gly Glu Glu Ala Gln Leu Leu Ala Glu Gln Ile
            420                 425                 430

Gln Ala Ala Trp Val Ser Phe Ala Arg Ser Gly Asn Pro Ser Thr Asp
            435                 440                 445

Asp Val Ser Trp Pro Asp Tyr Asp Glu Asp Ser Arg Lys Thr Leu Ile
            450                 455                 460

Phe Asp Gln Glu Val Ala Val Glu Ser Asp Pro Tyr Ser Asp Lys Arg
465                 470                 475                 480

Lys Met Leu Thr Ala Pro Asn Pro Gln Ile
                    485                 490

<210> SEQ ID NO 20
<211> LENGTH: 455
<212> TYPE: PRT
<213> ORGANISM: Staphylococcus  epidermidis

<400> SEQUENCE: 20

Met Cys Ser Asn Met Val Gln Val Lys Ile Gly Asn Cys Thr Ile Asn
1               5                   10                  15

Gly Leu His Lys Lys Asn Ile Asp Val Phe Leu Gly Ile Pro Tyr Ala
            20                  25                  30

Lys Ser Phe Asn Lys Ile Ser Arg Phe Gln His Ser Lys Leu Met Glu
        35                  40                  45

Leu Ser Lys Pro Met Ile Asp Ala Thr His Ile Gln Ser Ile Pro Pro
    50                  55                  60

Gln Pro Tyr Asn Ser Leu Glu Asp Phe Phe Ser Met Thr Asp Ser Ser
65                  70                  75                  80

Phe Asn Ser Phe Lys Gln Asn Asp Tyr Cys Leu Phe Leu Asn Ile Trp
                85                  90                  95

Lys Pro Ser Ser Asn Gln Asn His Leu Pro Val Val Ile Tyr Phe Tyr
            100                 105                 110

Gly Gly Ser Phe Leu Gln Gly His Gly Thr Ala Glu Leu Tyr Cys Pro
        115                 120                 125

Glu His Ile Val Glu Gln Glu Asn Ile Ile Val Val Thr Phe Asn Tyr
```

```
                130                 135                 140
Arg Leu Gly Ala Leu Gly Tyr Leu Asp Trp Ser Tyr Phe Asn Gln His
145                 150                 155                 160

Leu Asn Tyr Asn Asn Gly Ile Ser Asp Gln Ile Asn Val Leu Arg Trp
                165                 170                 175

Val His Gln Tyr Ile Glu His Phe Gly Gly Asp Ser Asn Asn Val Thr
            180                 185                 190

Leu Met Gly Gln Ser Ala Gly Ser Met Ser Ile Met Thr Leu Met Gln
        195                 200                 205

Met Pro Glu Leu Asp Asp Tyr Tyr His Lys Val Met Leu Leu Ser Gly
210                 215                 220

Thr Leu Thr Thr Asp Thr Pro Leu Asn Ala His Thr Lys Val Gln His
225                 230                 235                 240

Phe Ser Gln Leu Met Arg His Tyr Phe Pro Asn Lys Thr Leu Lys Thr
                245                 250                 255

Leu Thr Ser Asp Asp Ile Leu Tyr Leu Met Glu Ser Gln Lys Ile Glu
            260                 265                 270

Arg Gly Arg Ser Arg Gly Leu Asp Leu Ile Tyr Gln Pro Ile Lys Asp
        275                 280                 285

His His Met Ser Arg Ser Ile Lys Lys Phe Pro Lys Pro Thr Phe Met
290                 295                 300

Ser Tyr Thr His Asp Glu Gly Asp Ile Tyr Ile Glu Asp Ala Thr Arg
305                 310                 315                 320

Thr Leu Pro Ser Glu Arg Phe Ile His Leu Met Ser Gln Tyr Gly Thr
                325                 330                 335

His Val Glu Lys Asn Asp Ala Leu Thr Met Lys Gln Gln Arg Asn Leu
            340                 345                 350

Ile Thr Glu Tyr Cys Phe Val Arg Pro Ile Tyr Leu Phe Leu Asn Lys
        355                 360                 365

Met Asn Ser Cys Asp Thr Trp Leu Ala Arg Phe Asp Trp His Gln Pro
370                 375                 380

His Thr Ser Tyr Phe Lys Ser Ala Tyr His Ile Leu Asp Leu Val Phe
385                 390                 395                 400

Trp Phe Gly His Leu Ser Ile Leu Thr Lys Asn His Tyr Ser Ile Thr
                405                 410                 415

Gln His Asp Met Asn Leu Ser Arg Asn Met Ile Ser Asp Leu Ala Tyr
            420                 425                 430

Phe Ala Arg Lys Gly Lys Met Pro Trp Lys Cys Tyr Glu Pro Gln His
        435                 440                 445

Gln Ala Leu His Ile Tyr Arg
450                 455

<210> SEQ ID NO 21
<211> LENGTH: 450
<212> TYPE: PRT
<213> ORGANISM: Staphylococcus aureus

<400> SEQUENCE: 21

Met Lys Ile Asn Thr Thr Gly Gly Gln Ile His Gly Ile Thr Gln Asp
1               5                   10                  15

Gly Leu Asp Ile Phe Leu Gly Ile Pro Tyr Ala Glu Pro Val His
            20                  25                  30

Asp Asn Arg Phe Lys His Ser Thr Leu Lys Thr Gln Trp Ser Glu Pro
        35                  40                  45

Ile Asp Ala Thr Glu Ile Gln Pro Ile Pro Pro Gln Pro Asp Asn Lys
```

-continued

```
                    50                  55                  60
Leu Glu Asp Phe Phe Ser Ser Gln Ser Thr Thr Phe Thr Glu His Glu
 65                  70                  75                  80

Asp Cys Leu Tyr Leu Asn Ile Trp Lys Gln His Asn Asp Gln Thr Lys
                 85                  90                  95

Lys Pro Val Ile Ile Tyr Phe Tyr Gly Gly Ser Phe Glu Asn Gly His
            100                 105                 110

Gly Lys Ala Glu Leu Tyr Gln Pro Ala His Leu Val Gln Asn Asn Asp
            115                 120                 125

Ile Ile Val Ile Thr Cys Asn Tyr Arg Leu Gly Ala Leu Gly Tyr Leu
            130                 135                 140

Asp Trp Ser Tyr Phe Asn Lys Asp Phe His Ser Asn Asn Gly Leu Ser
145                 150                 155                 160

Asp Gln Ile Asn Val Ile Lys Trp Val His Gln Phe Ile Glu Ser Phe
                165                 170                 175

Gly Gly Asp Ala Asn Asn Ile Thr Leu Met Gly Gln Ser Ala Gly Ser
            180                 185                 190

Met Ser Ile Leu Thr Leu Leu Lys Ile Pro Asp Ile Glu Pro Tyr Phe
        195                 200                 205

His Lys Val Val Leu Leu Ser Gly Ala Leu Arg Leu Asp Thr Leu Glu
        210                 215                 220

Ser Ala Arg Asn Lys Ala Gln His Phe Gln Lys Met Met Leu Asp Tyr
225                 230                 235                 240

Leu Asp Thr Asp Asp Val Thr Ser Leu Ser Thr Asn Asp Ile Leu Met
                245                 250                 255

Leu Met Ala Lys Leu Lys Gln Ser Arg Gly Pro Ser Lys Gly Leu Asp
            260                 265                 270

Leu Ile Tyr Ala Pro Ile Lys Thr Asp Tyr Ile Gln Asn Asn Tyr Pro
            275                 280                 285

Thr Thr Lys Pro Ile Phe Ala Cys Tyr Thr Lys Asp Glu Gly Asp Ile
            290                 295                 300

Tyr Ile Thr Ser Glu Gln Lys Lys Leu Ser Pro Gln Arg Phe Ile Asp
305                 310                 315                 320

Ile Met Glu Leu Asn Asp Ile Pro Leu Lys Tyr Glu Asp Val Gln Thr
                325                 330                 335

Ala Lys Gln Gln Ser Leu Ala Ile Thr His Cys Tyr Phe Lys Gln Pro
            340                 345                 350

Met Lys Gln Phe Leu Gln Gln Leu Asn Ile Gln Asp Ser Asn Ala Gln
            355                 360                 365

Leu Trp Leu Ala Glu Phe Ala Trp His Asp Thr Ser Ser Ala His Tyr
            370                 375                 380

Arg Ser Ala Tyr His Ile Leu Asp Met Val Phe Trp Phe Gly Asn Leu
385                 390                 395                 400

Gln Ile Leu Ala Ala His Gln Tyr Pro Thr Thr Ala His Leu Lys Phe
                405                 410                 415

Leu Ser Arg Gln Met Gln Asn Asp Leu Ala Asn Phe Ala Lys Ser Gly
            420                 425                 430

Lys Met Pro Trp Pro Met Tyr His Asn Glu Arg Arg Tyr Tyr Arg Thr
            435                 440                 445

Tyr Gln
    450

<210> SEQ ID NO 22
<211> LENGTH: 492
```

```
<212> TYPE: PRT
<213> ORGANISM: Streptomyces avermitilis

<400> SEQUENCE: 22

Met Arg Gly Arg Leu Glu Gly Gly Leu Ala Val Phe Arg Gly Val Pro
1               5                   10                  15

Phe Ala Glu Pro Pro Val Gly Asp Ala Arg Phe Ala Ala Pro Arg Pro
            20                  25                  30

Val Arg Ala Trp Asp Gly Thr Arg Asp Ala Phe Ala Phe Gly Pro Pro
        35                  40                  45

Pro Pro Gln Glu Thr Gly Ile Gln Gly Arg Ala Ala Leu Leu Asp Ala
    50                  55                  60

Pro Thr Gly Asp Asp Trp Leu Thr Val Asn Val Trp Thr Pro Asp Pro
65                  70                  75                  80

Asp Pro Gly Ala Arg Arg Pro Val Met Val Trp Ile Tyr Gly Gly Ala
                85                  90                  95

Tyr Lys Leu Gly His Ser Gly Ser Pro Gly Tyr Asp Ala Arg Arg Ile
            100                 105                 110

Ala Arg Asp Gly Asp Val Val Val Thr Leu Asn Tyr Arg Val Gly
        115                 120                 125

Ile Glu Gly Phe Ala Arg Val Asp Gly Ala Pro Ala Asn Arg Gly Leu
130                 135                 140

Leu Asp Gln Val Ala Ala Leu Glu Trp Val Arg Glu Asn Ile Thr Ala
145                 150                 155                 160

Phe Gly Gly Asp Pro Gly Arg Val Thr Val Phe Gly Glu Ser Ala Gly
                165                 170                 175

Ala Gly Ser Ile Ala Ser Leu Leu Ala Met Pro Ser Ala Ser Gly Leu
            180                 185                 190

Phe Arg Arg Ala Ile Ala Gln Ser Val Pro Gly Thr Tyr Phe Ser Asp
        195                 200                 205

Glu Leu Ala Lys Asp Ile Ala Ala Ile Ala Ala Glu Ala Gly Leu
    210                 215                 220

Arg Pro Thr Ala Ala Asp Leu Ser Thr Val Asp Pro Arg Gln Leu Pro
225                 230                 235                 240

Ala Ala Gly Glu Ala Leu Ala Ala Thr Met Arg Gln Tyr Glu Asp Arg
                245                 250                 255

Trp Gly Pro Val Val His Thr Leu Thr Pro Phe Ser Pro Val Val Asp
            260                 265                 270

Gly Glu Val Leu Pro Thr Thr Pro Trp Gln Ala Leu Ala Ala Gly Thr
        275                 280                 285

Ala Arg Asp Val Glu Leu Ile Val Gly His Asn Ser Glu Glu Phe Arg
    290                 295                 300

Leu Phe Val Leu Leu Ser Gly Gln Leu Gly Lys Ile Thr Asp Gly Glu
305                 310                 315                 320

Ala Arg Ala Ala Leu Arg Arg Phe Gly Pro Gly Asp Ala Glu Gln
                325                 330                 335

Ala Tyr Arg Thr Gly Phe Pro Asp Ala Ser Pro Gly Glu Leu Tyr Glu
            340                 345                 350

Arg Val Met Ser Asp Trp Leu Phe His Met Pro Ser Leu His Leu Ala
        355                 360                 365

Glu Ala Gln Leu Thr Gly Gly Gly Arg Ala His Val Tyr Glu Leu Thr
    370                 375                 380

Trp Pro Ala Pro Gly Asn Gly Val Leu Gly Ala Cys His Gly Leu
385                 390                 395                 400
```

```
Asp Ile Pro Leu Leu Phe Gly Thr Phe Asp Ala Asp Leu Gly Ser Leu
                405                 410                 415

Leu Phe Ala Gly Thr Glu Pro Ser Pro Glu Ala Glu Ala Leu Ser Ser
            420                 425                 430

Arg Phe Arg Ala Ser Trp Thr Ala Phe Ala Arg Thr Gly Asp Pro Gly
        435                 440                 445

Trp Pro Thr Tyr Asp Thr Glu Arg Arg Leu Val Gln Val Leu Asp Ala
    450                 455                 460

Ala Pro Glu Val Ile Pro Tyr Pro Glu Glu Thr Ser Arg Arg Leu Trp
465                 470                 475                 480

Glu Arg His Thr Phe Pro Ala Leu Pro Leu Ile Gln
            485                 490

<210> SEQ ID NO 23
<211> LENGTH: 515
<212> TYPE: PRT
<213> ORGANISM: Caulobacter crescentus

<400> SEQUENCE: 23

Met Gly Phe Thr Ala Glu Ala Arg Ser Pro Val Val Ala Thr Thr Asn
1               5                   10                  15

Gly Lys Val Arg Gly Tyr Leu Asp Gly Glu Val Ser Val Phe Lys Gly
            20                  25                  30

Leu Arg Tyr Gly Ala Asp Thr Gly Gly Ala Arg Arg Phe Met Pro Pro
        35                  40                  45

Val Lys Pro Glu Pro Trp Thr Glu Val Lys Asp Ala Leu Ala Tyr Gly
    50                  55                  60

Pro Ala Ser Met Gln Thr Gly Lys Gly Glu Glu Gly Glu Thr Leu Ser
65                  70                  75                  80

Glu Asp Cys Leu Phe Leu Asn Val Trp Thr Pro Ala Arg Ala Ser Arg
                85                  90                  95

Lys Thr Gly Leu Ala Asp Gly Ala Lys Arg Pro Val Met Phe Tyr Ile
            100                 105                 110

His Gly Gly Ala Tyr Asn Gly Gly Ser Gly Ala Ser Pro Trp Tyr Glu
        115                 120                 125

Gly Thr Lys Leu Ala Lys Arg Gly Asp Val Val Val Thr Val Asn
    130                 135                 140

His Arg Leu Asn Ala Phe Gly Tyr Leu Tyr Leu Ala Arg Leu Phe Asn
145                 150                 155                 160

Ala Pro Ser Val Ala Asp Ser Gly Asn Val Gly Gln Leu Asp Leu Val
                165                 170                 175

Leu Ala Leu Gln Trp Val Arg Asp Asn Ile Ala Arg Phe Gly Gly Asp
            180                 185                 190

Pro Asp Cys Val Met Leu Phe Gly Gln Ser Gly Gly Ala Lys Ile
        195                 200                 205

Ala Thr Leu Met Ala Met Pro Ser Ala Lys Gly Leu Phe His Arg Ala
    210                 215                 220

Ala Thr Met Ser Gly Gln Gln Val Thr Val Gly Gly Pro Phe Asn Ala
225                 230                 235                 240

Thr Arg Arg Ala Lys Ala Phe Leu Asp Lys Leu Gly Val Lys Asp Leu
                245                 250                 255

Ala Ala Leu Arg Ala Leu Pro Ala Ala Glu Met Leu Ala Gly Leu Lys
            260                 265                 270

Ala Val Asp Pro Ile Ala Gly Ser Gly Gly Val Tyr Val Gly Pro Val
        275                 280                 285
```

Leu Asp Gln Arg Ser Leu Leu Arg His Pro Phe Phe Pro Asp Ala Ala
            290                 295                 300

Pro Gln Ser Leu Ser Ile Pro Met Met Val Gly Asn Thr His Asp Glu
305                 310                 315                 320

Thr Lys Gly Phe Ile Gly Trp Asp Ala Lys Ala Phe Pro Gln Thr Trp
                325                 330                 335

Asp Glu Val Ile Ala Arg Leu Pro Gly Gln Phe Ala Ala Arg Ile Asp
            340                 345                 350

Ile Asp Pro Glu Thr Val Val Ala Phe Tyr Arg Gln Thr Tyr Pro Asn
            355                 360                 365

Tyr Ser Pro Ala Asp Val Phe Phe Ala Ala Ser Thr Ala Gly Arg Ser
370                 375                 380

Trp Lys Ala Ala Ile Ile Gln Asp Glu Glu Arg Ala Lys Ala Gly Ala
385                 390                 395                 400

Pro Ala Phe Ala Tyr Gln Val Asn Trp Arg Ser Pro Ile Gln Gly Gly
                405                 410                 415

Ile Phe Gly Ala Pro His Thr Ile Asp Ile Gly Leu Val Phe Gly Thr
            420                 425                 430

Leu Asp Ala Lys Gly Ser Ile Val Gly Thr Gly Pro Asp Ser Val Ala
            435                 440                 445

Met Ser Asn Thr Met Ser Asp Ala Phe Ile Ala Phe Ala Arg Thr Gly
450                 455                 460

Asp Pro Asn Gly Gly Ala Leu Pro Lys Trp Glu Pro Tyr Thr Leu Pro
465                 470                 475                 480

Arg Arg Gln Thr Met Val Phe Asp Thr Val Ser Arg Leu Glu Asp Asp
                485                 490                 495

Pro Arg Gly Val Glu Arg Glu Phe Phe Asn Arg Val Pro Phe Thr Gln
            500                 505                 510

Phe Gly Thr
        515

<210> SEQ ID NO 24
<211> LENGTH: 497
<212> TYPE: PRT
<213> ORGANISM: Clostridium acetobuylicum

<400> SEQUENCE: 24

Met Gly Thr Ile Ala Glu Thr Lys Tyr Gly Lys Leu Glu Gly Ile Lys
1               5                   10                  15

Glu Asn Gly Ile Asn Lys Trp Leu Gly Ile Pro Tyr Ala Lys Pro Pro
            20                  25                  30

Val Gly Glu Leu Arg Phe Lys Arg Thr Val Glu Cys Glu Pro Trp Asn
        35                  40                  45

Gly Val Arg Tyr Ala Lys Lys His Gly Ser Lys Pro His Gln Phe Ala
    50                  55                  60

Asn Thr Ser Glu Glu Val Gly Ile Glu Ser Glu Asp Cys Leu Tyr Met
65                  70                  75                  80

Asn Ile Trp Ala Pro Glu Asn Ala Lys Asn Ser Pro Val Phe Val Trp
                85                  90                  95

Ile Tyr Gly Gly Ala Tyr Ala Met Gly Ser Cys Ser Glu Ala Tyr Tyr
            100                 105                 110

Asp Gly Thr Asn Phe Ala Lys Glu Gly Ile Val Tyr Val Ala Phe Asn
        115                 120                 125

Tyr Arg Leu Gly Val Leu Gly Phe Tyr Asp Phe Thr Met Tyr Asp Asp
    130                 135                 140

```
Ser Phe Asp Ser Asn Cys Gly Val Ser Asp Gln Ile Met Ala Leu Lys
145                 150                 155                 160

Trp Val Lys Glu Asn Ile Glu Ala Phe Gly Asp Pro Asn Asn Ile
            165                 170                 175

Thr Ile Ala Gly Glu Ser Ala Gly Ala Ala Ser Val Thr Asn Met Leu
            180                 185                 190

Ala Val Pro Lys Ala Lys Gly Leu Phe Asn Lys Ala Ile Ala Glu Ser
            195                 200                 205

Pro Leu Pro Gly Cys Val Thr Ser His Asn Thr Ala Arg Leu Ile Thr
210                 215                 220

Asp Ile Tyr Leu Lys Arg Leu Gly Leu Glu Ala Ser Glu Val His Lys
225                 230                 235                 240

Leu Lys Thr Met Glu Leu Glu Asp Ile Lys Lys Ala Ala Leu Tyr Val
            245                 250                 255

Ile Asp Asp Thr Cys Ser Ser Tyr Pro Gly Met Tyr Ile Pro Gly Pro
            260                 265                 270

Val Leu Asp Asp Leu Ile Pro Arg Leu Pro Trp Glu Gly Ile Ala Leu
            275                 280                 285

Gly Ser Ser Lys Gly Val Lys Leu Ile Ile Gly Thr Asn His Asp Glu
290                 295                 300

Gly Thr Leu Phe Ile Asn Lys Asn Lys Ser Met Leu Pro Gly Gly Trp
305                 310                 315                 320

Lys Asp Val Glu Arg Met Leu Arg Met Asn Lys Cys Phe Asp Ser Leu
            325                 330                 335

Pro Lys Ile His Lys Leu Tyr Asp Lys Phe Ser Glu Glu Met Ile Gln
            340                 345                 350

Ile Gln Glu Ile Met Lys Asp Arg Thr Phe Leu Val Asp Ser Ile Lys
            355                 360                 365

Val Ala Asp Ala Gln Ser Glu Lys Asn Asp Thr Trp Met Tyr Arg Phe
370                 375                 380

Asp Tyr Ala Pro Ile Ser Ala Lys Leu Asn Gly Leu Gly Ala Thr His
385                 390                 395                 400

Ala Val Glu Val Ser Val Ala Leu Asn Asn Thr Lys Gly Glu Gly Ile
            405                 410                 415

Ala Tyr Ser Phe Trp Arg Asp Thr Pro Glu Asp Ile Ile Lys Lys Phe
            420                 425                 430

Ile Glu Asn Met His Met Ser Trp Val Asn Phe Ala Lys Thr Gly Asp
            435                 440                 445

Pro Asn Gly Asn Leu Asp Ile Glu Trp Lys Lys Tyr Asp Ser Lys Ser
450                 455                 460

Arg Thr Thr Phe Val Phe Asp Glu Glu Asn Lys Val Glu Asn Asn Pro
465                 470                 475                 480

Ala Lys Asp Ile Tyr Glu Thr Trp Arg Asp Ile Lys Leu Tyr Thr Asp
            485                 490                 495

Ile

<210> SEQ ID NO 25
<211> LENGTH: 489
<212> TYPE: PRT
<213> ORGANISM: artificial
<220> FEATURE:
<223> OTHER INFORMATION: protein of unknown origin, database entry gi
      7546320

<400> SEQUENCE: 25

Met Thr His Gln Ile Val Thr Thr Gln Tyr Gly Lys Val Lys Gly Thr
```

-continued

```
  1               5               10              15
Thr Glu Asn Gly Val His Lys Trp Lys Gly Ile Pro Tyr Ala Lys Pro
             20                  25                  30

Pro Val Gly Gln Trp Arg Phe Lys Ala Pro Glu Pro Glu Val Trp
             35                  40                  45

Glu Asp Val Leu Asp Ala Thr Val Tyr Gly Pro Val Cys Pro Gln Pro
 50                  55                  60

Ser Asp Leu Leu Ser Leu Ser Tyr Lys Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Met
            130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
            195                 200                 205

Gln Lys Ala Ile Met Glu Ser Gly Ala Ser Arg Thr Met Thr Lys Glu
            210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
            275                 280                 285

Glu Lys Ser Ile Ala Glu Gly Ala Ala Ser Gly Ile Pro Leu Leu Ile
            290                 295                 300

Gly Thr Thr Arg Asp Glu Gly Tyr Phe Phe Thr Pro Asp Ser Asp
305                 310                 315                 320

Val Tyr Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Val Thr Asp Leu Leu Phe Trp Arg Pro Ala Val
            355                 360                 365

Ala Phe Ala Ser Ala Gln Ser His Tyr Ala Pro Val Trp Met Tyr Arg
            370                 375                 380

Phe Asp Trp His Pro Glu Lys Pro Tyr Asn Lys Ala Phe His Thr
385                 390                 395                 400

Leu Glu Leu Pro Phe Val Gly Asn Leu Asp Glu Leu Glu Arg Met
                405                 410                 415

Ala Lys Ala Glu Ile Thr Asp Glu Val Lys Gln Leu Ser His Thr Ile
            420                 425                 430
```

-continued

Gln Ser Ala Trp Thr Thr Phe Ala Lys Thr Gly Asn Pro Ser Thr Glu
        435                 440                 445

Ala Val Asn Trp Pro Ala Tyr His Glu Glu Ser Arg Glu Thr Val Ile
450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 26
<211> LENGTH: 320
<212> TYPE: PRT
<213> ORGANISM: Burkholderia cepacia

<400> SEQUENCE: 26

Ala Asp Asn Tyr Ala Ala Thr Arg Tyr Pro Ile Ile Leu Val His Gly
1               5                   10                  15

Leu Thr Gly Thr Asp Lys Tyr Ala Gly Val Leu Glu Tyr Trp Tyr Gly
            20                  25                  30

Ile Gln Glu Asp Leu Gln Gln Arg Gly Ala Thr Val Tyr Val Ala Asn
        35                  40                  45

Leu Ser Gly Phe Gln Ser Asp Asp Gly Pro Asn Gly Arg Gly Glu Gln
50                  55                  60

Leu Leu Ala Tyr Val Lys Thr Val Leu Ala Ala Thr Gly Ala Thr Lys
65                  70                  75                  80

Val Asn Leu Val Gly His Ser Gln Gly Gly Leu Thr Ser Arg Tyr Val
                85                  90                  95

Ala Ala Val Ala Pro Asp Leu Val Ala Ser Val Thr Thr Ile Gly Thr
            100                 105                 110

Pro His Arg Gly Ser Glu Phe Ala Asp Phe Val Gln Gly Val Leu Ala
        115                 120                 125

Tyr Asp Pro Thr Gly Leu Ser Ser Thr Val Ile Ala Ala Phe Val Asn
130                 135                 140

Val Phe Gly Ile Leu Thr Ser Ser Ser Asn Asn Thr Asn Gln Asp Ala
145                 150                 155                 160

Leu Ala Ala Leu Lys Thr Leu Thr Thr Ala Gln Ala Ala Thr Tyr Asn
                165                 170                 175

Gln Asn Tyr Pro Ser Ala Gly Leu Gly Ala Pro Gly Ser Cys Gln Thr
            180                 185                 190

Gly Ala Pro Thr Glu Thr Val Gly Gly Asn Thr His Leu Leu Tyr Ser
        195                 200                 205

Trp Ala Gly Thr Ala Ile Gln Pro Thr Ile Ser Val Phe Gly Val Thr
210                 215                 220

Gly Ala Thr Asp Thr Ser Thr Ile Pro Leu Val Asp Pro Ala Asn Ala
225                 230                 235                 240

Leu Asp Pro Ser Thr Leu Ala Leu Phe Gly Thr Gly Thr Val Met Val
                245                 250                 255

Asn Arg Gly Ser Gly Gln Asn Asp Gly Val Val Ser Lys Cys Ser Ala
            260                 265                 270

Leu Tyr Gly Gln Val Leu Ser Thr Ser Tyr Lys Trp Asn His Leu Asp
        275                 280                 285

Glu Ile Asn Gln Leu Leu Gly Val Arg Gly Ala Asn Ala Glu Asp Pro
290                 295                 300

Val Ala Val Ile Arg Thr His Ala Asn Arg Leu Lys Leu Ala Gly Val
305                 310                 315                 320

<210> SEQ ID NO 27
<211> LENGTH: 1473
<212> TYPE: DNA
<213> ORGANISM: Bacillus licheniformis

<400> SEQUENCE: 27

```
atgtatgata caactgtcga aacacgcttc ggaaagctga aaggcagagc ggaaaacgga      60
gtccgtatct ttaaaggcgt tccatacgca aaacctcccg tcggcgacct aaggtttcgg     120
gaaccgcagc gaatggaggc ctgggaaggt gagctggatg cttttcaatt tggcccggtt     180
tgtccgcagc ctgatggggt attgcctgag tcagcggggg ttcaaaagtc tgaggattgc     240
ctttatttaa atgtgtacgc acccgaagag gcggacgggg atctgcctgt tatggtgtgg     300
attcatgggg gcgcttttta tcgcggcgcc ggaagtgaac cgctctatga cgggactcag     360
cttgcaaagc agggaaaggt gatcgtggtc accatcaatt atcgcctcgg tccgttcggt     420
tttttgcatc tatcctcaat tgatgattcc tacagcagca atcttggcct gctggatcaa     480
atcgcggctc tcgagtgggt gaaagacaat atcgctttct tggcggaga ccgtcatcac      540
attacggttt ttggagagtc ggcgggatcg atgagcatcg cttcgctttt ggcgatgccg     600
aaagcaaagg ggcttttta caggccatt atggaaagcg gggcttccgc aactatgtcc       660
gataagcttg cgaaagctgc agcagaaaga ttcttaagga ttctcgatat tgatcatcat     720
catctggagc gccttcatga tgtatctgat caagaacttc ttgaagccgc cgatcagctg     780
cgcactttaa tgggagaaaa tatttttgaa ttgattttc tgcctgcgct tgacgaaaaa      840
accttgccgc tgaagccgga ggtcgccgtc gcaaaaggcg cggcaaaaga gatcaatcta     900
ttaatcggaa caaccgtga tgaaggcgtc ttgttttttc cctctgattc ggatcttttg      960
cctgagagca agatcaacga gatttttagaa gaatacatgg gtaaagaggc cgccgaagcc   1020
gcctcctctc tgtatccgag gtcattggaa ggccatgttg atatgatgac agatctgatc    1080
ttttggcatc cgtctgttgt gttcgcttcg gctcaatcac gatatgcatc tgtctttatg    1140
taccggtttg actggcatgc ggattcagag cagccgccgt tcaacaaagc tgcgcacggc    1200
ttagagattc cgtttgtatt tggaaatatg gacattttgg aacagctgac aggtacgaag    1260
gccggtgaag aagcgcagct gcttgctgaa cagatccagg ctgcctgggt gtcttttgcc    1320
cgatccggaa atccgagcac cgatgatgtc agctggcctg attatgatga agattcacgg    1380
aaaacgctga tttttgatca agaggtcgca gttgaaagcg atccttattc agataagaga    1440
aagatgttga cagccccgaa cccgcagatt tag                                 1473
```